(12) United States Patent
Pluth et al.

(10) Patent No.: US 9,664,696 B1
(45) Date of Patent: May 30, 2017

(54) COMPOUNDS FOR DETERMINING THE PRESENCE OF HYDROGEN SULFIDE AND METHODS OF USE

(71) Applicant: University of Oregon, Eugene, OR (US)

(72) Inventors: Michael D. Pluth, Eugene, OR (US); T. Spencer Bailey, Eugene, OR (US); Leticia A. Montoya, Eugene, OR (US); Taylor F. Pearce, Eugene, OR (US)

(73) Assignee: University of Oregon, Eugene, OR (US)

( * ) Notice: Subject to any disclaimer, the term of this patent is extended or adjusted under 35 U.S.C. 154(b) by 274 days.

(21) Appl. No.: 14/292,378

(22) Filed: May 30, 2014

Related U.S. Application Data

(60) Provisional application No. 61/829,196, filed on May 30, 2013, provisional application No. 61/869,502, filed on Aug. 23, 2013.

(51) Int. Cl.
*C12Q 1/28* (2006.01)
*G01N 33/84* (2006.01)

(52) U.S. Cl.
CPC .................................... *G01N 33/84* (2013.01)

(58) Field of Classification Search
None
See application file for complete search history.

(56) References Cited

U.S. PATENT DOCUMENTS

| | | | | |
|---|---|---|---|---|
| 2007/0202198 A1* | 8/2007 | Purcell | ...................... | A61K 8/97 424/725 |
| 2009/0184005 A1* | 7/2009 | Zhang | ................ | G01N 27/4045 205/786.5 |
| 2010/0099683 A1* | 4/2010 | Tomkinson | .......... | A61K 31/397 514/249 |

OTHER PUBLICATIONS

Montoya et al. J. Org. Chem. (2013; published on the Web Jun. 4, 2013) 78: 6550-6557.*
Yu et al. Chinese J. Chem. (2007) 25: 797-801.*
Bailey et al. J. Am. Chem. Soc. (2013) 135: 16697-16704.*
Gu et al., "Development of a boron-dipyrromethene-$Cu^{2+}$ ensemble based colorimetric probe toward hydrogen sulfide in aqueous media," *Tetrahedron Letters* 52:5000-5003, 2011.
Jarosz et al., "Microplate-Based Colorimetric Detection of Free Hydrogen Sulfide," *Analytical Chemistry* 85:3638-3643, 2013.
Lee et al., "Detection of hydrogen peroxide with chemiluminescent micelles," *International Journal of Nanomedicine* 3(4):471-476, 2008.
Lippert et al., "Reaction-Based Fluorescent Probes for Selective Imaging of Hydrogen Sulfide in Living Cells," *Journal of the American Chemical Society* 133:10078-10080, 2011.
Liu et al., "Capture and Visualization of Hydrogen Sulfide by a Fluorescent Probe," *Angew. Chem. Int. Ed.* 50:10327-10329, 2011.
Liu et al., "A visible light excitable colorimetric and fluorescent ESIPT probe for rapid and selective detection of hydrogen sulfide," *Organic & Biomolecular Chemistry* 12:438-445, 2013.
Maity et al., "A probe for ratiometric near-infrared fluorescence and colorimetric hydrogen sulfide detection and imaging in living cells," *RSC Advances* 4:11147-11151, 2014.
Montoya et al., "Selective turn-on fluorescent probes for imaging hydrogen sulfide in living cells," *Chemical Communications* 48:4767-4769, 2012.
Peng et al., "A Fluorescent Probe for Fast and Quantitative Detection of Hydrogen Sulfide in Blood," *Angew. Chem. Int. Ed.* 50:9672-9675, 2011.
Qian et al., "Selective fluorescent probes for live-cell monitoring of sulphide," *Nature Communications* 2(495)1-7, 2011.
Roda et al., "Analytical chemiluminescence and bioluminescence: latest achievements and new horizons," *Anal Bioanal Chem* 402:69-76, 2011.
Saha et al., "A colorimetric and fluorometric BODIPY probe for rapid, selective selection of $H_2S$ and its application in live cell imaging," *Organic & Biomolecular Chemistry* 11:8166-8170, 2013.
Sasakura et al., "Development of a Highly Selective Fluorescence Probe for Hydrogen Sulfide," *Journal of the American Chemical Society* 133:18003-18005, 2011.
Shen et al., "Measurement of plasma hydrogen sulfide in vivo and in vitro," *Free Radical Biology & Medicine* 50:1021-1031, 2011.
Van De Bittner et al., "In vivo imaging of hydrogen peroxide production in a murine tumor model with a chemoselective bioluminescent reporter," *PNAS* 107(50):21316-21321, 2010.
Wei et al., "NBD-based colorimetric and fluorescent turn-on probes for hydrogen sulfide," *Organic & Biomolecular Chemistry* 12:479-485, 2013.
Wu et al., "A selective colorimetric and ratiometric fluorescent probe for hydrogen sulfide," *Organic & Biomolecular Chemistry* 10:8342-8347, 2012.
Yamaguchi et al., "Evaluation of chemiluminescence reagents for selective detection of reactive oxygen species," *Analytica Chimica Acta* 665:74-78, 2010.
Zhang et al., "On-Site Visual Detection of Hydrogen Sulfide in Air Based on Enhancing the Stability of Gold Nanoparticles," *ACS Applied Materials & Interfaces* 6:6300-6307, 2014.
Zhang et al., "Highly selective and sensitive colorimetric probe for hydrogen sulfide by a copper (II) complex of azo-dye based on chemosensing ensemble approach," *Spectrochimica Acta Part A: Molecular and Biomolecular Spectroscopy* 90:35-39, 2012.
Zhang et al., "A dicopper complex chemiluminescence probe for the determination of thiols in the extracts of murine P388 lymphocytic leukemia cell," *Chem. Commun.* pp. 5624-5626, 2009.
Zhao et al., "A highly selective colorimetric chemodosimeter for fast and quantitative detection of hydrogen sulfide," *Analyst* 137:5576-5580, 2012.

*Primary Examiner* — Susan Hanley
(74) *Attorney, Agent, or Firm* — Klarquist Sparkman, LLP

(57) ABSTRACT

Disclosed herein are embodiments of $H_2S$-reactive compounds, or compositions thereof, which can be used to determine the presence of $H_2S$, and in some embodiments quantify $H_2S$. Also disclosed herein are methods of using the $H_2S$-reactive compounds. The methods can use colorimetric, chemiluminescent, or bioluminescent testing methods to determine the presence of and/or amount of $H_2S$ in a sample.

16 Claims, 26 Drawing Sheets
(18 of 26 Drawing Sheet(s) Filed in Color)

8.6  8.5  8.4  8.3  8.2  8.1  8.0  7.9  7.8  7.7  7.6  7.5  7.4  7.3  7.2  7.1  7.0  6.9

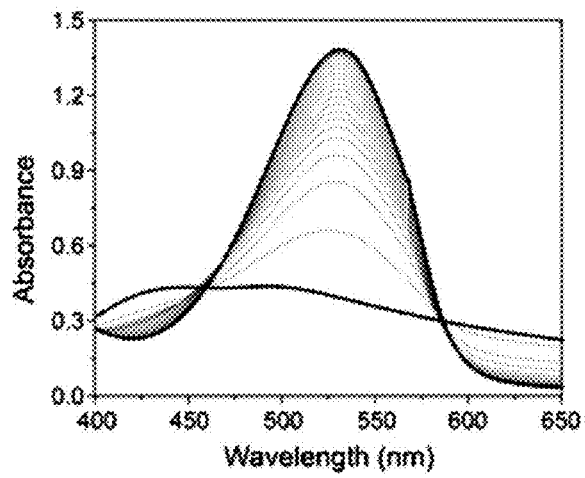
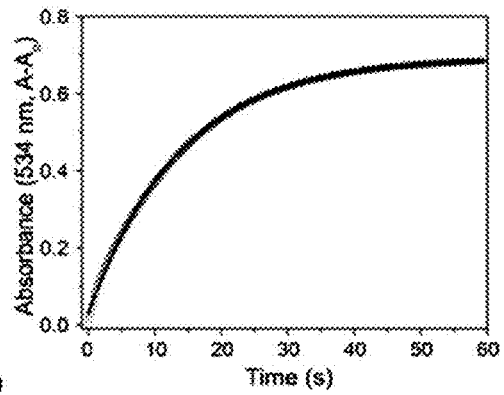
FIG. 17  FIG. 18
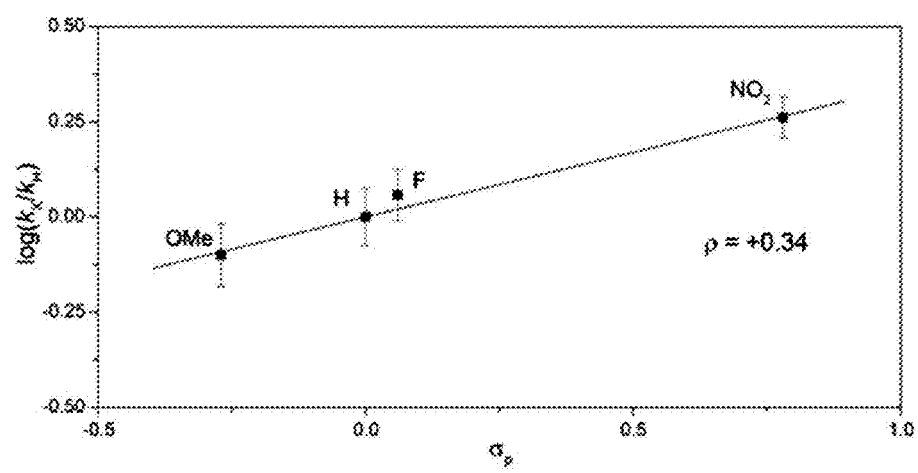
FIG. 19

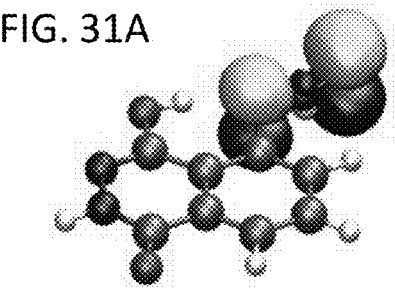
FIG. 31A
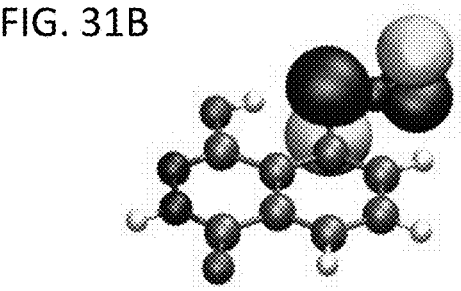
FIG. 31B
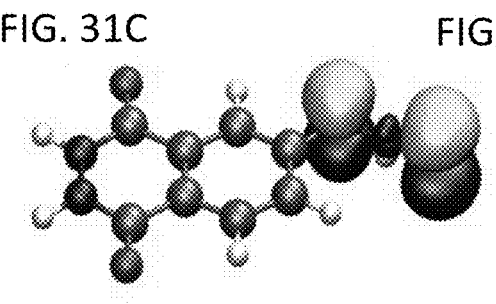
FIG. 31C
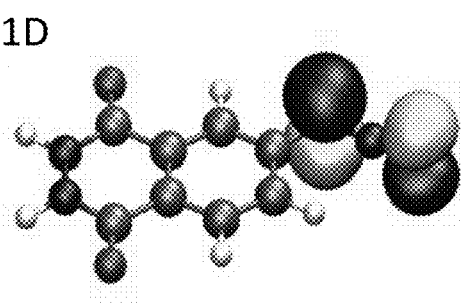
FIG. 31D
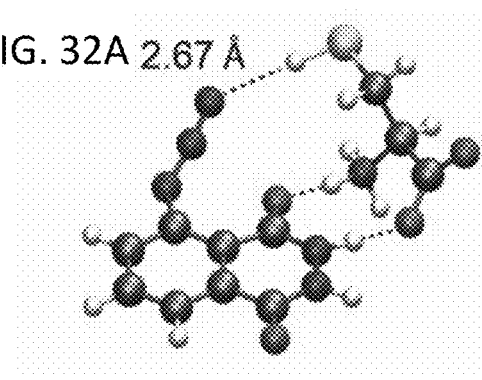
FIG. 32A 2.67 Å
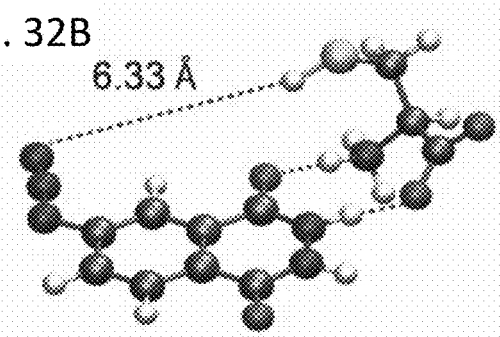
FIG. 32B 6.33 Å

FIG. 34A
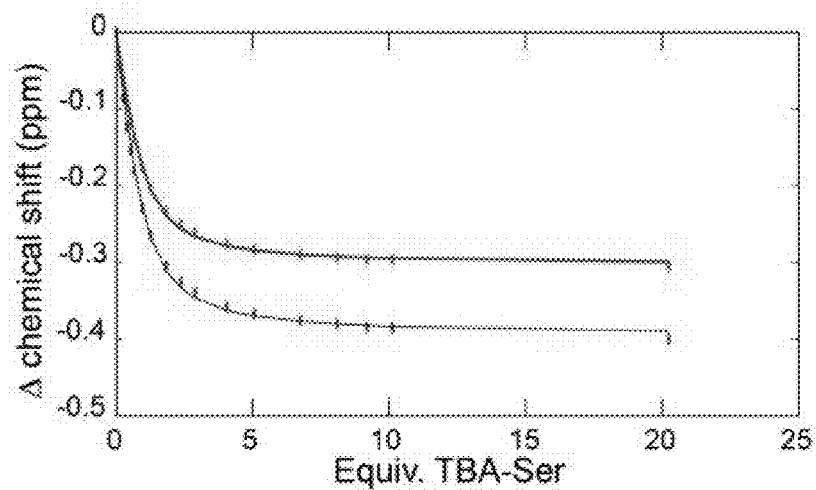
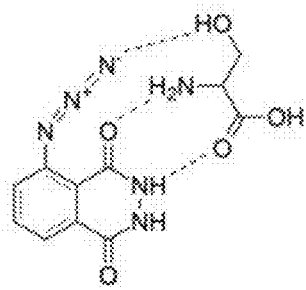
FIG. 34B
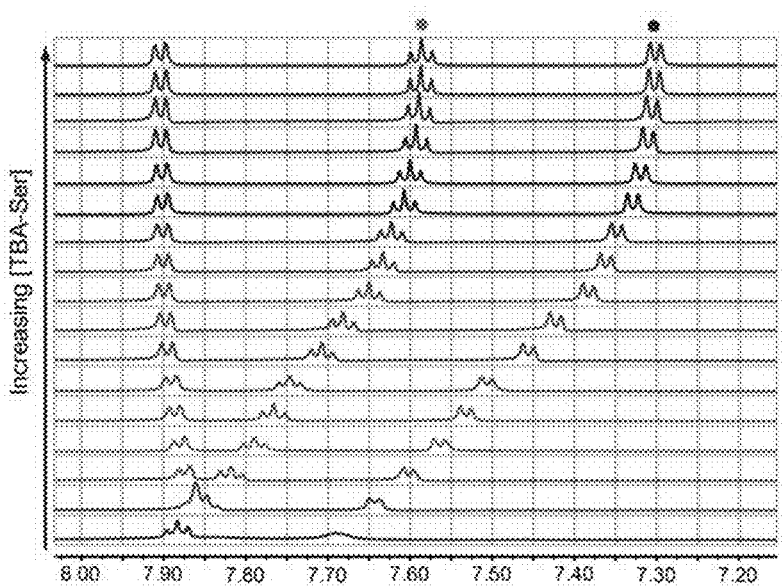
FIG. 34C

US 9,664,696 B1

COMPOUNDS FOR DETERMINING THE PRESENCE OF HYDROGEN SULFIDE AND METHODS OF USE

CROSS REFERENCE TO RELATED APPLICATION

This application claims the benefit of U.S. Provisional Patent Application No. 61/829,196, filed on May 30, 2013, and U.S. Provisional Patent Application No. 61/869,502, filed on Aug. 23, 2013, each of which is incorporated herein by reference in its entirety.

ACKNOWLEDGMENT OF GOVERNMENT SUPPORT

The claimed invention was made with government support under grant number R00 GM092970 awarded by the National Institutes of Health, National Institute of General Medical Sciences. The government has certain rights in the claimed invention.

FIELD

The present disclosure concerns embodiments of $H_2S$-reactive compounds, or compositions thereof, suitable for determining the presence of and/or quantifying the amount of hydrogen sulfide in a sample, and embodiments of methods for using the disclosed compounds or compositions.

BACKGROUND

Hydrogen sulfide ($H_2S$), although generally known for its toxicity and characteristic odor, is now recognized as an important signaling molecule with diverse biological roles. The biological roles of $H_2S$ range from roles in angiogenesis to wound healing. In mammals, $H_2S$ production is derived primarily from three enzymes: cystathionine-γ-lyase (CSE), cystathionine-β-synthase (CBS), and 3-mercaptopyruvate sulfotransferase (3-MST). The expression of these enzymes in different tissues suggests a broad importance and significance of $H_2S$ in the cardiovascular, circulatory, respiratory, urinary, and nervous systems. Abnormal $H_2S$ regulation, however, has been associated with hypertension, diabetes, as well as various diseases of mental deficiency including Down's syndrome and Alzheimer's disease. In addition to the pathophysiological conditions associated with $H_2S$ misregulation, $H_2S$ can also act on specific cellular targets, including heme proteins, cysteine residues on KATP channels, nitric oxide, and other emerging targets. As such, $H_2S$-reactive compounds, compositions, kits, and methods of using the same are needed.

SUMMARY

Disclosed herein are $H_2S$-reactive compounds, including combinations and compositions thereof, kits comprising, consisting essentially of, or consisting of the $H_2S$-reactive compounds, as well as methods for using the disclosed $H_2S$-reactive compounds. In some embodiments, the methods comprise providing an $H_2S$-reactive compound, or a composition thereof, exposing a sample to the $H_2S$-reactive compound, or composition thereof, and analyzing the sample for a reaction product obtained from reaction between the $H_2S$-reactive compound and $H_2S$ to determine whether $H_2S$ is present. In some embodiments, the $H_2S$-reactive compound can be a colorimetric compound precursor that is converted by reaction with $H_2S$ to a reaction product that produces a color change. In some embodiments, the $H_2S$-reactive compound can be a chemiluminescent compound precursor that is converted by reaction with $H_2S$ and an oxidant, an enzyme, a base, and an optional enhancer (or any combination thereof) to a reaction product that produces chemiluminescence. In other embodiments, the $H_2S$-reactive compound can be a bioluminescent compound precursor that is converted by reaction with $H_2S$ and an enzyme to a reaction product that produces bioluminescence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 17 is a UV-visible spectrum obtained from reaction of an H$_2$S-reactive compound embodiment with excess NaSH.

FIG. 18 is a graph of absorbance versus time (seconds) illustrating time course data of the absorbance at 534 nm of the H$_2$S-reactive compound embodiment of FIG. 17.

FIG. 19 is a Hammett plot of the reaction of H$_2$S-reactive compound embodiments disclosed herein with NaSH under pseudo first order conditions.

FIGS. 31A-31D are images showing frontier molecular orbitals of two H$_2$S-reactive compound embodiments disclosed herein; FIGS. 31A and 31C illustrate the HOMOs of the two H$_2$S-reactive compound embodiments and FIGS. 31B and 31D illustrate the LUMOs of the two H$_2$S-reactive compound embodiments.

FIGS. 32A and 32B are images showing a calculated compound/cysteine structure of two H$_2$S-reactive compound embodiments comprising azides, showing hydrogen bonding between cysteine and the azide moiety of one H$_2$S-reactive compound (FIG. 32A) and the lack of hydrogen bonding, based on distance, between cysteine and an azide moiety of a different H$_2$S-reactive compound embodiment (FIG. 32B).

FIGS. 34A-34C illustrate a non-linear fitting of aromatic chemical shifts based on a 1:1 binding model of an H$_2$S-reactive compound embodiment and serine (FIG. 34A), a proposed binding interaction between the H$_2$S-reactive compound and serine (FIG. 34B), and stacked $^1$H NMR spectra illustrating changes in the aromatic region of the H$_2$S-reactive compound during the course of a titration (FIG. 34C).

DETAILED DESCRIPTION

I. Introduction

Figure 1:
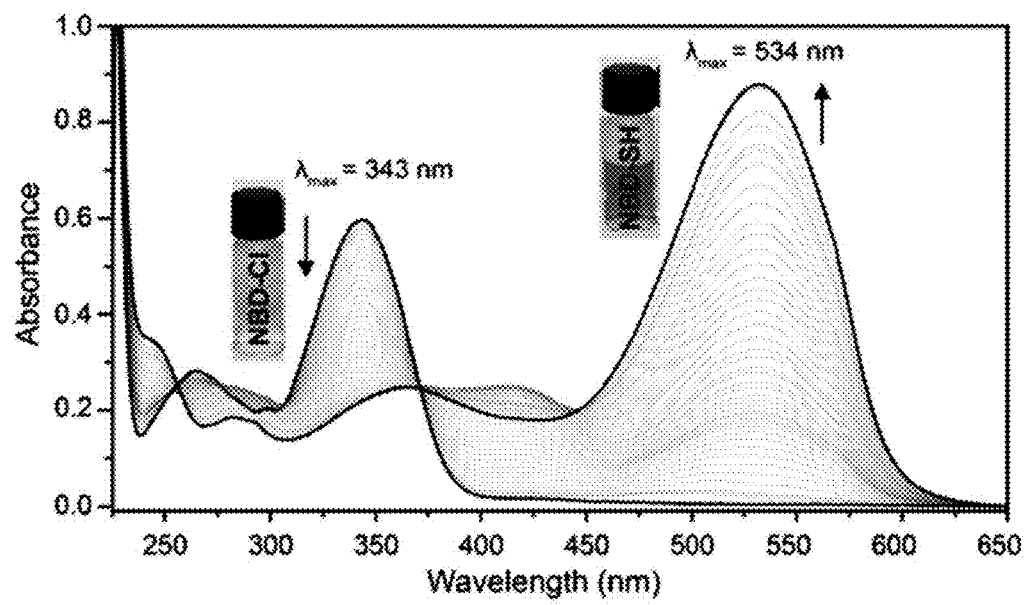
FIG. 1 is a UV-visible spectrum of an $H_2S$-reactive compound embodiment disclosed herein before and after reacting with NaSH, an $H_2S$ donor.

The present disclosure concerns methods for determining the presence of and/or quantifying the amount of H$_2$S in a sample, compounds and/or compositions for use in such methods, and kits comprising, consisting essentially of, or consisting of such compounds and/or compositions. In some embodiments, the methods disclosed herein utilize biocompatible compounds and/or compositions that can be used in various different methods for quantifying and/or determining the presence of H$_2$S. Major limitations of traditional methods used in the art for H$_2$S detection, such as sulfide-selective electrodes, gas chromatography, or methylene blue assays, include poor compatibility with live cells or require extensive preparation prior to analysis. Another major challenge for traditional H$_2$S detection is designing compounds that effectively differentiate H$_2$S from cellular glutathione ("GSH"), which often is present in concentrations much higher than H$_2$S. Particular H$_2$S-reactive compound embodiments disclosed herein provide an advantage over traditional methods and compounds used to determine the presence of H$_2$S in samples as the H$_2$S-reactive compounds disclosed herein react solely with H$_2$S and do not exhibit the same reactivity toward thiol compounds. Accordingly, such H$_2$S-reactive compounds can be used in samples that comprise both H$_2$S and thiols, such as glutathione, cysteine, and the like, without requiring the use of methods or instrumentation to distinguish between reactions products formed by reactions between the H$_2$S-reactive compound and H$_2$S and/or thiol compounds. The embodiments disclosed herein address these limitations by providing biocompatible alternatives to typical probes used for $H_2S$ detection. In some embodiments, disclosed $H_2S$-reactive compounds exhibit properties that facilitate their use as detectors of $H_2S$, even at very low detection limits, and in some embodiments their selectivity can be modified by controlling sample-compound interactions.

II. Terms and Definitions

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided:

Aldehyde: $R^aCHO$, wherein $R^a$ is the atom of the formulas disclosed herein to which the aldehyde group is attached.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane, alkene, alkyne). An alkyl group can be branched, straight-chain, or cyclic.

Alkenyl: An unsaturated monovalent hydrocarbon having at least two carbon atoms 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic, cis, or trans (e.g., E or Z).

Alkynyl: An unsaturated monovalent hydrocarbon having at least two carbon atoms 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic.

Alkoxy: —O-alkyl, with exemplary embodiments including, but not limited to, methoxy, ethoxy, n-propoxy, iso-propoxy, n-butoxy, t-butoxy, sec-butoxy, n-pentoxy.

Amide: $R^aC(O)NR^bR^c$ wherein $R^a$ is the atom of the formulas disclosed herein to which the amide is attached, and each of $R^b$ and $R^c$ independently is selected from alkyl, alkenyl, alkynyl, aryl, heteroalkyl, heteroalkenyl, heteroalkynyl, heteroaryl, hydrogen, and any combination thereof. In an independent embodiment, Rb or Rc independently can be a fluorophore selected from, but not limited to, coumarin, naphthalimide, fluorescein, rhodamine, rhodol, Cy3, or Cy5.

Amine: $R^aNH_2$, $R^aNHR^b$, or $R^aNR^bR^c$, wherein $R^a$ is the atom of the formulas disclosed herein to which the amine is attached, and each of $R^b$ and $R^c$ independently is selected from alkyl, alkenyl, alkynyl, aryl, heteroalkyl, heteroalkenyl, heteroalkynyl, heteroaryl, and any combination thereof.

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic aryl group.

Carboxyl: $R^aC(O)OR^b$, wherein $R^a$ is the atom of the formulas disclosed herein to which the carboxyl group is attached and wherein $R^b$ is alkyl, alkenyl, alkynyl, aryl, heteroalkyl, heteroalkenyl, heteroalkynyl, heteroaryl, hydrogen, and any combination thereof.

Detectable signal: A color change that occurs when a colorimetric compound precursor, a chemiluminescent compound precursor, or a bioluminescent compound precursor is converted to a colorimetric compound, a chemiluminescent compound, or a bioluminescent compound.

Haloalkyl: An alkyl group wherein one or more hydrogen atoms, such as one to three hydrogen atoms, is replaced with a halogen atom, such as fluoro, bromo, chloro, iodo, or combinations thereof. In an independent embodiment, haloalkyl can be a $CX_3$ group, wherein each X can independently be selected from fluoro, bromo, chloro, or iodo.

Heteroalkyl/Heteroalkenyl/Heteroalkynyl: An alkyl, alkenyl, or alkynyl group comprising at least one heteroatom to six heteroatoms, such as one to four heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Heterocyclyl: A ring system comprising at least one saturated or unsaturated ring comprising at least one heteroatom to six heteroatoms, such as one heteroatom to four heteroatoms, selected from oxygen, nitrogen, sulfur, selenium, phosphorous, and oxidized forms thereof, and comprising at least one carbon atom to 20 carbon atoms, such as one carbon atom to 15 carbon atoms, or one carbon atom to 10 carbon atoms. These groups encompass, for example, a saturated heterocyclyl fused with one or more aromatic hydrocarbons or heteroaryl groups. In exemplary embodiments, the heterocyclyl can be substituted with two oxo groups.

Ketone: $R^aC(O)R^b$, wherein $R^a$ is the atom of the formulas disclosed herein to which the ketone is attached, and $R^b$ is selected from alkyl, alkenyl, alkynyl, aryl, heteroalkyl, heteroalkenyl, heteroalkynyl, heteroaryl, and any combination thereof.

NBD: Nitrobenzoxadiazole.

Sulfonyl/Sulfonate: A functional group having a formula $R^aSO_2R^b$, wherein $R^a$ is the atom of the formulas disclosed herein to which the sulfonyl or sulfonate is attached, and $R^b$ is selected from hydrogen, alkyl, alkenyl, alkynyl, aryl, heteroalkyl, heteroalkenyl, heteroalkynyl, heteroaryl, and any combination thereof.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein.

III. Methods, Compounds, Compositions, and Kits for Determining the Presence of $H_2S$ Disclosed herein are embodiments of methods for determining the presence of $H_2S$ comprising, consisting essentially of, or consisting of providing an $H_2S$-reactive compound (or composition thereof) as disclosed herein, exposing a sample to the $H_2S$-reactive compound (or composition thereof), and analyzing the sample for a reaction product obtained from a reaction between the $H_2S$-reactive compound (or composition thereof) and $H_2S$ to determine the presence of $H_2S$ in the sample. In particular disclosed embodiments, methods of analyzing the sample and determining the presence of $H_2S$ can comprise, consist essentially of, or consist of detecting $H_2S$ that is present in a sample. In some embodiments, analyzing the sample and determining the presence of $H_2S$ can comprise, consist essentially of, or consist of determining that $H_2S$ is not present in a sample. In some embodiments, the methods disclosed herein can be used in most any setting wherein $H_2S$ is present. For example, methods disclosed herein can be used to determine the presence of, and quantify the amount of, $H_2S$ in biological samples (in vivo and/or in vitro) and/or environmental samples. In particular disclosed embodiments, methods disclosed herein can be used to test for the presence of and quantify the amount of $H_2S$ in cells, tissue, bodily fluids, and other biological specimens. Certain embodiments of the disclosed methods also can be used to test for the presence of $H_2S$ in environmental samples, such as samples of water, soil, plants, gas, air, and the like. In yet other embodiments, the disclosed methods can be used for non-invasive testing to determine the presence of $H_2S$ in animals or animal models.

In some embodiments of the methods disclosed herein, one or more of the $H_2S$-reactive compounds, or compositions thereof, can be provided in an effective amount for the purpose of determining whether or not a detectable amount of $H_2S$ is present in a particular sample, such as an amount ranging from greater than 0 to at least 100 µM, such as 150 nM to 100 µM, or 50 nM to 1 M $H_2S$ for certain testing embodiments. One or more $H_2S$-reactive compounds, or compositions thereof, can be provided simultaneously or sequentially.

In some embodiments, exposing the sample to an $H_2S$-reactive compound, or composition thereof, can comprise contacting the sample with one or more of the $H_2S$-reactive compounds disclosed herein, or a composition thereof, for a particular time under reaction conditions that promote a reaction between the $H_2S$-reactive compound and any $H_2S$ present in the sample. In certain embodiments, the sample can be contacted with the $H_2S$-reactive compound (or composition thereof) for a time period ranging from greater than 0 to at least 120 minutes, such as 30 seconds to 120 minutes, or 1 minute to 60 minutes, or 1 minute to 45 minutes, or 1 minute to 30 minutes, or 1 minute to 20 minutes. In particular disclosed embodiments, the sample can be contacted with the $H_2S$-reactive compound (or composition thereof) at a certain pH, such as greater than 0 to at least 12, such as 3 to 12, or 6 to 9, or 7 to 7.8, or 7 to 7.4. The pH can be maintained using an appropriate buffer, such as a phosphate buffer (e.g., 3-{[tris(hydroxymethyl)methyl]amino}propanesulfonic acid, tris(hydroxymethyl)methylamine, 4-2-hydroxyethyl-1-piperazineethanesulfonic acid, 2-{[tris(hydroxymethyl)methyl]amino}ethanesulfonic acid, piperazine-N,N'-bis(2-ethanesulfonic acid), or the like).

In some embodiments, the presence of $H_2S$ in a sample can be determined by detecting a signal produced by a reaction product obtained from reaction between an $H_2S$-reactive compound and $H_2S$. In some embodiments, the signal is a color change.

The term "color change" is understood herein to mean that an $H_2S$-reactive compound that does not emit, reflect, or transmit light (which can also be referred to as electromagnetic radiation or luminescence, chemiluminescence, or bioluminescence) having a wavelength within the visible spectrum, such as from 380 nm to 790 nm, is converted to a reaction product that does emit, reflect, or transmit light within the visible spectrum therefore making the conversion visible to the naked eye. This term also includes a color change where a color shift from one color within the visible spectrum to another different color within the visible spectrum occurs and is therefore visible to the naked eye. In an independent embodiment, an $H_2S$-reactive compound emitting, reflecting, or transmitting light at a particular wavelength is converted to a reaction product that emits, reflects, or transmits light at a higher or lower wavelength within the visible spectrum. In an independent embodiment, a color change can involve the conversion of a colorimetric compound precursor to a colorimetric compound that absorbs light at a wavelength of 450 nm to 600 nm, with particular embodiments having a corresponding absorbance of 530 nm to 540 nm. In another independent embodiment, a color change can involve the conversion of a chemiluminescent compound precursor to a chemiluminescent compound that emits luminescence having a wavelength between 400 nm to 600 nm, such as 440 nm to 490 nm. In another independent embodiment, a color change can involve the conversion of a bioluminescent compound precursor to a bioluminescent compound that emits luminescence having a wavelength between 400 nm to 600 nm, such as 550 nm to 600 nm.

In some embodiments, if a reaction product is not produced between an $H_2S$-reactive compound and $H_2S$, then such a reaction product is not detected and can thereby signify the absence of $H_2S$ at a detectable limit and/or the complete absence of $H_2S$ in a sample. In some embodiments, a reaction product obtained from reaction between an $H_2S$-reactive compound and $H_2S$ can be detected by visually observing a signal produced by the reaction product.

The term "visually observing" or "visually detecting" is understood herein to mean observing a change with the naked eye. In some embodiments, the change can be a color change resulting from the conversion of a disclosed colorimetric compound precursor, a disclosed chemiluminescent compound precursor, or a disclosed bioluminescent compound precursor, which does not emit, reflect, or transmit light in the visible spectrum, to a colorimetric compound, a chemiluminescent compound, or a bioluminescent compound that does emit, reflect, or transmit light in the visible spectrum. In some embodiments, this term can refer to a change in luminescence wherein a chemiluminescent compound precursor or a bioluminescent compound precursor that is not luminescent is converted to a chemiluminescent compound or a bioluminescent compound and thereby emits light which can be visually observed in daylight and/or darkness.

In other disclosed embodiments, the reaction product can be further manipulated using an enzyme, a transition metal cation, an oxidant, a base, an optional enhancer, or combination thereof, to elicit a detectable signal. The detectable signal can be a color change, such as a production of a color, chemiluminescence, and/or or a bioluminescence.

In particular disclosed embodiments, colorimetric testing can be used. In other embodiments, chemiluminescent testing can be used. In yet other embodiments, bioluminescent testing can be used. In some embodiments, colorimetric, chemiluminescent, and/or bioluminescent methods do not require equipment other than the human eye to determine the presence of $H_2S$. Such methods therefore provide the ability to analyze samples for $H_2S$ in situations where additional equipment (e.g., UV-vis instruments, fluorometers, or the like) is not available, practical, or desired. Also, the present testing methods allow people with minimal training and/or knowledge of $H_2S$ detection techniques to use the $H_2S$-reactive compounds, compositions, and/or kits disclosed herein to determine the presence of $H_2S$ in samples.

In some embodiments, the disclosed testing methods optionally can be combined with an additional spectroscopic analysis technique. For example, the progress of the reaction between an $H_2S$-reactive compound and $H_2S$ can be monitored using spectroscopy (e.g., UV-visible spectroscopy, fluorescence spectroscopy, etc.). The disclosed additional spectroscopic analysis techniques can be used to determine the amount of $H_2S$ present in a sample. For example, spectroscopic measurements can be taken after the sample has been exposed to an $H_2S$-reactive compound, or composition thereof, to provide a concentration-dependent response curve from which the amount of $H_2S$ present can be determined, as well as the $H_2S$ detection limit of the $H_2S$-reactive compound.

Also disclosed herein are $H_2S$-reactive compounds suitable for use in detecting $H_2S$. In particular disclosed embodiments, the $H_2S$-reactive compounds react chemically with $H_2S$ to form a bond between the $H_2S$-reactive compound and $H_2S$, such as a covalent or electrostatic bond. For example, a thiol-containing reaction product can be obtained. In other disclosed embodiments, the $H_2S$-reactive compounds react chemically with $H_2S$ in a manner such that the $H_2S$ converts the $H_2S$-reactive compounds into a different chemical species, such as a chemical species comprising one or more functional groups that differ from those present in the $H_2S$-reactive compounds. For example, the $H_2S$ can react with a functional group present in the $H_2S$-reactive compound, such as an azide, thereby converting the functional group to a different functional group, such as an amine, and thus altering the reactivity and/or chemical properties of the $H_2S$-reactive compound.

In particular disclosed embodiments, the $H_2S$-reactive compounds used in the disclosed methods can have a Formula 1, illustrated below.

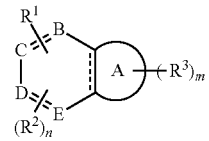

Formula 1 wherein $R^1$ can be a functional group that is capable of being reduced by $H_2S$, or it can be a functional group capable of being irreversibly displaced by $H_2S$; each $R^2$ independently can be an electron withdrawing group or a linker connected to a fluorophore; each $R^3$ independently can be a 5- or 6-membered heteroaryl group, or a 5- or 6-membered heterocyclyl; n can be 0, 1, 2, or 3; m can be 0, 1, or 2; variables B, C, D, and E independently may be selected from carbon or nitrogen; and ring A can be selected from heteroaryl or heterocyclyl. In an independent embodiment, the $H_2S$-reactive compound is not, or is other than, 4-azido-7-nitrobenzo[c][1,2,5]oxadiazole, which has the following structure:

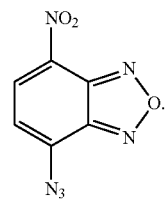

In another independent embodiment, the $H_2S$-reactive compound is not, or is other than, 2-(6-((4-boronobenzyl)oxy)benzo[d]thiazol-2-yl)-4,5-dihydrothiazole-4-carboxylic acid, which has the following structure:

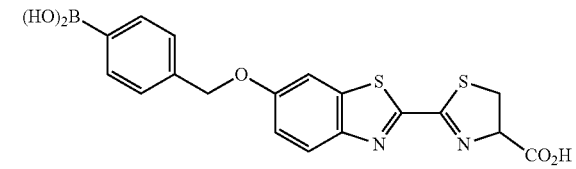 [SMILES: O=C(O)C1CSC(c2nc3ccc(OCc4ccc(B(O)O)cc4)cc3s2)=N1]

In particular disclosed embodiments $R^1$ is selected from an azide, halogen (e.g., chloro, fluoro, bromo, or iodo), mesylate, besylate, tosylate, triflate, ether, or thioether. In some embodiments, the thioether can have a Formula 2 and the ether can have a Formula 3, illustrated below.

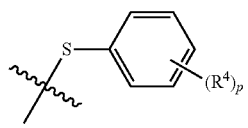

Formula 2

Formula 3

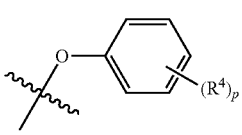

With reference to Formula 2 and Formula 3, each $R^4$ independently can be selected from halogen, alkoxy, nitro, haloalkyl, cyano, sulfonate, carboxyl, ester, aldehyde, ketone, amine, hydroxyl, amide, alkyl, alkenyl, alkynyl, or aryl; and p can be 0, 1, 2, 3, 4, or 5.

In some embodiments, $R^2$ can be selected from nitro, haloalkyl, cyano, sulfonate, carboxyl, ester, aldehyde, ketone, heteroaryl, heterocyclyl, or $N(R^5)_3{}^+$ wherein each $R^5$ independently is selected from hydrogen, alkyl, aryl, alkenyl, alkynyl, or combinations thereof.

In some disclosed embodiments, ring A can be selected from a 5- or 6-membered heteroaryl or 5- or 6-membered heterocyclyl. For example, in some embodiments ring A can be a 5-membered heteroaryl or heterocyclyl selected from pyrrole, furan, thiophene, pyrazole, oxazole, oxadiazole, thiazole, thiadiazole, triazole, furazan. In particular disclosed embodiments, ring A can be a 6-membered heteroaryl or heterocyclyl, such as diazine, oxazine, thiazine, pyridine, pyrazine, or pyridazine. Some embodiments of the disclosed compounds can comprise a ring A that is selected from any one of Formulas 4, 5, or 6.

Formula 4

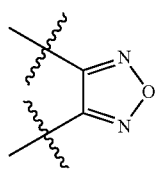

Formula 5

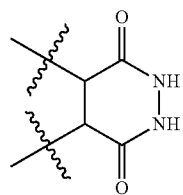

Formula 6

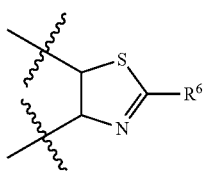

wherein $R^6$ can be a heterocyclyl or a heteroaryl, such as a pyrrole, furan, thiophene, pyrazole, oxazole, oxadiazole, thiazole, thiadiazole, triazole, furazan.

Combinations comprising, consisting essentially of, or consisting of the $H_2S$-reactive compounds are described herein. In some embodiments, combinations can comprise, consist essentially of, or consist of one or more of the $H_2S$-reactive compounds and a sample, such as a biological sample and/or environmental sample, and an optional solvent or aqueous solution. In particular disclosed embodiments, the combination can comprise a colorimetric compound precursor as disclosed herein and a cell, tissue, bodily fluid, a water sample, a soil sample, a gas sample, a plant sample, an air sample or combinations thereof.

A. Colorimetric Testing

Certain method embodiments concern using colorimetric testing for determining whether or not $H_2S$ is present and/or determining the amount of $H_2S$ present in biological (in vivo and/or in vitro) and/or environmental samples. The disclosed colorimetric testing methods can be used to selectively determine the presence of $H_2S$ in the presence of high concentrations of other biologically-relevant nucleophiles, such as GSH, cysteine, and the like. The disclosed colorimetric testing methods utilize sensitive and selective colorimetric compound precursors capable of reacting with $H_2S$, without reacting with, or substantially without reacting with, the other biologically relevant nucleophiles. Without being limited to a particular theory of operation, it is currently believed that in some embodiments, colorimetric testing and/or detection involves a nucleophilic aromatic substitution reaction of $H_2S$ with electron-poor aromatic electrophilic compounds that do not react with thiol-containing compounds.

Conventional and/or currently available colorimetric testing methods used in the art are unable to differentiate thiols from $H_2S$. For example, nucleophile-based methods known in the art are not as effective in determining the presence of $H_2S$ as the methods disclosed herein because the methods currently used in the art involve irreversible probe deactivation upon reaction with thiols thereby preventing further reactions with $H_2S$. Other methods used in the art utilize $H_2S$ as a reductant; however, the amine products made with such reduction methods are identical to thiol-mediated reduction products and therefore it can be complicated to differentiate, detect and/or quantify the $H_2S$-mediated products. Additionally, the present methods using colorimetric testing provide results with unassisted visual detection making these methods viable for high throughput detection and quantification in biological media or homogenates, and for providing access to simple testing methods for applications in which instrumentation or laboratory costs are often prohibitive or otherwise unavailable.

1. Compounds for Colorimetric Testing

In some embodiments, $H_2S$-reactive compounds used in the disclosed colorimetric testing methods are colorimetric compound precursors having a Formula 1 as provided herein, wherein $R^1$ can be Cl, an ether having a Formula 3, or a thioether having Formula 2; $R^2$ is $NO_2$; n is 1; and ring A is a furazan, a thiadiazole, or a triazole. In some embodiments, the colorimetric compound precursors can have a Formula 7, illustrated below, wherein X is oxygen or sulfur and $R^4$, when present, is fluoro, methoxy, or nitro.

Formula 7

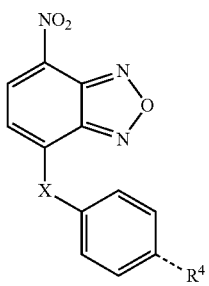

In some embodiments, colorimetric compound precursors for use in the disclosed colorimetric testing methods disclosed herein can be selected from any of the colorimetric compound precursors provided in Table 1.
TABLE 1
Colorimetric Compound Precursor Embodiments
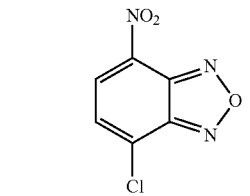
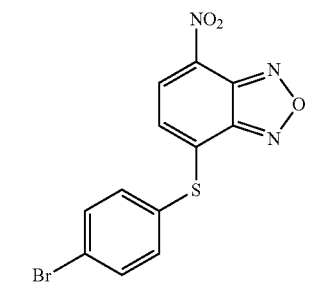
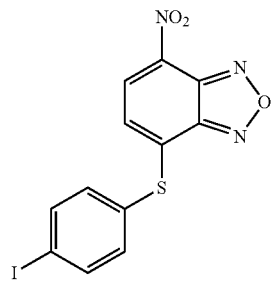 [SMILES: O=[N+]([O-])c1ccc(Sc2ccc(I)cc2)c2nonc12]
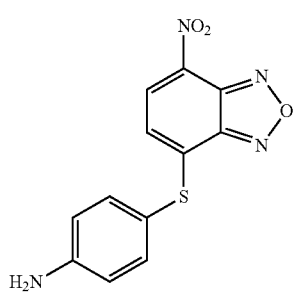
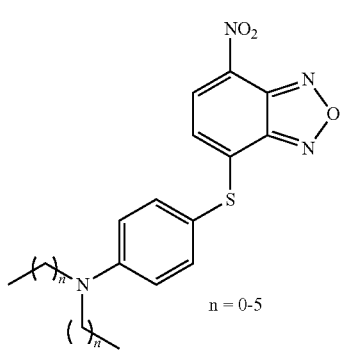
n = 0-5
TABLE 1-continued
Colorimetric Compound Precursor Embodiments
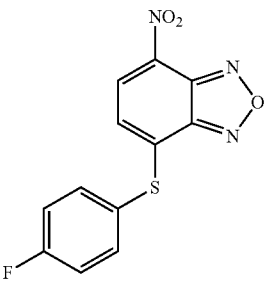
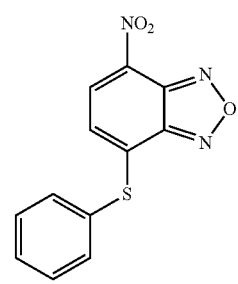 [SMILES: O=[N+]([O-])c1ccc(Sc2ccccc2)c2nonc12]
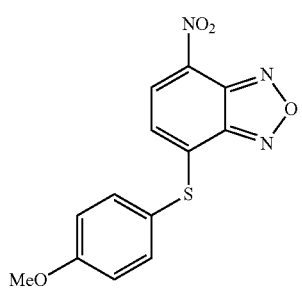 [SMILES: COc1ccc(Sc2ccc([N+](=O)[O-])c3nonc23)cc1]
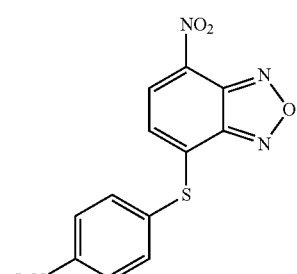
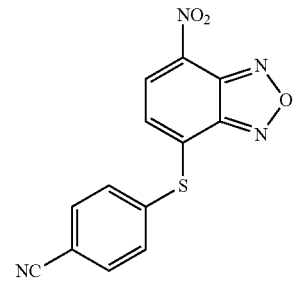

TABLE 1-continued
Colorimetric Compound Precursor Embodiments
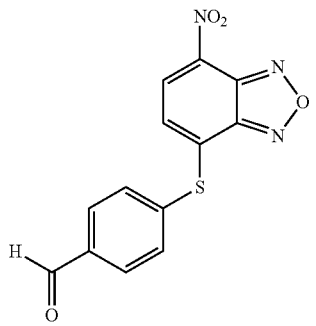
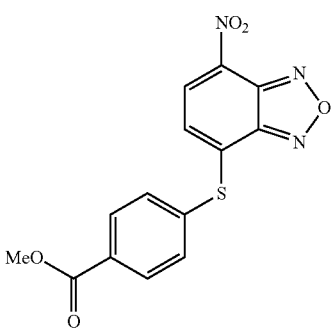
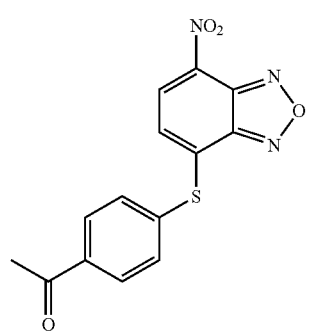 [SMILES: CC(=O)c1ccc(Sc2ccc([N+](=O)[O-])c3nonc23)cc1]
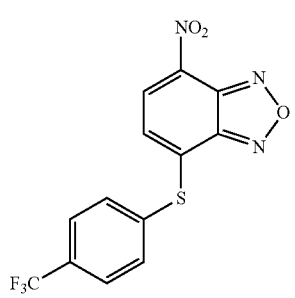 [SMILES: O=[N+]([O-])c1ccc(Sc2ccc(C(F)(F)F)cc2)c2nonc12]
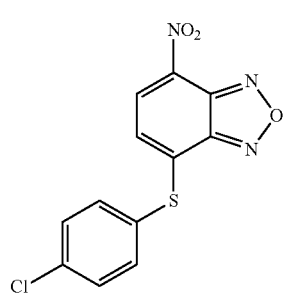 [SMILES: O=[N+]([O-])c1ccc(Sc2ccc(Cl)cc2)c2nonc12]
TABLE 1-continued
Colorimetric Compound Precursor Embodiments
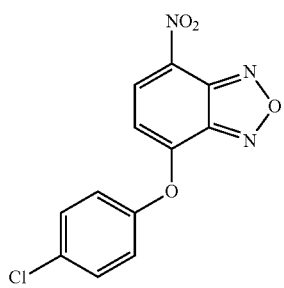 [SMILES: O=[N+]([O-])c1ccc(Oc2ccc(Cl)cc2)c2nonc12]
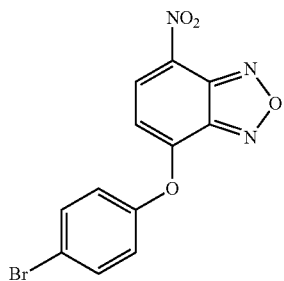
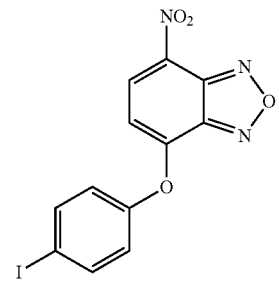
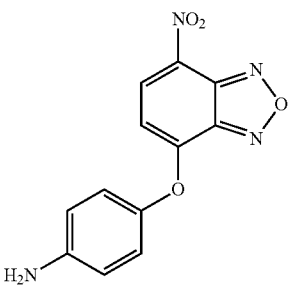
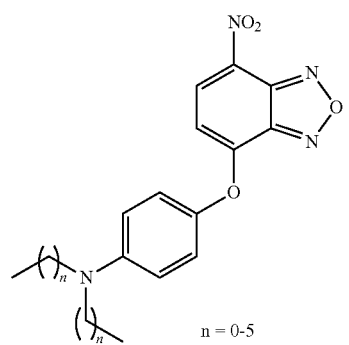
n = 0-5

TABLE 1-continued
Colorimetric Compound Precursor Embodiments
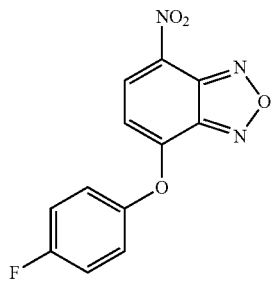
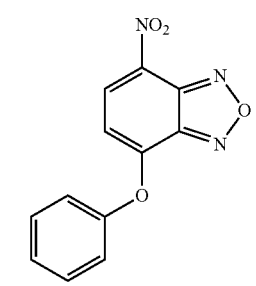
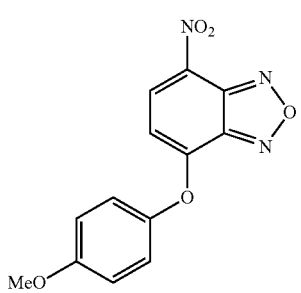
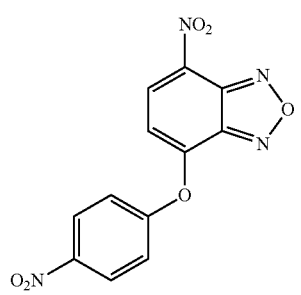 [SMILES: O=[N+]([O-])c1ccc(Oc2ccc([N+](=O)[O-])c3nonc23)cc1]
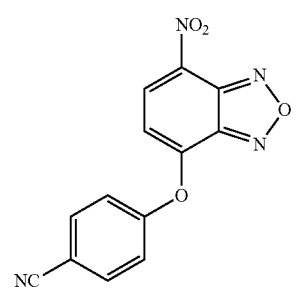 [SMILES: N#Cc1ccc(Oc2ccc([N+](=O)[O-])c3nonc23)cc1]
TABLE 1-continued
Colorimetric Compound Precursor Embodiments
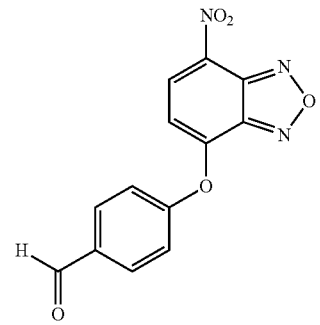 [SMILES: O=Cc1ccc(Oc2ccc([N+](=O)[O-])c3nonc23)cc1]
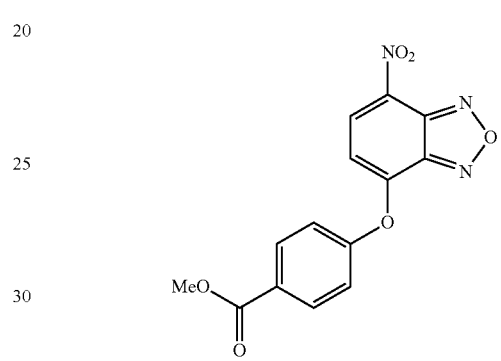
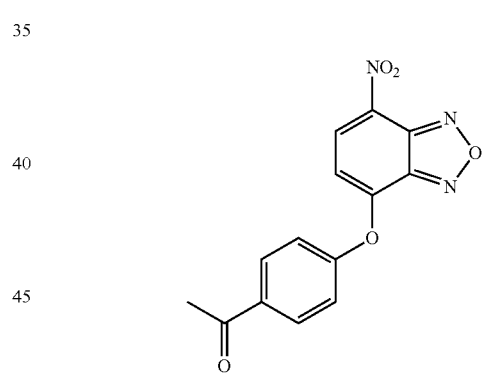
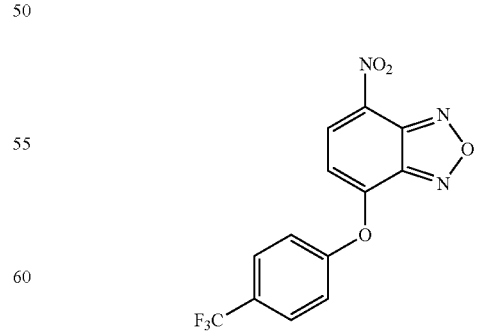
In an independent embodiment, the colorimetric compound precursor can be one of the colorimetric compound precursors provided below.

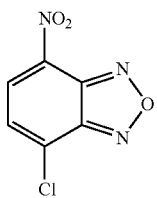
100

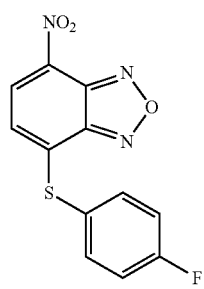
110

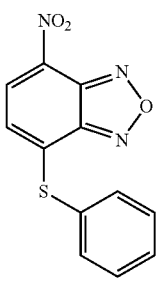
112

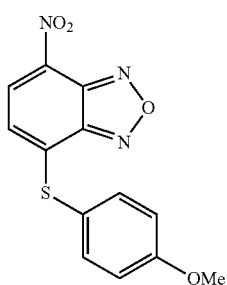
114

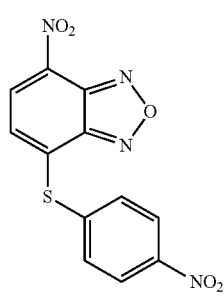
116

Also disclosed herein are compositions of such colorimetric compound precursors. In some embodiments, the disclosed compositions can comprise, consist essentially of, or consist of one or more of the colorimetric compound precursors disclosed above in combination with a solvent (organic or aqueous), a buffer, a carrier, or combinations thereof. In some embodiments, the composition comprises, consists essentially of, or consists of one or more of the disclosed compounds in combination with a solvent, such as water, dimethylsulfoxide, dimethylformamide, dimethylacetamide, acetonitrile, methanol, ethanol, (or other alcohols), dichloromethane, chloroform, and combinations thereof. In some embodiments, the composition can include a concentration of the colorimetric compound precursor ranging from greater than 0 to at least 1M, such as 10 nM to 1M, or 10 nM to 10 µM, or 1 µM to 1 mM, or 100 µM to 1M.

2. Methods of Making Colorimetric Compound Precursors

In some embodiments, the colorimetric compound precursors disclosed herein can be made using the method illustrated in Scheme 1. According to Scheme 1, compound 10 comprises a suitable leaving group ("LG"), such as a halogen, mesylate, besylate, tosylate, or a triflate. Compound 10 can be reacted with an $R^1$-containing nucleophile formed by reacting compound 12 and a base, such as potassium carbonate. The $R^1$-containing nucleophile can react with compound 10 to provide product 14.

Scheme 1

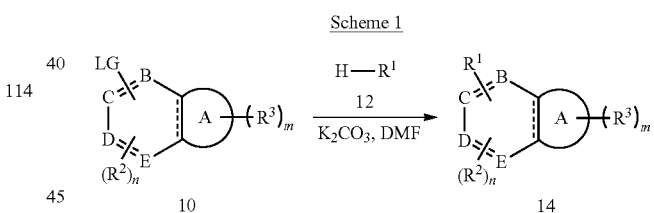

An exemplary embodiment of a method of making colorimetric compound precursors for use in the disclosed colorimetric testing methods is provided in Scheme 2.

Scheme 2

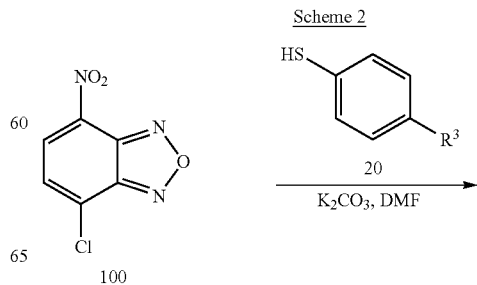

-continued

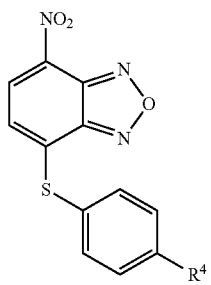

R⁴ = H (112) 76%, F (110) 45%, OMe (114) 46%, NO₂ (116) 64%

3. Methods for Colorimetric Testing

In some embodiments of the disclosed colorimetric testing methods, the method comprises providing a colorimetric compound precursor (or composition thereof) for testing for the presence of $H_2S$ in a biological and/or environmental sample. In some embodiments, the colorimetric compound precursors are capable of producing a color change if $H_2S$ is present in a sample. Certain embodiments comprise, consist essentially of, or consist of exposing a sample to an effective amount of one or more of the colorimetric compound precursors (or composition thereof) and analyzing the sample for a color change produced by a reaction between the colorimetric compound precursor and any $H_2S$ present in the sample.

In some embodiments, the colorimetric compound precursors can be provided neat or they can be provided as a composition. In particular disclosed embodiments, the colorimetric compound precursor provided in the method is selected to have a particular reactivity with $H_2S$. For example, as illustrated in Scheme 3, below, the colorimetric compound precursor can be an electrophilic aryl compound 30 capable of reacting with $H_2S$ to make a visually detectable thiophenol 32. If this compound were to react with a thiol, such as a biologically active thiol like GSH, the resulting product would be thioether 34. Unless the resulting thioether is sufficiently electrophilic, it will not further react with $H_2S$ to generate the visually detectable thiophenol product 32. Thioethers generated from a reaction between a biologically active thiol, such as glutathione, typically lack the electrophilicity to be converted to detectable thiophenol product 32. Colorimetric compound precursors disclosed herein, particularly colorimetric compound precursors 110-116, however, are suitably electrophilic so as to be capable of reacting with $H_2S$ to form a thiophenol product. Accordingly, selecting the colorimetric compound precursors meeting Formula 7, disclosed above, allows for thiol attack of the colorimetric compound precursor without compromising reactivity toward $H_2S$, thus creating a thiol-insensitive platform for $H_2S$ detection.

Scheme 3

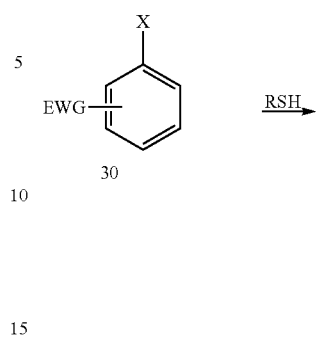

In some embodiments, the colorimetric compound precursor can meet Formula 1 wherein $R^1$ is halogen (e.g., Cl) to thereby provide a product, such as any one of the colorimetric compound precursors meeting Formula 7. This product can react irreversibly with $H_2S$ and also has different photophysical properties from the thiolphenol. Accordingly, in embodiments wherein the colorimetric compound precursor reacts with $H_2S$ present in the sample, a color change will occur. In exemplary embodiments, the color change produces a color where no color was previously observed, or it can result in color shift from one color to another color. Furthermore, a person of ordinary skill in the art would recognize a color change has occurred. In other embodiments wherein the colorimetric compound precursor does not react with $H_2S$ because it is not present, or not present at a detectable limit, a color change does not occur.

Figure 2:
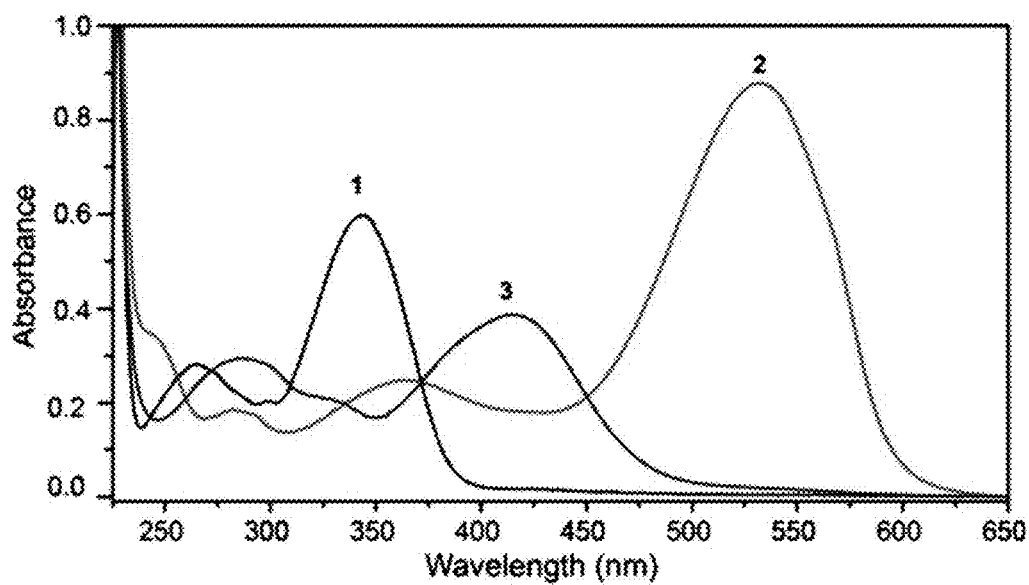
FIG. 2 is a UV-visible spectrum of an $H_2S$-reactive compound embodiment disclosed herein (peak 1), an intermediate compound formed from reacting the $H_2S$-reactive compound with NaSH (peak 3), an $H_2S$ donor, as well as a thiolphenol compound (peak 2) obtained from the reaction between the $H_2S$-reactive compound and NaSH.

An exemplary embodiment illustrating colorimetric compound precursor 100 and its reactivity with $H_2S$ is illustrated in Scheme 4, below. In some embodiments of the disclosed colorimetric testing methods, colorimetric compound precursor 100 undergoes a nucleophilic aromatic substitution reaction with $H_2S$ to produce thiolphenol 42, thereby producing a color change. Thiolphenol 42 produces an absorbance peak at 530 nm to 540 nm and thereby exhibits a red color, which can be visually detected. Detecting or observing the color change does not require instrumentation, such as a UV-vis spectrometer, as it is visible to the naked eye. For example, as illustrated in FIG. 1, the conversion of colorimetric compound precursor 100 to thiolphenol 42 provides a color change as the color of a solution of colorimetric compound precursor 100 changes from yellow (e.g., absorbing light at a wavelength of 343 nm) to red (e.g., absorbing light at a wavelength of 534 nm). As illustrated in Scheme 4, treatment of colorimetric compound precursor 100 with sub-stoichiometric H₂S can form a mixture of thioether 40 and thiolphenol 42. The UV-visible spectrum illustrated in FIG. 2 illustrates a mixture of compound 100 (peak 1), thioether 40 (peak 3), and thiolphenol 42 (peak 2). The mixture can be converted to thiolphenol 40 using stoichiometric amounts of H₂S. Thioether 40 can also react with H₂S to generate thiolphenol 40 and thioether 112. Thus colorimetric compound precursor 100 provides a specific reactivity with H₂S that provides the ability to visually observe a color change even in embodiments wherein a thioether product is formed, such as thioether 112 or thioether 40.

Scheme 5

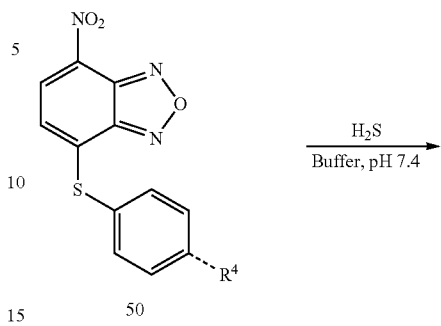

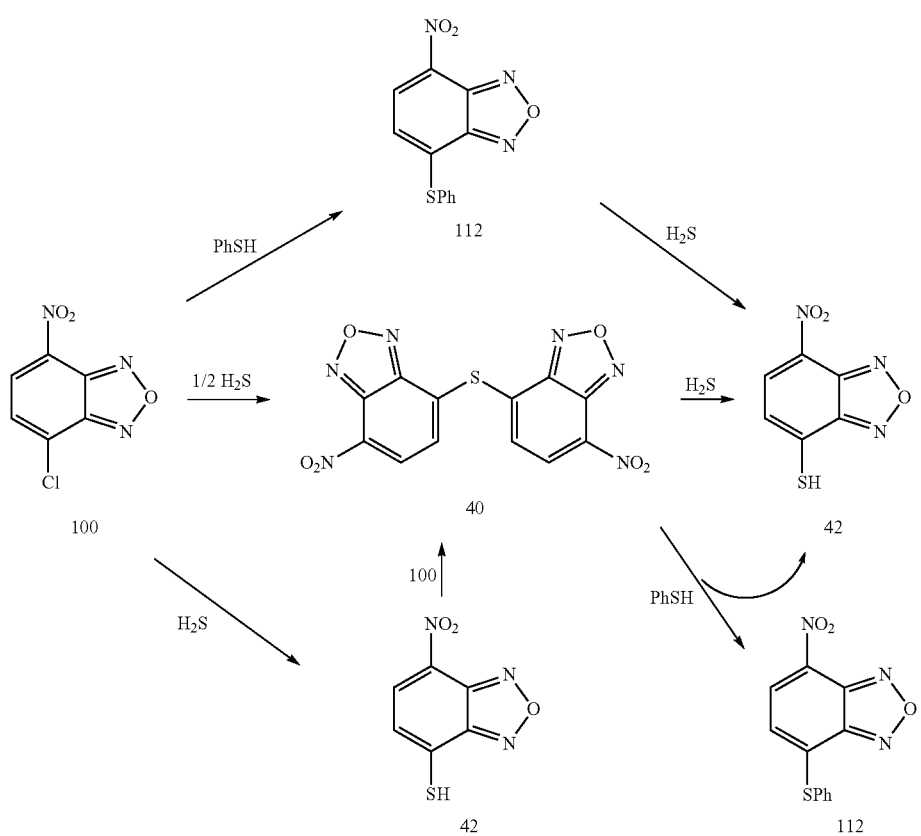

Scheme 4

In other disclosed embodiments, the method can comprise, consist essentially of, or consist of using colorimetric compound precursors like compounds 100 or 110-116 to generate the thiolphenol 42. These colorimetric compound precursors contain functional groups that promote the colorimetric compound precursors' electrophilicity thereby making them suitable for the colorimetric testing methods disclosed herein as they react selectively and irreversibly with H₂S. A particular embodiment of the reaction between H₂S and exemplary colorimetric compound precursors is illustrated in Scheme 5, below. According to Scheme 5, thioether 50 or ether 52 reacts with H₂S to provide the thiolphenol 42 and a thiol by-product 54 or phenol by-product 56. Without being limited to a single theory of operation, it is currently believed that thiolphenol 42 is produced by a nucleophilic aromatic substitution reaction between H₂S and thioether 50 or ether 52.

-continued

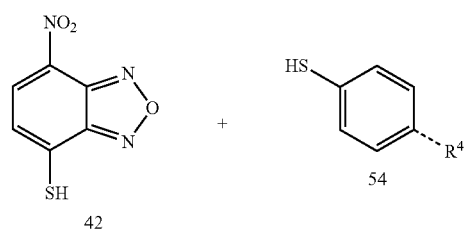

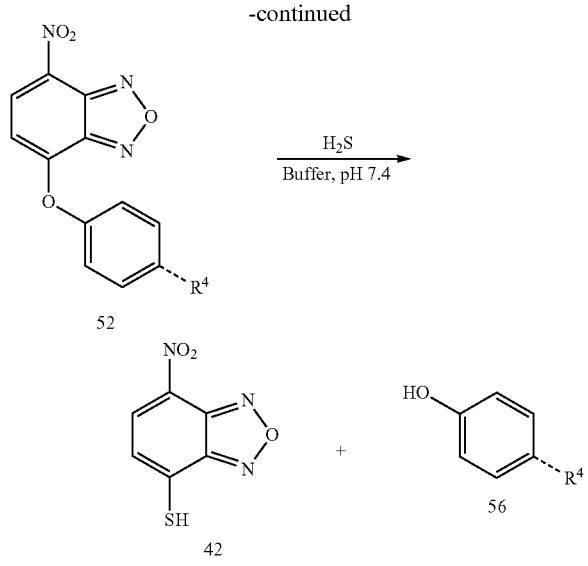

$R^4 = F, NO_2, OMe$

Some embodiments of the disclosed methods can comprise, consist essentially of, or consist of exposing a sample to one or more of the colorimetric compound precursors disclosed herein, such as those meeting Formula 7, particularly any one of colorimetric compound precursors 100 or 110-116. In some embodiments, the colorimetric compound precursors, or compositions thereof, can be provided in one or more wells of a multi-well plate, on the surface of a substrate, in a filter, or combinations thereof, to which the sample is added. In other embodiments, the sample can be provided in one or more wells of a multiwell plate, on the surface of a substrate, in a filter, or combinations thereof, to which the colorimetric compound precursor or composition is added. In some embodiments, the sample is exposed to an effective amount of the colorimetric compound precursor. Such effective amounts can be any amount of the colorimetric compound precursor that is sufficient to react with greater than 0 to at least 100 μM 150 nM to 100 μM $H_2S$, such as 200 nM to 100 μM $H_2S$, or 200 nM to 1 μM $H_2S$, or 1 μM to 100 μM $H_2S$, or 1 μM to 10 μM $H_2S$ present in the sample such that the $H_2S$ can react with the colorimetric compound precursor, if present, to produce a color change. In some embodiments, the effective amount of the colorimetric compound precursors may range from greater than 0 to at least 1M, such as from 100 nM to 1M, or 1 μM to 100 μM, or 5 μM to 10 μM.

The sample can be exposed to the colorimetric compound precursor (or composition thereof) for a time sufficient to produce a color change as disclosed herein. In some embodiments, the sample can be exposed to the colorimetric compound precursor for greater than 0 seconds to at least 60 minutes, such as 30 seconds to 60 minutes, or 1 minute to 10 minutes, or 2 minutes to 5 minutes.

In some embodiments, the sample is exposed to the colorimetric compound precursor (or composition thereof) at a particular temperature that does not substantially prohibit the reaction between the colorimetric compound precursor and $H_2S$, to the extent that any $H_2S$ present in the sample does not react with the colorimetric compound precursor to provide a color change. In some embodiments, the temperature can range from −20° C. to 80° C., such as 25° C. to 37° C., or 5° C. to 10° C. Additionally, the sample can be exposed to the colorimetric compound precursor at a pH that can promote a reaction between the colorimetric compound precursor and any $H_2S$ present in the sample and/or maintain the integrity of the particular sample being analyzed. For example, in some embodiments, the sample may be a biological sample and therefore should be maintained at a biological pH. In some embodiments, the pH can be adjusted to or maintained at a pH of 3 to 12, such as from 6 to 9, or 7 to 7.4.

In some embodiments of the colorimetric testing methods, a color change produced by a reaction between the colorimetric compound precursor and $H_2S$ is detected. In some embodiments, the color change that produces colored light having a wavelength within the visible range of the electromagnetic spectrum, such as 380 nm to 790 nm. In some embodiments, the color change results in a color selected from red (e.g., wavelengths between 620 nm to at least 740 nm, which can correspond to an absorbance of 490 nm to 570 nm); orange (e.g., wavelengths between 585 nm to 620 nm, which can correspond to an absorbance of 440 nm to 490 nm); yellow (e.g., wavelengths between 570 nm to 585 nm, which can correspond to an absorbance of 400 nm to 430 nm); green (e.g., wavelengths between 490 nm to 570 nm, which can correspond to an absorbance of 620 nm to 740 nm); blue (e.g., wavelengths between 440 nm to 490 nm, which can correspond to an absorbance of 585 nm to 620 nm); indigo (e.g., wavelengths between 420 nm to 440 nm, which can correspond to an absorbance of 580 nm to 590 nm); violet (e.g., wavelengths between 400 nm to 420 nm, which can correspond to an absorbance of 570 nm to 580 nm); or any combination thereof.

In some embodiments, colorimetric testing methods can be used to obtain low detection limits of $H_2S$ in samples. For example, low detection limits obtained with the disclosed method can range from greater than 0 to at least 100 μM, such as 150 nM to 100 μM, or 150 nM to 490 nM, or 150 nM to 480 nM, or from 150 nM to 470 nM. In an independent embodiment, the low detection limit can range from 180 (±30) nM to 450 (±40) nM.

Figure 3:
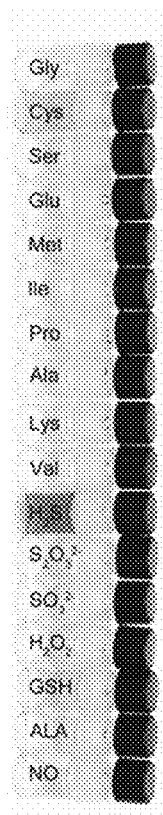
FIG. 3 is a digital image showing a color change obtained by exposing different samples to an $H_2S$-reactive compound embodiment disclosed herein.
Figure 4A:
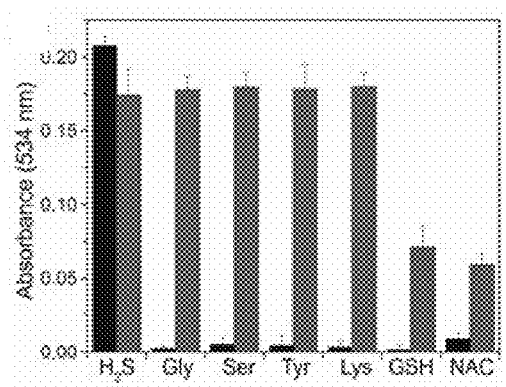
FIGS. 4A and 4B are graphs illustrating the color change (absorbance at 534 nm) obtained by treating nucleophilic thiols with $H_2S$-reactive compound embodiments disclosed herein.
Figure 4B:
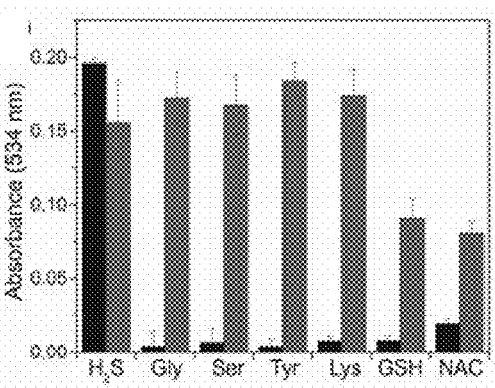

The disclosed colorimetric testing methods, unlike colorimetric methods currently used in the art, are selective for $H_2S$ over other active thiol-containing compounds, sulfur species, oxygen species, and nitrogen species, such as glycine, cysteine, serine, glutamic acid, methionine, isoleucine, proline, alanine, lysine, valine, NaSH (an $H_2S$ donor), $Na_2S_2O_3$, $Na_2SO_3$, glutathione (GSH), $H_2O_2$, lipoic acid, S-nitroso-N-acetyl-DL-penicillamine. For example, FIG. 3 illustrates results obtained from embodiments wherein compounds disclosed herein were treated with 50 equivalents of different amino acids or reactive sulfur, oxygen, or nitrogen species. As illustrated in FIG. 3, only colorimetric compound precursor embodiments exposed to $H_2S$ provided a detectable signal (e.g., the reddish color provided in the vial labeled "$H_2S$" in FIG. 3) absorbing light at a wavelength of 534. The yellow colors exhibited in vials labeled "Cys" and "GSH" corresponds to the formation of thioether products. Additionally, FIGS. 4A and 4B illustrate results obtained from using an embodiment of the colorimetric testing methods disclosed herein and particular colorimetric compound precursor embodiments to selectively detect $H_2S$ over other biologically-relevant nucleophiles, such as glycine, serine, tyrosine, lysine, glutathione, and N-acetyl-L-cysteine. FIGS. 4A and 4B illustrate that only the colorimetric compound precursors embodiments that had reacted with $H_2S$, versus the nucleophiles, produced a significant absorbance peak at 534 nm. These results demonstrate the sensitivity and efficiency of the disclosed methods, compounds, and compositions thereof.

In some embodiments, the method can further comprise quantifying the amount of $H_2S$ present in the sample. In some embodiments, a relative concentration of $H_2S$ can be determined by analyzing the sample to determine if a color change is produced. In some embodiments, specific concentrations of $H_2S$ can be detected by calculating the concentration using absorbance values obtained from spectroscopic analysis of the reaction between $H_2S$ and the colorimetric compound precursors disclosed herein.

4. Kits for Colorimetric Testing

Also disclosed herein are embodiments of kits for detecting $H_2S$ using colorimetric testing methods disclosed herein. In some embodiments, the kits may comprise, consist essentially of, or consist of a pre-measured amount of the colorimetric compound precursor that can range from greater than 0 to at least 1 g, such as 1 μg to 1 g, or 1 mg to 10 mg, or 0.5 mg to 1 mg.

In some embodiments, the kits can comprise, consist essentially of, or consist of a filter containing one or more of the colorimetric compound precursors, such as any of compounds 110-116. In some embodiments, the filter can be configured to allow a fluid sample to pass through the exterior of the filter so as to contact the colorimetric compound precursor, which may be coupled to a substrate in the form of a powder or thin film. The substrate can be a disc, test strip, or slide contained within the filter. If $H_2S$ is present in the sample, the colorimetric compound precursor will generate a color change that can be visually observed by the user. In some embodiments, the kits can be calibrated for a presence/absence test corresponding to certain $H_2S$ concentration levels, similar to the concentration levels described herein. In some embodiments, the use of any kit components containing different amounts of the colorimetric compound precursors could be used to provide an estimate the concentration of $H_2S$ present in a sample.

In other embodiments, the kits can comprise, consist essentially of, or consist of a well plate comprising, consisting essentially of, or consisting of pre-measured amounts of the colorimetric compound precursor within each well of a multi-well plate. Such kits could be used such that a finite sample volume is loaded into the well or such that a larger sample volume is continuously flowed through the well. Such kits can be used for biological assays utilizing colorimetric testing.

In some embodiments, the kits comprise a substrate (e.g., a paper test strip or disc) comprising, consisting essentially of, or consisting of one or more of the colorimetric compound precursors (or compositions thereof), a test bottle, a color chart, a defoamer, an acid, and/or a base. In some embodiments, the substrates disclosed herein may be coupled to the colorimetric compound precursor such that the colorimetric compound precursor is deposited as a thin film or powder with a suitable binder or adhesive compound that helps to maintain contact between the substrate and the colorimetric compound precursors.

B. Chemiluminescent Testing

Figure 5:
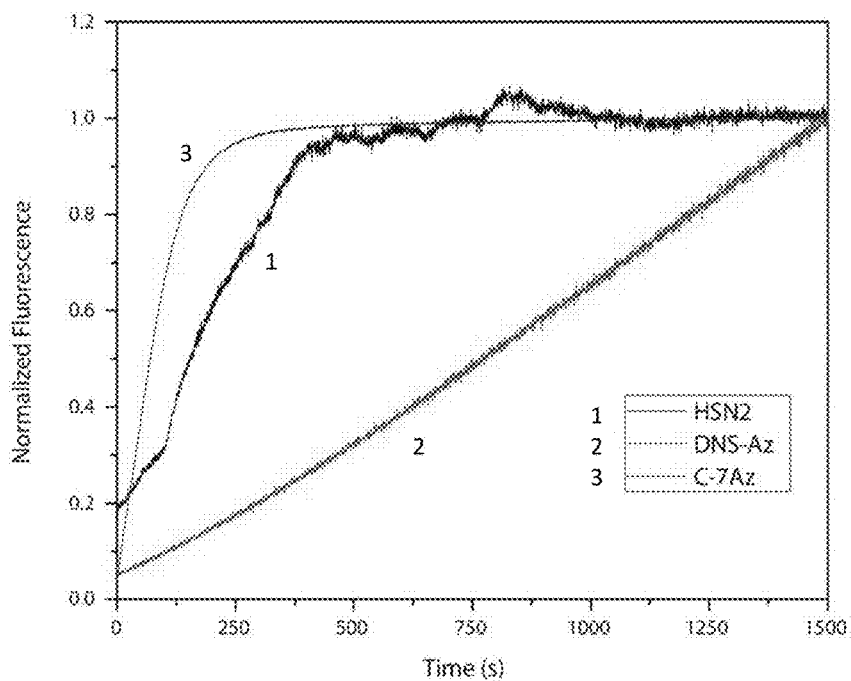
FIG. 5 is a graph of normalized fluorescence versus time (seconds) illustrating photoactivation of different azide-containing compounds known in the art.

Other disclosed embodiments of the disclosed methods for determining the presence of $H_2S$ include chemiluminescent testing methods for determining the presence of $H_2S$. In some embodiments, the chemiluminescent testing methods can comprise, consist essentially of, or consist of quantifying the amount of $H_2S$ present in a particular sample. Conventional methods used in the art for detecting $H_2S$ typically require high-powered excitation sources, such as those associated with confocal microscopy or HPLC detectors, or require extended periods of excitation, such as with azide-containing fluorophores. Although azide-based $H_2S$ probes have been used in the art in combination with epifluorescent or confocal microscopy, continuous exposure of prototypical azide-containing $H_2S$ probes used in the art, such as 2,6-dansyl azide ("DNS-Az"), hydrosulfide naphthalimide ("HSN2"), or 7-azido-4-methylcoumarin ("C-7Az"), results in probe photoactivation (which can deactivate the probe) within minutes. For example, FIG. 5 illustrates photoactivation of HSN, DNS-Az, and C-7Az under fluorescence analysis, thus illustrating that such probes easily degrade upon exposure to the energy produced in fluorescent detection.

Because the chemiluminescent testing methods disclosed herein do not require excitation, photodegredation of the chemiluminescent compound precursors disclosed herein does not occur. Additionally, because biological materials typically do not spontaneously emit light, the chemiluminescent testing methods disclosed herein provide higher signal-to-noise ratios than detection techniques currently used in the art, such as fluorometric detection.

Also, the chemiluminescent testing methods disclosed herein are used to detect $H_2S$, whereas conventional detection methods are not suitable for such testing. For example, conventional reaction-based small-molecule chemiluminescent detection methods used in the art focus on detecting reactive oxygen species, such as $H_2O_2$, and not $H_2S$. Chemiluminescent methods for detecting biological thiols are known in the art; however, these methods exhibit low selectivity for a specific thiol compound and measure the decrease in signal caused by reaction of the analyte with either the luminescent catalyst or the oxidant. In contrast, the presently disclosed chemiluminescent testing methods provide the ability to specifically detect $H_2S$, if present, over other biological thiols while also providing the ability to quantify the amount of $H_2S$ in a sample. The present chemiluminescent methods also do not require the use of instruments for sample analysis as all analysis may be conducted visually. Such methods are useful in situations where the use of analytical instrumentation is impractical, undesired, and/or unavailable. Also, the present chemiluminescent methods allow people with minimal training and/or knowledge of $H_2S$ detection techniques to use the compounds, compositions, and/or kits disclosed herein to determine the presence of $H_2S$ in samples.

1. Compounds for Chemiluminescent Testing $H_2S$-reactive compounds suitable for use in the disclosed chemiluminescent testing methods can be chemiluminescent compound precursors having a Formula 1 as provided herein, wherein $R^1$ is an azide and ring A is a pyridazine comprising two oxo substituents. In some embodiments, $R^2$ may be selected from linker, such as an amide, carboxyl, or alkylene glycol linker, or any combination thereof, which is attached to a fluorophore moiety, such as, but not limited to, coumarin, naphthalimide, fluorescein, rhodamine, rhodol, Cy3, or Cy5. In some embodiments, the chemiluminescent compound precursors can have any one of Formulas 8, 9, or 10, illustrated below.

Formula 8

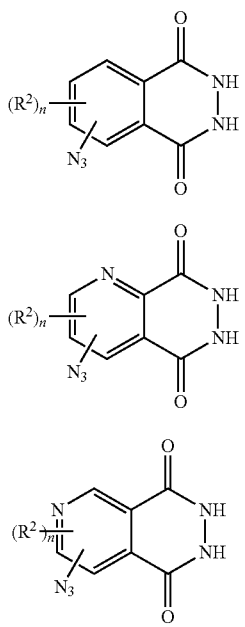

Formula 9

Formula 10

In some embodiments, exemplary chemiluminescent compound precursors for use in the disclosed chemiluminescent testing methods can be selected from the chemiluminescent compound precursors provided in Table 2.

TABLE 2

Exemplary Chemiluminescent Compound Precursors

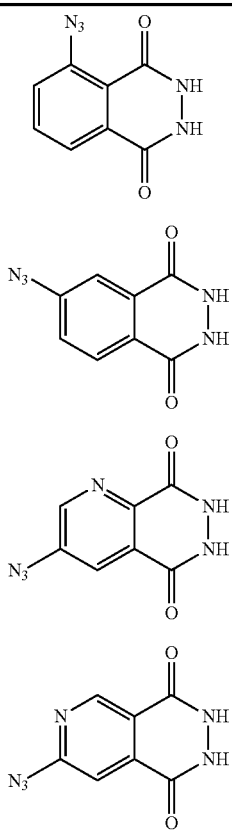

TABLE 2-continued

Exemplary Chemiluminescent Compound Precursors

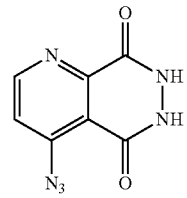

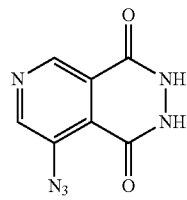

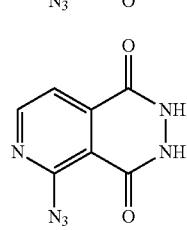

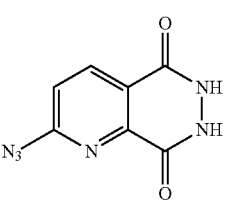 [SMILES: [N-]=[N+]=Nc1ccc2c(=O)[nH][nH]c(=O)c2n1]

Also disclosed herein are compositions of such chemiluminescent compound precursors. In some embodiments, the disclosed compositions can comprise, consist essentially of, or consist of one or more of the chemiluminescent compound precursors disclosed above in combination with a solvent (organic or aqueous), a buffer, a carrier, and combinations thereof. In some embodiments, the composition comprises, consists essentially of, or consists of one or more of the disclosed chemiluminescent compound precursors in combination with a solvent, such as water, dimethylsulfoxide, dimethylformamide, dimethylacetamide, acetonitrile, methanol, ethanol, (or other alcohols), and combinations thereof. In some embodiments, the composition can include a concentration of the chemiluminescent compound precursor ranging from greater than 0 to at least 1M, such as 10 nM to 1 M, or 1 μM to 50 μM, or 10 μM to 20 μM.

In other embodiments, the composition can comprise a chemiluminescent compound precursor embodiment, a means for catalyzing oxidation (such as an enzyme or a transition metal cation), an oxidant, a base, an enhancer, and any combination thereof. In some embodiments, the enzyme can be a peroxidase enzyme, such as horseradish peroxidase, or other heme-iron containing proteins. Alternatively, transition metal cations, such as Fe(II), Ru(II), or Cu(II) can also be used. In some embodiments, the oxidant can be a peroxide, such as $H_2O_2$ or benzoyl peroxide. Other oxidants can be selected from hypochlorite, permanganate, ferricyanide, periodate, or N-bromosuccinimide. In yet additional embodiments, the composition can further comprise an enhancer that enhances the brightness and lifetime of the chemiluminescence emitted by the chemiluminescent compound. Suitable enhancers include phenolic compounds, such as p-iodophenol, t-butyl phenol, 4-chloro-3-methyl phenol, phenyloxyphenol, methylphenol, benzylphenol, phenol, 4-hydroxycinnamic acid, fluorophenol, phenylazophenol, chlorophenol, bromophenol, 4-hydroxybenzoic acid and benzoates, 4-hydroxy phenones, 4-hydroxy benzaldehyde, and 4-hydroxybenzonitrile. A base also can be used to provide a basic pH environment (e.g., a pH of 8 to 12, such as 8 to 11, or 8 to 10). Suitable bases include, but are not limited to, hydroxides, such as sodium hydroxide, lithium hydroxide, potassium hydroxide; or carbonates, such as calcium carbonate, sodium carbonate, cesium carbonate, and the like.

2. Methods of Making Chemiluminescent Compound Precursors

In some embodiments, the chemiluminescent compound precursors disclosed herein can be made according to, for example, Scheme 6. In some embodiments, a starting compound, such as amine 60, can be converted to a corresponding azide 62 using suitable reagents, such as tert-butyl nitrite (t-BuONO) and azidotrimethylsilane (TMS-N$_3$) in DMSO.

Scheme 6

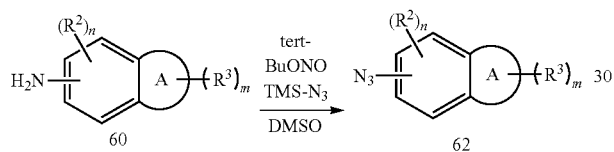

An exemplary method for making embodiments of the chemiluminescent compound precursors is illustrated in Scheme 7. In this particular embodiment, amine 70 is converted to azide 72 using tert-butyl nitrite and azidotrimethylsilane in dimethylsulfoxide.

Scheme 7

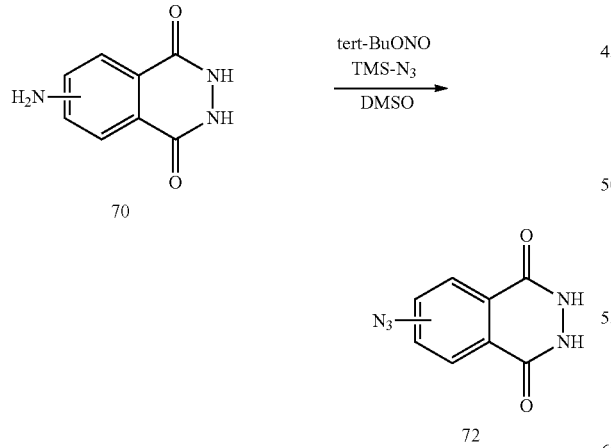

3. Methods for Chemiluminescent Testing

In some embodiments of the disclosed chemiluminescent testing methods, the method can comprise, consist essentially of, or consist of exposing a sample to one or more of the chemiluminescent compound precursors disclosed herein, or compositions thereof; exposing the sample to an oxidant, an enzyme, and/or an enhancer, in any order; and determining the presence of H$_2$S, such as by visually analyzing the sample for a color change, such as chemiluminescence, that is produced from a reaction product obtained from reaction of the chemiluminescent compound precursor and H$_2$S. In some embodiments, the H$_2$S reacts with the chemiluminescent compound precursor to convert an azide moiety of the chemiluminescent compound precursor to an amine moiety. The amine-containing reaction product is thereby able to produce chemiluminescence once it undergoes a further chemical modification. In some embodiments the chemiluminescent testing methods also includes exposing the sample to a means for oxidizing the amine-containing compound to a compound that emits chemiluminescence. In some embodiments, the means for oxidizing the amine-containing compound can be an oxidant or an oxidant used in combination with an enzyme and a base. In yet additional embodiments, a means for intensifying and prolonging the duration of the chemiluminescence emitted from the amine-containing compound can be used, such as an enhancer compound as disclosed above.

Exemplary embodiments concern exposing an azide-containing luminol compound to a sample; exposing the sample to H$_2$O$_2$, horseradish peroxidase, sodium hydroxide, and analyzing the sample for chemiluminescence emitted from a reaction product of the reaction between the azide-containing luminol compound and H$_2$S, if H$_2$S is present in the sample.

According to Scheme 8, an embodiment of the disclosed chemiluminescent compound precursors, azide 80, is reacted with H$_2$S under suitable reaction conditions (e.g., pH of 7.4). Azide 80 comprises a reactive azide moiety that can be reduced when exposed to H$_2$S. For example, the azide moiety can be converted to an amine moiety after reaction with the H$_2$S. The resulting amine-containing compound 82 can then undergo oxidation to provide product 84, which can produce luminescence. The ability to visually detect this signal is a consequence of the presence of H$_2$S.

Scheme 8

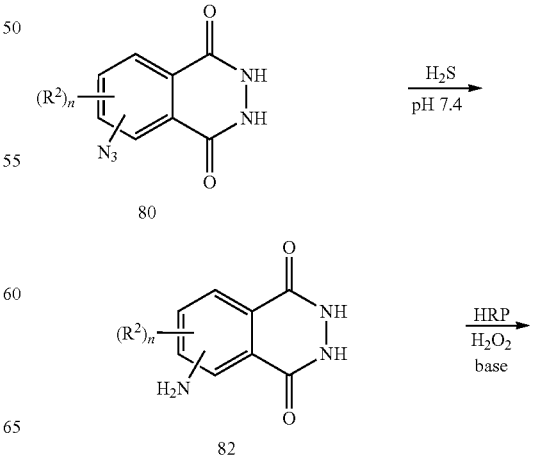

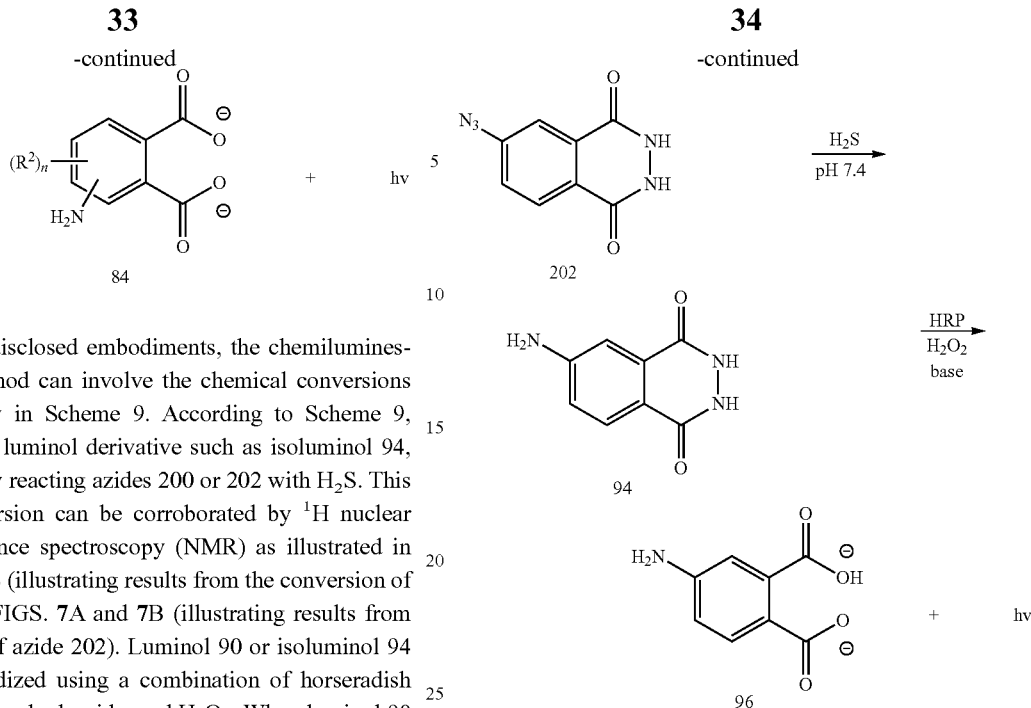

Figure 6A:
FIGS. 6A and 6B are $^1$H nuclear magnetic resonance (NMR) spectra of an $H_2S$-reactive compound embodiment before (FIG. 6B) and 90 minutes after (FIG. 6A) reaction with $H_2S$.
Figure 6B:
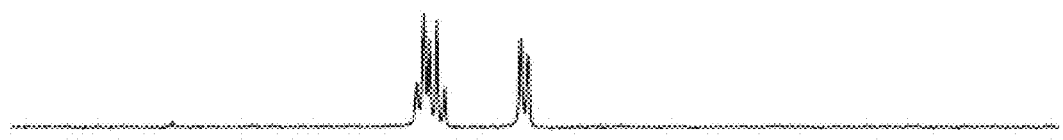
Figure 7A:
FIGS. 7A and 7B are a $^1$H NMR spectra of an $H_2S$-reactive compound embodiment before (FIG. 7B) and 10 minutes after (FIG. 7A) reaction with $H_2S$.
Figure 7B:
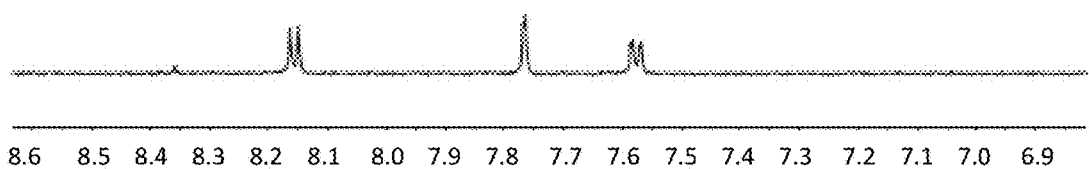

In particular disclosed embodiments, the chemiluminescent testing method can involve the chemical conversions illustrated below in Scheme 9. According to Scheme 9, luminol 90, or a luminol derivative such as isoluminol 94, can be formed by reacting azides 200 or 202 with $H_2S$. This particular conversion can be corroborated by $^1H$ nuclear magnetic resonance spectroscopy (NMR) as illustrated in FIGS. 6A and 6B (illustrating results from the conversion of azide 200) and FIGS. 7A and 7B (illustrating results from the conversion of azide 202). Luminol 90 or isoluminol 94 can then be oxidized using a combination of horseradish peroxidase, sodium hydroxide, and $H_2O_2$. When luminol 90 or isoluminol 94 are oxidized, these compounds are converted to transient singlet carbonyl species that then decompose to phthalate-containing products. Concomitant $N_2$ extrusion then provides detectable products 92 and 96, respectively. Products 92 and 96 exhibit luminescence at 425 nm, which can be visually observed, typically in the dark. In particular disclosed embodiments, the progress of the reaction between $H_2S$ and the chemiluminescent compound precursor can be monitored using $^1H$ NMR spectroscopy.

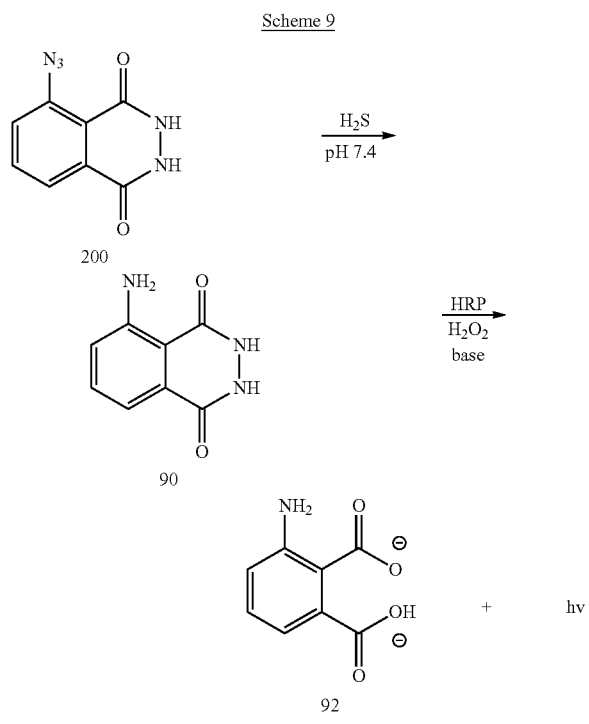

In some embodiments, the sample is exposed to an effective amount of the chemiluminescent compound precursor using any of the techniques described herein. Such effective amounts can be any amount of the chemiluminescent compound precursor that is sufficient to react with greater than 0 to at least 1M $H_2S$, such as 50 nM to 1 M $H_2S$, or 1 μM to 100 μM $H_2S$, or 5 μM to 20 μM $H_2S$ present in the sample such that the $H_2S$ can react with the chemiluminescent compound precursor, if present, to produce a color change, such as chemiluminescence. A person of ordinary skill in the art would recognize a color change has occurred. In some embodiments, the effective amount of the chemiluminescent compound precursors can range from greater than 0 to at least 1 g, such as 1 μg to 1 g, or 1 mg to 100 mg, or 5 mg to 10 mg.

The sample can be exposed to the chemiluminescent compound precursor (or composition thereof) for a time sufficient to produce a color change, such as chemiluminescence. In some embodiments, the sample can be exposed to the chemiluminescent compound precursor (or composition thereof) for greater than 0 to at least 120 minutes, such as 1 minute to 120 minutes, or 30 minutes to 90 minutes, or 5 minutes to 10 minutes.

In some embodiments, the sample is exposed to the chemiluminescent compound precursor (or composition thereof) at a particular temperature that does not substantially prohibit the reaction between the chemiluminescent compound precursor and $H_2S$, to the extent that any $H_2S$ present in the sample does not react with the chemiluminescent compound precursor to ultimately provide a color change, such as chemiluminescence. In some embodiments, the temperature can range from −20° C. to 80° C., such as from 25° C. to 37° C., or 22° C. to 25° C. Additionally, the sample can be exposed to the chemiluminescent compound precursor at a pH that can promote a reaction between the chemiluminescent compound precursor and any $H_2S$ present in the sample, maintain the integrity of the particular sample being analyzed, and/or allow oxidation using an oxidant, enzyme, enhancer, or combination thereof. For example, in some embodiments, the sample may be a biological sample and therefore should be maintained at a biological pH. In some embodiments, the pH can be adjusted to or maintained at a pH of 5 to 12, such as from 8 to 11, or 10 to 10.5.

Figure 8:
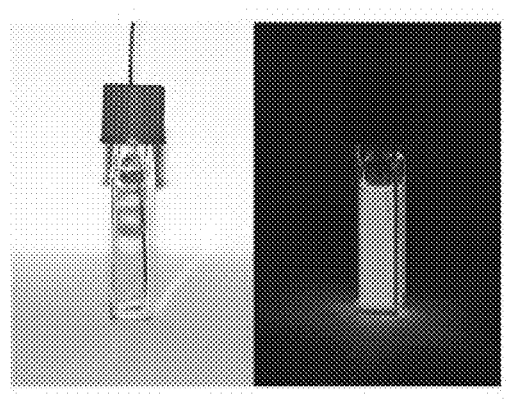
FIG. 8 is a digital image showing chemiluminescence of a disclosed $H_2S$-reactive compound embodiment after exposure to $H_2S$.
Figure 9:
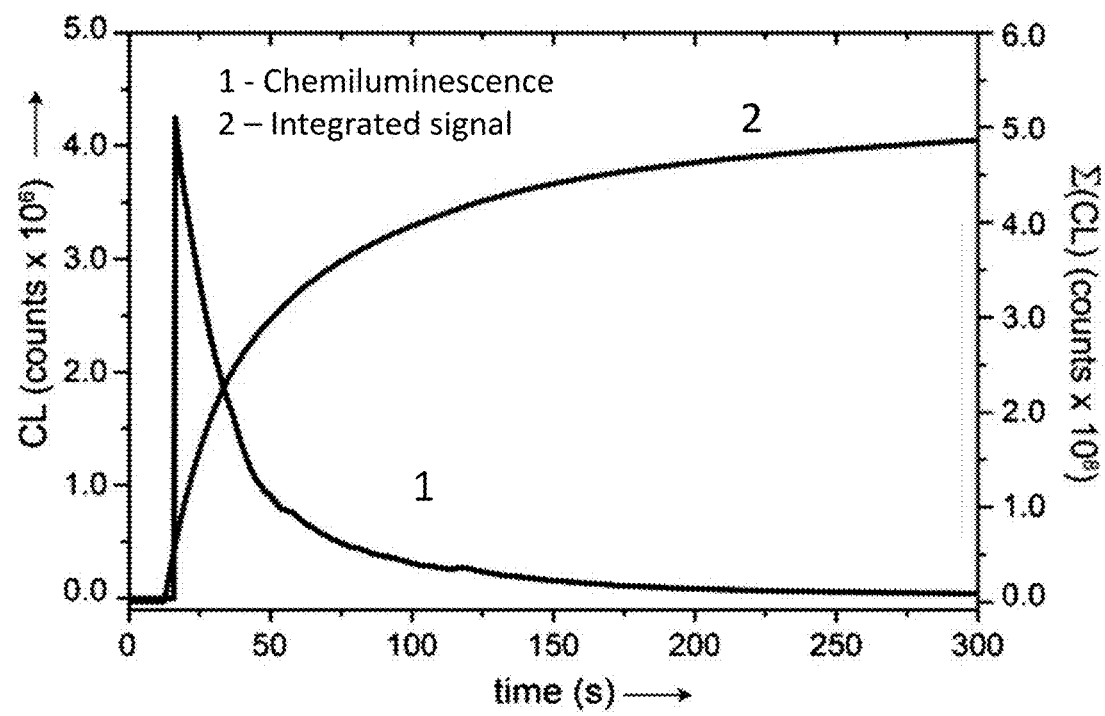
FIG. 9 is a graph of chemiluminescence (counts×$10^6$) versus time (seconds), illustrating the chemiluminescent response of an embodiment of an $H_2S$-reactive compound after exposure to $H_2S$.

As indicated herein, the color change produced by embodiments of the disclosed chemiluminescent testing methods can be chemiluminescence that can be detected with the naked eye, such as illustrated in FIG. 8. In an independent embodiment, the chemiluminescence can be detected spectroscopically, such as illustrated in FIG. 9. In some embodiments, the visual detection limit obtained using chemiluminescent methods disclosed herein are well below the reported range of $H_2S$ concentrations (e.g., 20 µM-100 µM) in mammalian blood. In some embodiments, the visual detection limit can range from greater than 0 to at least 1M, such as 50 nM to 1M, or 0.5 (±0.3) 1 µM to 6 (±2.0) µM, or 0.2 µM to 8 µM, or 0.2 µM to 7 µM, 0.2 µM to 5 µM, 0.2 µM to 4 µM. The detection limits of the methods using the disclosed chemiluminescent compound, or composition thereof, can vary depending on the type of sample that is used.

Figure 10:
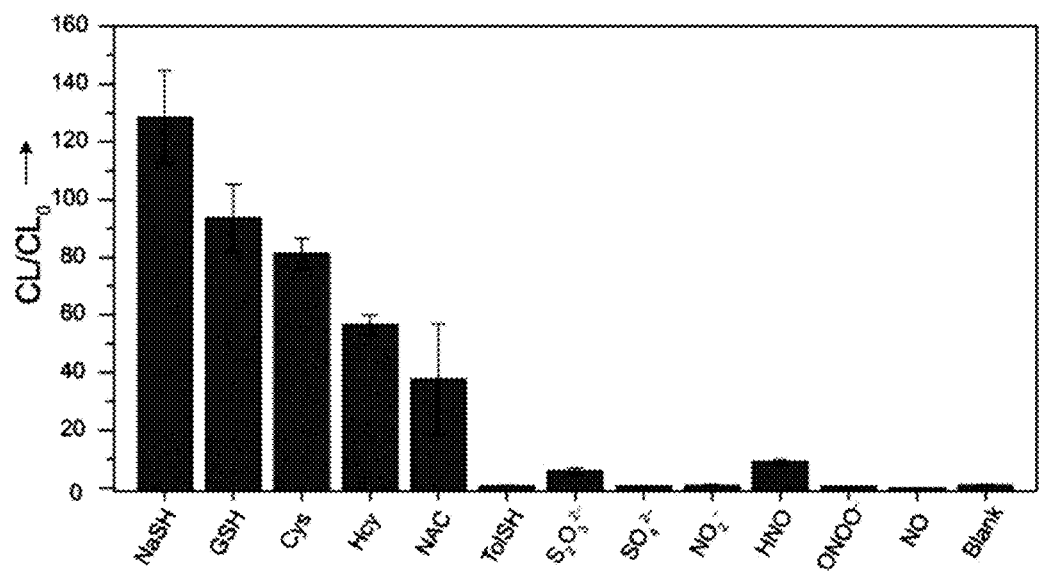
FIG. 10 is a bar graph indicating the selectivity of a particular $H_2S$-reactive compound embodiment for $H_2S$ determination in comparison to various different reactive oxygen, nitrogen, and sulfur-containing species.
Figure 11:
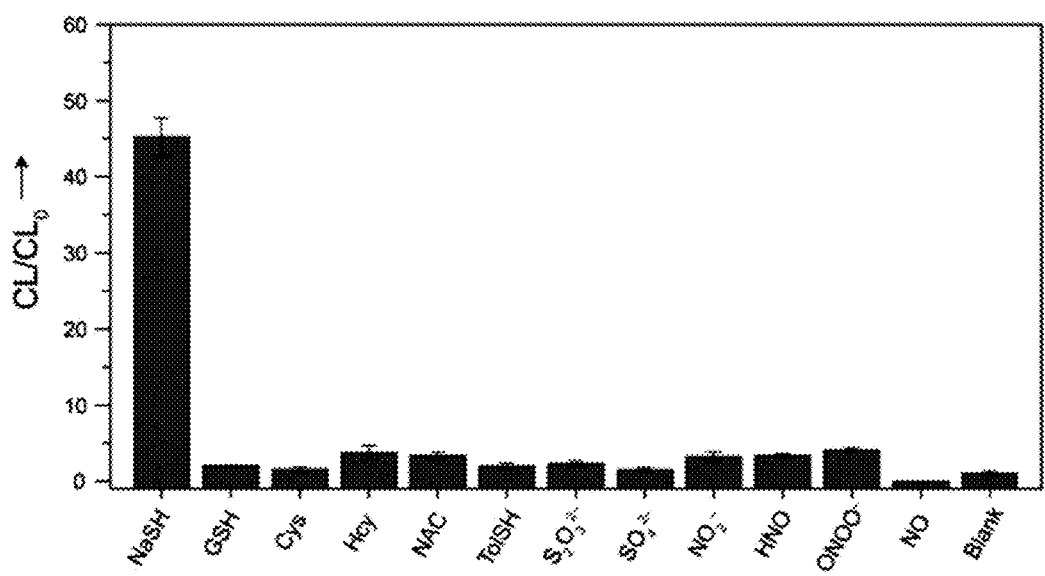
FIG. 11 is a bar graph indicating the selectivity of a particular $H_2S$-reactive compound embodiment $H_2S$ determination in comparison to various different reactive oxygen, nitrogen, and sulfur-containing species.

The selectivity, discussed above, of the disclosed chemiluminescent testing methods is corroborated by the results illustrated in FIGS. 10 and 11. As illustrated in FIGS. 10 and 11, the disclosed chemiluminescent compound precursors and method of using the chemiluminescent compound precursors provides a luminescent signal when reacted with NaSH (an $H_2S$ donor); such a signal is not produced in embodiments where reactive compounds, such as cysteine, homocysteine, N-acetylcysteine, reduced glutathione, thiosulfate, sulfate, nitric oxide, nitroxyl, and nitrite are exposed to the chemiluminescent compound precursor embodiments disclosed herein.

Figure 12:
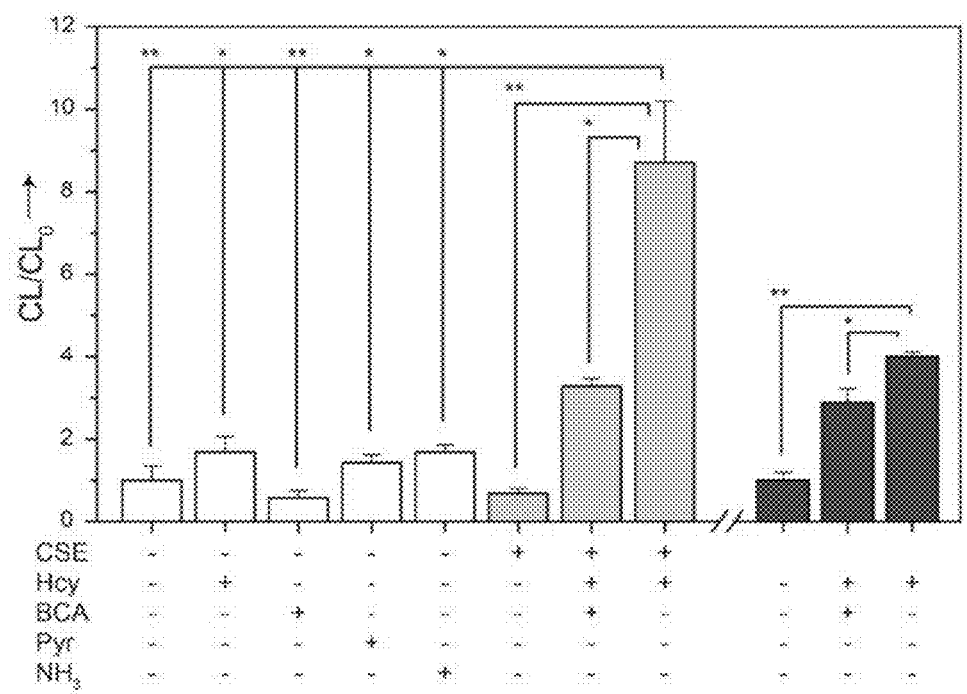
FIG. 12 is a graph of chemiluminescence (counts×$10^6$) versus time (seconds) illustrating detection of cystathionine γ-lyase-produced $H_2S$ using an $H_2S$-reactive compound embodiment disclosed herein.

In some embodiments, the disclosed chemiluminescent testing methods can be used to selectively detect $H_2S$ produced by an enzyme, such as an enzyme capable of converting a biologically active thiol (e.g., homocysteine or cysteine) to $H_2S$. Such embodiments are useful for biological analysis, such as in vitro and/or in vivo analysis for determining whether $H_2S$ is present. An exemplary enzyme is cystathionine γ-lyase (referred to herein as "CSE"). In some embodiments, exposing a sample comprising, consisting essentially of, or consisting of a chemiluminescent compound, an enzyme capable of generating $H_2S$ (e.g., CSE), and a biologically active thiol (e.g., homocysteine or cysteine), produces chemiluminescence. For example, FIG. 12 illustrates results obtained from an embodiment where the response between chemiluminescent compound precursor 202 and enzymatically produced $H_2S$ (eighth bar from the left in FIG. 12).

In yet additional embodiments, the disclosed methods can be used to detect and quantify endogenously-produced $H_2S$ in cells, such as C6 cells, which express CSE and produce $H_2S$ endogenously. Such methods are useful for detecting endogenously-produced $H_2S$ even in the presence of other biological species; such selectivity is not obtained with conventional chemiluminescent testing methods. In some embodiments, the method comprises providing one or more chemiluminescent compound precursors (or composition thereof), exposing a cell sample to the chemiluminescent compound precursor (or composition thereof), exposing the sample to $H_2O_2$, horseradish peroxidase, sodium hydroxide, and an optional enhancer, and analyzing the sample for chemiluminescence. Results from such an exemplary embodiment are illustrated in FIG. 12.

4. Kits for Chemiluminescent Testing

Also disclosed herein are embodiments of kits for detecting $H_2S$ using chemiluminescent testing methods disclosed herein. In some embodiments, the kit can comprise, consist essentially of, or consist of a pre-measured amount of the chemiluminescent compound precursor, which can be greater than 0 to at least 100 mg, such as 1 µg to 100 mg, or 1 µg to 1 mg, or 1 mg to 100 mg, or 500 µg to 600 µg.

In some embodiments, the kits can comprise, consist essentially of, or consist of a container (e.g., a cuvette, a sample bottle, or the like) housing one or more of the chemiluminescent compound precursors disclosed above, such as compounds 200 or 202, and an enzyme, a transition metal cation, an oxidant, an enhancer, a base, or any combination thereof. In some embodiments, the kit can comprise, consist essentially of, or consist of a container that houses the chemiluminescent compound precursor and one or more additional containers that can each independently house the enzyme, the oxidant, the enhancer, the base, or any combination thereof. In some embodiments, the kits can further include a visualization chamber in which analysis of the sample may be conducted in substantial darkness to facilitate visualization of chemiluminescence produced by the product formed from the chemiluminescent compound precursor.

In other embodiments, the kits can comprise, consist essentially of, or consist of a well plate comprising, consisting essentially of, or consisting of pre-measured amounts of the chemiluminescent compound precursor, the enzyme, the transition metal cation, the oxidant, the enhancer, the base, or any combination thereof within one or more wells of the well plate. Such kits can be used for biological assays utilizing chemiluminescent testing.

C. Bioluminescent Testing

While isolated examples of bioluminescent detection of reactive oxygen species has been reported in the art, these methods do not detect $H_2S$. Furthermore, biocompatible compounds, such as the $H_2S$-reactive compounds disclosed herein, for determining the presence of and amount of $H_2S$ in various media using such methods are not well established.

Bioluminescent imaging methods disclosed herein are non-invasive and suitable for studying molecular processes in a variety of samples, such as contained samples (like cuvette samples used for bio-analytical techniques), cell lines, or live animals. The disclosed bioluminescent methods, unlike fluorescence imaging techniques, do not require external excitation, thus providing a less-invasive imaging technique with higher signal-to-noise ratios.

Furthermore, the $H_2S$-reactive compounds used these disclosed methods can be made and/or derivatized specifically to react with purified luciferase enzymes typically used in the art for bioluminescent imaging. Such compounds and methods also can be used with genetically encoded cell lines and animals expressing luciferase, thus providing a broad spectrum of chemical, biochemical, and biomedical analysis methods—including in vitro assays and in vivo methods.

Additionally, the disclosed bioluminescent testing methods can be used for non-invasive detection of $H_2S$ in animals or animal models, a feature that is currently understood as not being possible with $H_2S$ testing methods currently used in the art. Accordingly, the disclosed compounds and bioluminescent methods provide scaffolds for high-throughput screening for cell-based assays in which the up- or down-regulation of $H_2S$-producing enzymes is monitored, or in whole-animal imaging experiments in animals expressing bioluminescence-enabling genes. The present bioluminescent methods also do not require the use of instruments for sample analysis as all analysis may be conducted visually. Such methods are useful in situations where the use of analytical instrumentation is impractical, undesired, and/or unavailable. Also, the present bioluminescent methods allow people with minimal training and/or knowledge of H$_2$S detection techniques to use the compounds, compositions, and/or kits disclosed herein to determine the presence of H$_2$S in samples.

1. Compounds for Bioluminescent Testing Methods

Disclosed herein are embodiments of H$_2$S-reactive compounds that can be used in bioluminescent testing methods. In some embodiments, the H$_2$S-reactive compounds can be bioluminescent compound precursors having one or more functional groups that can react with H$_2$S to provide a reaction product that can then be oxidized by an enzyme or by atmospheric oxygen to provide a compound that generates bioluminescence. In some embodiments, the bioluminescent compound precursor is a luciferin-based compound comprising an azide moiety. Suitable luciferin-based compounds include particular luciferin species, such as firefly luciferin, renilla luciferin, and/or bacterial luciferin that have been modified to comprise an azide moiety. Such compounds are derivatized with an azide moiety to make a compound that can be selectively reduced by H$_2$S (as opposed to biological thiol, or other biological species, such as those disclosed herein) to provide a reaction product capable of being oxidized by a luciferase enzyme thereby generating bioluminescence that can be visually detected.

In some embodiments, the bioluminescent compound precursors can have a Formula 1, wherein R$^1$ is an azide, R$^2$ can be hydrogen or alkyl, n can be 0, 1, or 2, and ring A can be a thiazole, oxazole, or imidazole comprising at least one R$^3$ group, with the R$^3$ group being selected from a heterocyclyl group comprising one or more substituents such as a carboxyl or amide.

In some embodiments, the bioluminescent compound precursors can have a Formula 11, illustrated below, wherein R$^2$ can be as recited for Formula 1, X can be sulfur, oxygen, or NR$^5$ (wherein R$^5$ can be hydrogen, alkyl, alkenyl, alkynyl, aryl, or heteroaryl), and R$^7$ can be hydroxyl or amine.

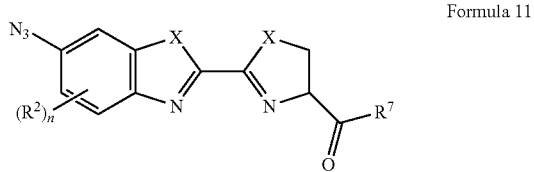

Formula 11

Exemplary bioluminescent compound precursors are provided in Table 3.

TABLE 3

Exemplary Bioluminescent Compound Precursors

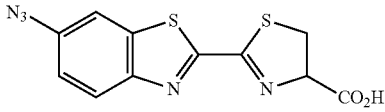

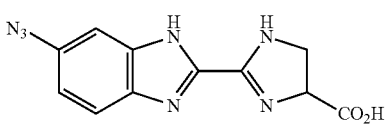 [SMILES: [N-]=[N+]=Nc1ccc2nc(C3=NC(C(=O)O)CN3)[nH]c2c1]

TABLE 3-continued

Exemplary Bioluminescent Compound Precursors

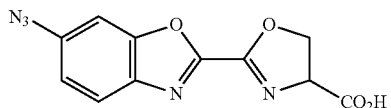

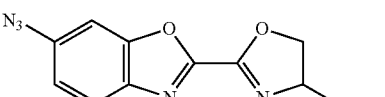

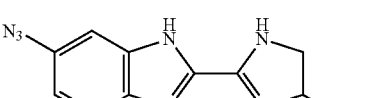

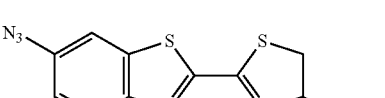

In an independent embodiment, the bioluminescent compound precursor can be selected from the following:

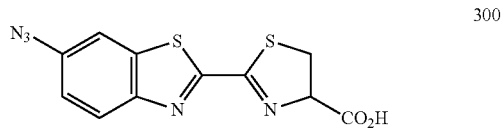

300

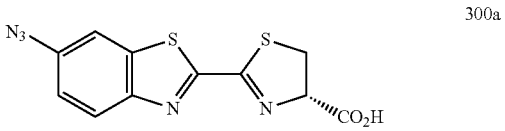

300a

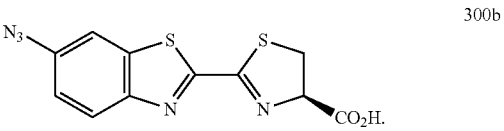

300b

In some embodiments, the disclosed bioluminescent compound precursors can be in the form of compositions. Such compositions can comprise, consist essentially of, or consist of one or more of the bioluminescent compound precursors disclosed above in combination with a solvent (organic or aqueous), a buffer, a carrier, and combinations thereof. In some embodiments, the composition comprises, consists essentially of, or consists of one or more of the disclosed bioluminescent compound precursors in combination with a solvent, such as water, dimethylsulfoxide, dimethylformamide, dimethylacetamide, acetonitrile, methanol, ethanol, (or other alcohols), and combinations thereof. In some embodiments, the composition can include a concentration of the bioluminescent compound precursor ranging from greater than 0 to at least 500 mg, such as 10 ng to 500 mg, such as 1 mg to 100 mg, or 500 µg to 700 µg.

In some embodiments, the compositions can also include a means for converting a product obtained from the reaction between the bioluminescent compound precursor and H$_2$S into a compound that emits bioluminescence. In some embodiments, the means can be a luciferase enzyme, such as a bacterial luciferase enzyme, a renilla luciferase enzyme, or a firefly luciferase enzyme.

2. Methods of Making Bioluminescent Compound Precursors

Disclosed herein are embodiments of a method for making bioluminescent compound precursors that can be used in the bioluminescent testing methods disclosed herein. In some embodiments, the bioluminescent compound precursors are made according to Scheme 10. According to Scheme 10, halide 1000 is converted to nitro-containing compound 1002 using reagents known in the art, such as KNO$_3$ and H$_2$SO$_4$, or the like. Nitro-containing compound 1002 is then reduced to amine 1004 using suitable reagents, such as Fe(0), HCl, and EtOH. Amine 1004 is converted to cyano-containing compound 1006 using a cyanide reagent, such as KCN in DMSO. Cyano-containing compound 1006 and amine 1008 then react to form the cyclized product 1010. Azide 1012 is made from the cyclized amine 1010 using the methods disclosed herein, such as by using tert-BuONO and TMS-N$_3$ in DMSO.

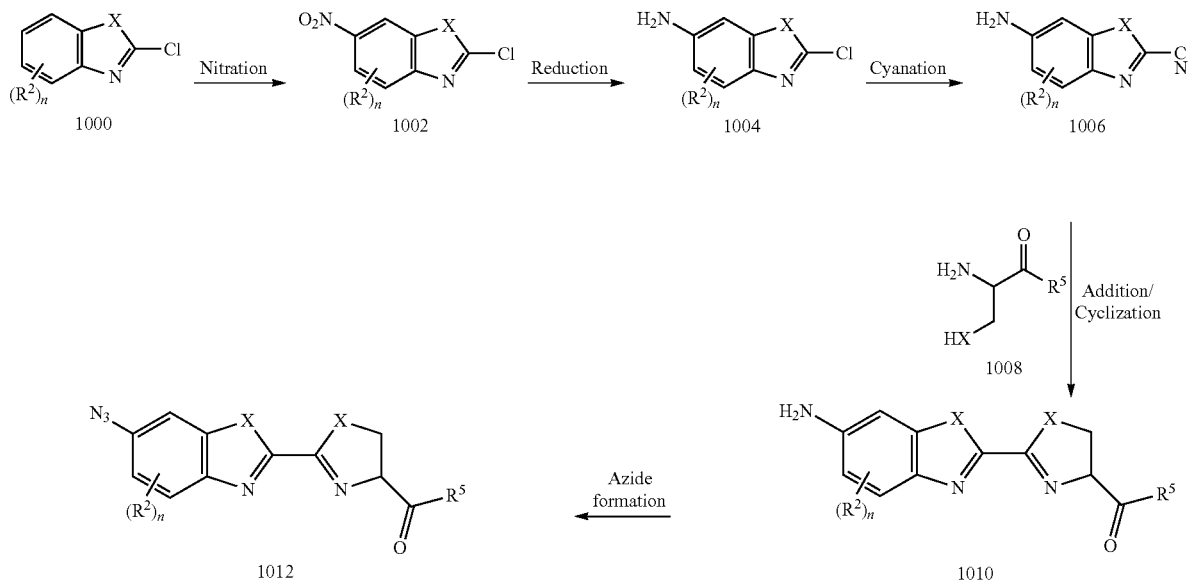

Scheme 10

An exemplary embodiment of making certain bioluminescent compound precursors is provided in Scheme 11.

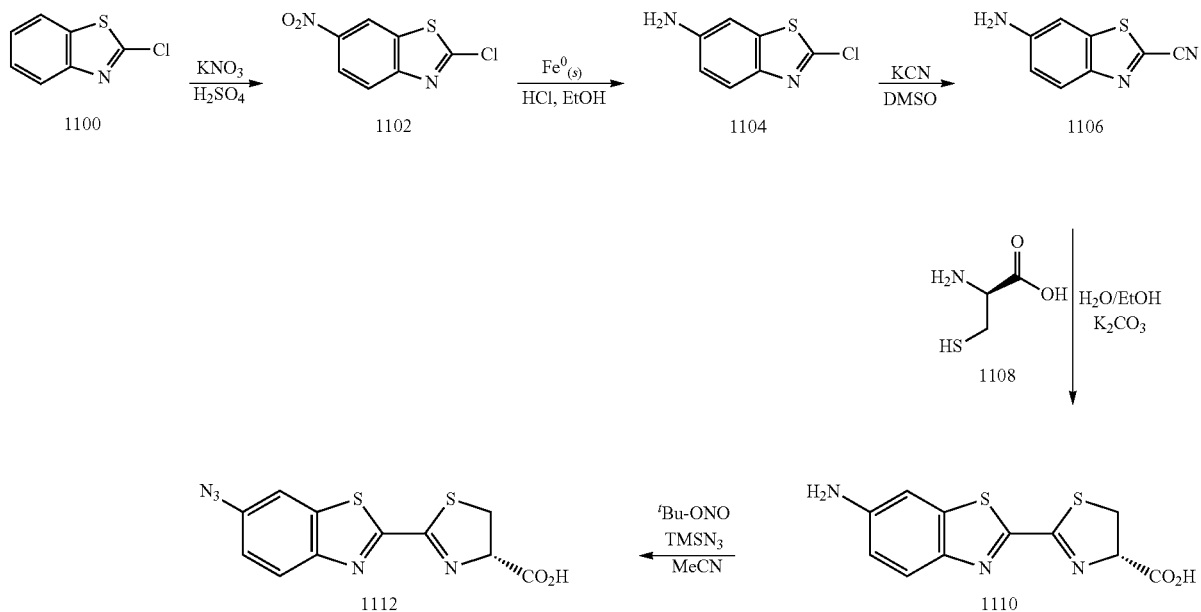

Scheme 11

3. Methods for Bioluminescent Testing

Disclosed herein are methods for determining the presence of $H_2S$ in a sample using bioluminescent compound precursors capable of being selectively reduced by $H_2S$ to provide a compound that emits bioluminescence. In some embodiments, the method comprises, consists essentially of, or consists of providing bioluminescent compound precursors comprising an azide moiety that can be reduced by $H_2S$, exposing a sample to the bioluminescent compound precursor, exposing the sample to a luciferase enzyme, and analyzing the sample for a color change, such as bioluminescence. A person of ordinary skill in the art would recognize a color change has occurred.

In some embodiments, the sample is exposed to an effective amount of the bioluminescent compound precursor (or a composition thereof). Such effective amounts can be any amount of the bioluminescent compound precursor that is sufficient to react with greater than 0 to at least 1M of $H_2S$, such as 100 nM to 1M of $H_2S$, or 200 nM to 1 M of $H_2S$, 1 μM to 100 μM $H_2S$, or 1 μM to 10 μM $H_2S$ present in the sample such that the $H_2S$ can react with the bioluminescent compound precursor, if present, to produce a color change, such as bioluminescence. In some embodiments, the effective amount of the bioluminescent compound precursor may range from greater than 0 to at least 1 M, such as 100 nM to 1 M, or 1 μM to 100 μM, or 5 μM to 10 μM.

The sample can be exposed to the bioluminescent compound precursor (or composition thereof) for a time sufficient to produce a color change, such as bioluminescence. In some embodiments, the sample can be exposed to the bioluminescent compound precursor (or composition thereof) for greater than 0 to at least 120 minutes, such as 30 seconds to 120 minutes, or from 1 minute to 10 minutes, or 2 minutes to 5 minutes.

In some embodiments, the sample is exposed to the bioluminescent compound precursor (or composition thereof) at a particular temperature that does not substantially prohibit the reaction between the bioluminescent compound precursor and $H_2S$, to the extent that any $H_2S$ present in the sample does not react with the bioluminescent compound precursor to provide a visually detectable signal, such as a color change. In some embodiments, the temperature can range from −20° C. to 80° C., such as from 25° C. to 37° C., or 5° C. to 10° C. Additionally, the sample can be exposed to the bioluminescent compound precursor at a pH that can promote a reaction between the bioluminescent compound precursor and any $H_2S$ present in the sample and/or maintain the integrity of the particular sample being analyzed. For example, in some embodiments, the sample may be a biological sample and therefore should be maintained at a biological pH. In some embodiments, the pH can be adjusted to or maintained at a pH of 3 to 12, such as from 6 to 8, or 7 to 7.4.

In some embodiments of the bioluminescent testing methods, a bioluminescent signal produced by a reaction product obtained from the reaction between the bioluminescent compound precursor and $H_2S$ is detected. In some embodiments, the bioluminescent signal is a color change and can be light that is visible to the naked eye in light or dark. In some embodiments, the visually detectable signal can be luminescence that emits within the visible range of the electromagnetic spectrum, such as 380 nm to 790 nm. In some embodiments, the luminescence is detected as a color, such as red (e.g., emission at wavelengths between 620 nm to at least 740 nm); orange (e.g., emission at wavelengths between 585 nm to 620 nm); yellow (e.g., emission at wavelengths between 570 nm to 585 nm); green (e.g., emission at wavelengths between 490 nm to 570 nm); blue (e.g., emission at wavelengths between 440 nm to 490 nm); indigo (e.g., emission at wavelengths between 420 nm to 440 nm); violet (e.g., emission at wavelengths between 400 nm to 420 nm); or any combination thereof.

In some embodiments, the method can further comprise quantifying the amount of $H_2S$ present in the sample. In some embodiments, a relative concentration of $H_2S$ can be determined by evaluating the detectable signal produced. In some embodiments, specific concentrations of $H_2S$ can be detected by calculating the concentration using emission values obtained from spectroscopic analysis of the reaction between $H_2S$ and the bioluminescent compound precursor embodiments disclosed herein.

4. Kits for Bioluminescent Testing

In some embodiments, the kits can comprise, consist essentially of, or consist of a pre-measured amount of the bioluminescent compound precursor, which can range from greater than 0 to 1 g, such as 1 μg to 1 g, or 1 mg to 50 mg, or 2 mg to 5 mg. In some embodiments, the kits can comprise, consist essentially of, or consist of a container (e.g., a cuvette, a sample bottle, or the like) housing one or more of the bioluminescent compound precursors disclosed above, such as compounds 300, 300a, and/or 300b, and a luciferase enzyme. In some embodiments, the kits can comprise, consist essentially of, or consist of one container housing the bioluminescent compound precursor(s), or a composition thereof, and one container houses the enzyme, or a composition thereof.

In other embodiments, the kits can comprise, consist essentially of, or consist of a well plate comprising, consisting essentially of, or consisting of pre-measured amounts of the bioluminescent compound precursors and/or the enzyme within one or more wells of the well plate. Such kits can be used for biological assays utilizing bioluminescent testing methods disclosed herein. In some embodiments, the kits can be calibrated for a presence/absence test corresponding to certain $H_2S$ concentration levels, similar to those described herein. Use of kit components containing different loadings of the bioluminescent compound precursors can be used to provide an estimate the concentration of $H_2S$ present in a sample. In some embodiments, the kits can comprise, consist essentially of, or consist of the bioluminescent compound precursors or they can comprise, consist essentially or, or consist of the bioluminescent compound precursor, a buffer compound, a bioluminescent enzyme, or any combination thereof.

V. Working Embodiments

Colorimetric Methods

Materials and Methods: Flash chromatography was performed using silica gel and an automated flash chromatography instrument. Thin-layer chromatography (TLC) was performed on silica gel plates (250 μm thickness) and viewed by UV illumination. NMR spectra were acquired on either a 500 or 600 MHz spectrometer at 25.0° C. Chemical shifts are reported in parts per million (δ) and are referenced to residual protic solvent resonances. The following abbreviations are used in describing NMR couplings: (s) singlet, (d) doublet, (t) triplet, (m) multiplet and (b) broad. NMR spectra of NaSH-containing solutions were prepared under nitrogen in sealable J-Young NMR tubes. UV-visible spectra were acquired on a UV-vis spectrophotometer equipped with a dual cuvette temperature controller and fluorescence spectra were obtained on a spectrofluorimeter equipped with a cuvette temperature controller. Spectroscopic measurements were made under anaerobic conditions, with solutions prepared under an inert atmosphere in septum-sealed cuvettes obtained from Starna Scientific Spectroscopic Materials and Methods:

Piperazine-N,N'-bis(2-ethanesulfonic acid) and KCl were used to prepare buffered solutions (50 mM PIPES, 100 mM KCl, pH 7.4) with Millipore water. Buffered solutions were deoxygenated by vigorous sparging with nitrogen for at least two hours and were stored in an inert atmosphere glove box. DMSO was degassed by three freeze-pump-thaw cycles and stored under nitrogen. Samples for spectroscopic measurements were prepared in an $N_2$-filled glove box with $O_2$ levels less than 1.0 ppm. Anhydrous sodium hydrogen sulfide (NaSH, purity ~98%, Strem) was handled under nitrogen. S-Nitroso-N-acetyl-DL-penicillamine (SNAP) was stored at −30° C. prior to use. Stock solutions of NBD-containing compounds were prepared in deoxygenated DMSO and stored in aliquots at −25° C. under nitrogen until immediately prior to use.

General Procedure for Hammett Rate Studies:

Stock solutions of each thioether (10 mM) in DMSO and cuvettes containing 3.0 mL of pH 7.4 PIPES buffer, a stir bar, and a septum cap were prepared in a glove box. Prior to each UV-vis experiment, the cuvette was allowed to equilibrate to 25.0° C. for 5 minutes in the sample holder. After equilibration, 20 equivalents of NaSH from a 10 mM NaSH stock solution was added to the cuvette by syringe. The reaction progress was monitored by collection of UV-vis absorption data at the $\lambda_{max}$ of the either the reactant or the product in 0.1 second intervals. The raw data were fit directly to a first-order decay to obtain pseudo first-order rate constants for the reactions. All fits maintained $R^2$>0.99, and the rates reported are the average of at least five independent experiments.

General Procedure for Detection and Quantification Studies:

Stock solutions of each colorimetric compound precursor (100 mM, 10 mM, and 1 mM) in DMSO and cuvettes containing 3.0 mL of pH 7.4 PIPES buffer, a stir bar, and a septum cap were prepared in a glove box. Different concentrations of compounds 100 or 112 were added to each cuvette and an initial UV-vis spectrum was recorded, after which $H_2S$ was added. After incubation for 30 minutes at room temperature, the absorbance spectrum was acquired. For quantification studies, $H_2S$ was added to a series of cuvettes containing a range of concentrations of 100. After incubation for 30 minutes at room temperature, the absorbance spectrum was recorded. Plotting the absorbance as a function of compound concentration allowed for $H_2S$ quantification after fitting to a sigmoidal curve.

General Procedure for pH Titration:

A 15 mL solution of compound 42 (111 µM) in 100 mM KCl and 10 mM KOH Millipore water was prepared. The pH of the solution was adjusted with 10 M, 5 M, 1 M, 50 mM, or 1 mM solutions of HCl and the pH recorded. At each pH value, an aliquot of the solution was transferred to a cuvette and the UV-vis spectrum was measured. After measurement, the aliquot was returned to the stock solution and the pH was adjusted to the next point in the titration.

General Procedure for Selectivity Studies:

Stock solutions of each colorimetric compound precursor (10 mM) in DMSO, amino acids (10 mM) in pH 7.4 PIPES, cuvettes containing 3.0 mL of pH 7.4 PIPES buffer, a stir bar, and a septum cap were prepared in a glove box. Amino acids were added to individual cuvettes containing 3.0 mL of pH 7.4 PIPES buffer (50 mM PIPES, 100 mM KCl), stirred/shook for 45 minutes at 37° C. $H_2S$ was added to cuvettes by syringe and cuvettes were stirred/shook for 8 minutes at 45° C., then at 37° C. for 37 min. Data was acquired before amino acid addition, 45 minutes after amino acid addition, and 45 minutes after $H_2S$ addition.

X-ray Data Collection and Structure Solution Refinement

Single crystals of 40 suitable for X-ray diffraction were grown by layering hexanes onto a $CHCl_3$ solution of 40. Diffraction data were collected using Mo Kα radiation (λ=0.710 73 Å) at 173(2) K. Data reduction was performed with SAINT and empirical absorption corrections were applied with SADABS. All refinements were performed using the SHELXTL (6.10) software package. The molecular structure was solved by direct methods and was refined using full-matrix least-squares procedures on $F^2$. All non-hydrogen atoms were located and their positions refined anisotropically. Hydrogen atoms were found from the residual density map and were refined with isotropic thermal parameters.

Example 1

The reactivity of $H_2S$ with 4-chloro-7-nitrobenzofurazan (colorimetric compound precursor 100), an electron-deficient small molecule that reacts with thiols to afford a fluorescent thioether (NBD-SR) product, was determined. Without being limited to a particular theory of operation, it is currently believed that nucleophilic attack on colorimetric compound precursor 100 proceeds through a stepwise $S_N^2Ar$ mechanism, often with reversible addition of the nucleophile to formation of the intermediate σ-complex (Meisenheimer complex) and subsequent final product.

To test the proposed reactivity of colorimetric compound precursor 100 toward $H_2S$, colorimetric compound precursor 100 was titrated with NaSH, a common $H_2S$ source, in PIPES buffer (50 mM PIPES, 100 mM KCl, pH 7.4). During the titration, the characteristic 343 nm absorbance of colorimetric compound precursor 100 decreased with the concomitant growth of a new absorbance peak at 534 nm corresponding to nitrobenzofurzan thiol 42 (FIG. 1). During the initial portion of the titration, formation of a second species with absorbances at 298 nm and 413 nm was observed; however, this intermediate was completely consumed during the titration to afford 42, as evidenced by the clean isosbestic points at 256 nm (peak, 371 nm, and 445 nm. Neither 42 nor 40 are fluorescent, but the bathochromic shift and characteristic absorbance of 42 ($\lambda_{max}$ 534 nm, $\epsilon_{534}$=19,000±600 $M^{-1}$ $cm^{-1}$) allowed for visual detection. Additionally, isolated 42 does not react with other nucleophiles, such as cysteine or glutathione (GSH), and it does not extrude $HS^-$ by purging with nitrogen. The 534 nm absorbance of 42 can be abolished, however, by treatment with excess colorimetric compound precursor 100. This reaction proceeds through clean isosbestic points at 256 nm, 371 nm, and 445 nm, resulting in the characteristic absorbances of thioether 40 at 413 nm ($\epsilon_{413}$=11,700±100 $M^4$ $cm^{-1}$) and 298 nm. These studies establish that the reaction pathway outlined in Scheme 3 is operable in solution.

Figure 13:
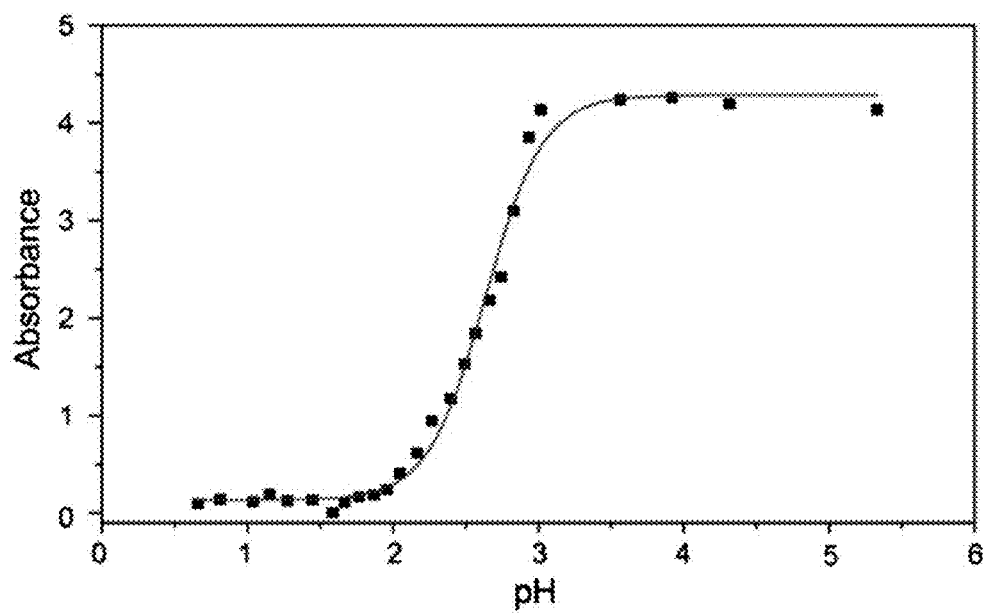
FIG. 13 is a pH titration curve of a disclosed $H_2S$-reactive compound embodiment.

Acidification of a solution of 42 extinguished the 534 nm absorbance and resulted in a new absorbance at 400 nm, suggesting that electron delocalization of the deprotonated thiol over the nitrobenzofurazan ring accounts for the purple color. By monitoring the absorbance of 42 at 534 nm as a function of pH, an apparent pKa of 2.6(1) for the thiol was determined by fitting the titration data (FIG. 13), which is consistent with the high reported acidity of NBD-OH.

Figure 14:
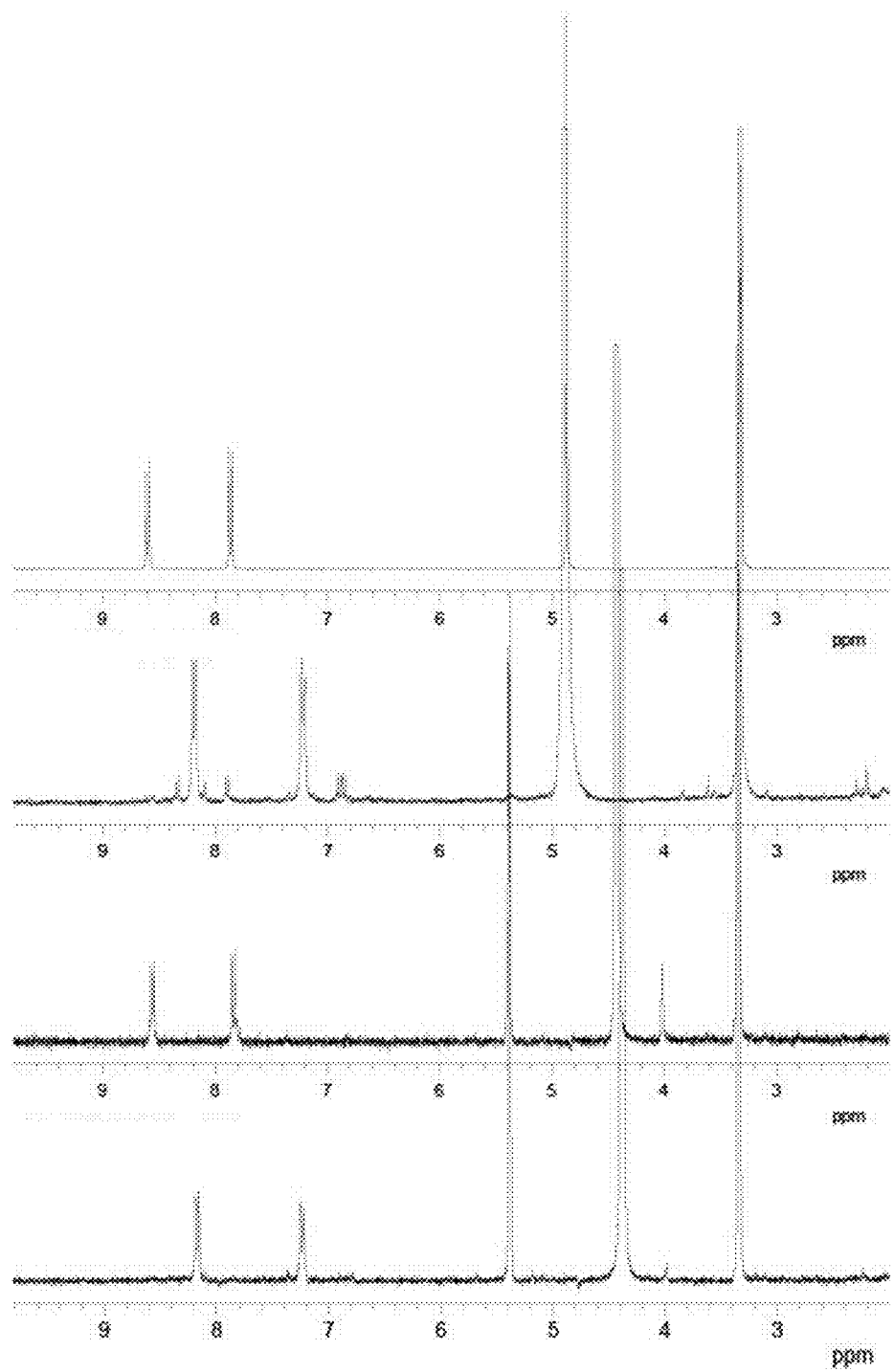
FIG. 14 is a $^1$H NMR spectrum of an H$_2$S-reactive compound embodiment disclosed herein illustrating the progress of a reaction between the H$_2$S-reactive compound and H$_2$S.
Figure 15:
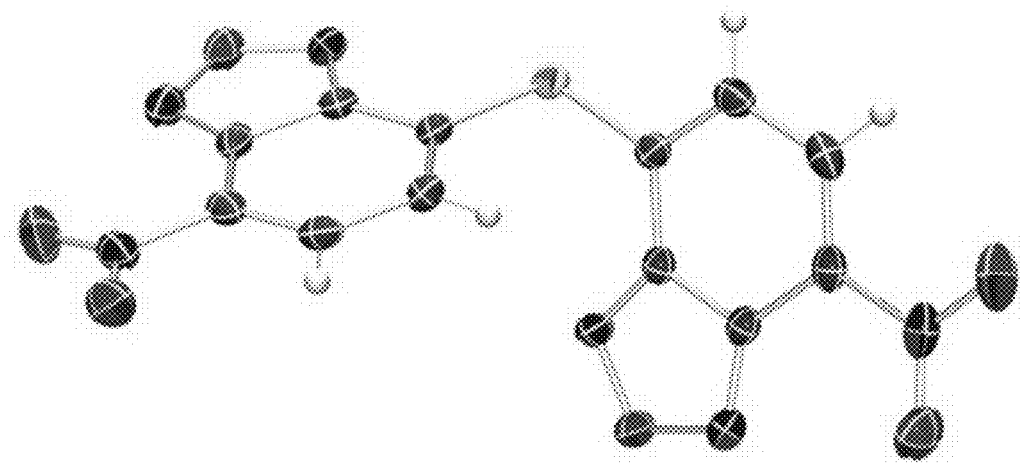
FIG. 15 is an ORTEP diagram of an X-ray crystal structure of an H$_2$S-reactive compound embodiment disclosed herein.

Thioether 40 was isolated by addition of one half of one equivalent of NaSH to a DMF solution of 100. The resultant UV-vis spectrum with $\lambda_{max}$ at 413 nm and at 298 nm (FIG. 2) matched that of the intermediate formed during the titration used to produce the data illustrated in FIG. 1. Similarly, the 8.57 ppm and 7.85 ppm resonances in the $^1$H NMR spectrum matched those generated in situ during NMR titrations of colorimetric compound precursor 100 with NaSH (FIG. 14). Although the downfield $^1$H NMR resonances of 40 suggested that the nitro groups were intact, recent reports on the H$_2$S-mediated reduction of nitro groups to amines prompted unambiguous structural determination. Single crystals of 40 suitable for X-ray diffraction were grown from CHCl$_3$/hexanes and confirmed no reduction of NO$_2$ groups of compound 40 occurred (FIG. 15).

Figure 16:
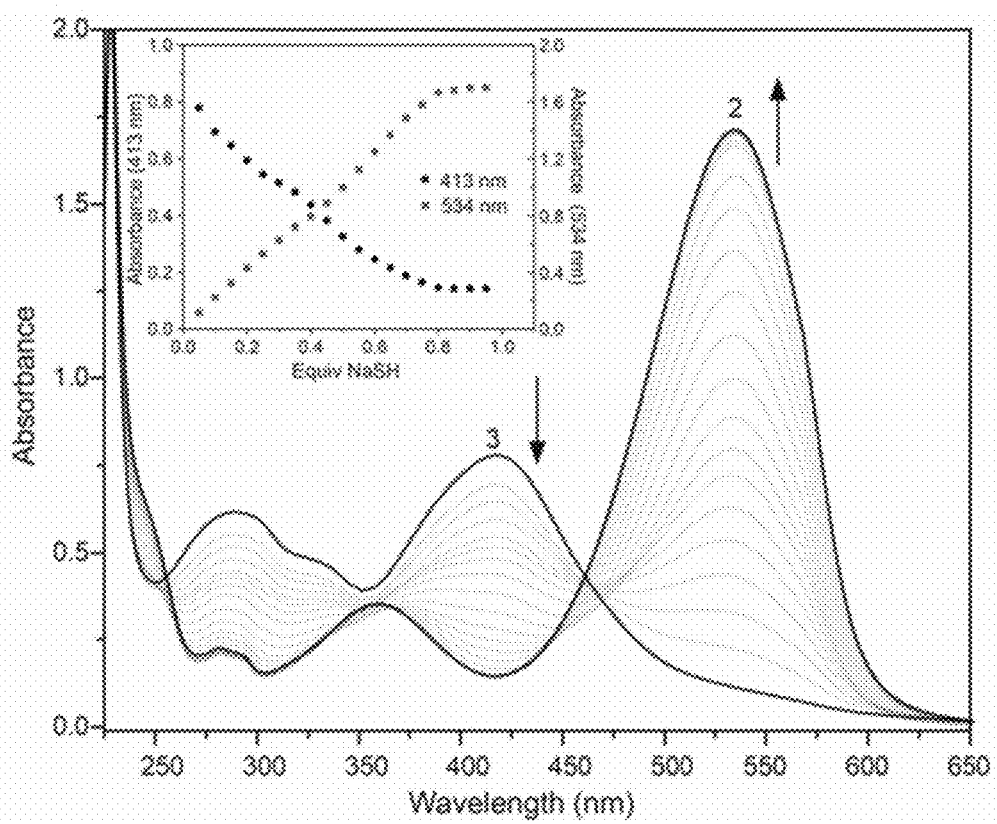
FIG. 16 is a UV-visible spectrum of an H$_2$S-reactive compound embodiment disclosed herein as well as the H$_2$S-reactive compound after reaction with NaSH.

Based on the intermediate formation of 40 during the titration of colorimetric compound precursor 100 with H$_2$S, it is currently believed that HS$^-$ is sufficiently nucleophilic to attack the ipso carbon of 40 to yield 42. Using isolated 40, this reactivity was investigated directly by titrating NaSH to a solution of 40 in pH 7.4 PIPES buffer at 37° C. The reaction was monitored by both UV-vis (FIG. 16) and $^1$H NMR spectroscopy (FIG. 14, wherein the top spectrum is from colorimetric compound precursor 100, the second spectrum from the top is from colorimetric compound precursor 100 in the presence of H$_2$S, the third spectrum from the top is thioether 42, and the bottom spectrum is the spectrum of thioether 42 in the presence of H$_2$S). Addition of 1 equivalent of NaSH to a solution of 40 resulted in formation of two equivalents of 42, confirming both the overall stoichiometry of the reaction and the high electrophilicity of thioether 40.

Example 2

Treatment of colorimetric compound precursor 100 with different thiols in DMF with excess K$_2$CO$_3$ afforded colorimetric compound precursors 110-116 (Scheme 1). The resultant colorimetric compound precursors (110-116) all reacted cleanly with NaSH in pH 7.4 PIPES buffer to afford 42 and one equivalent of the extruded thiol (Scheme 4), which demonstrated the tolerance for both electron donating and withdrawing groups. Kinetic data from the reaction of colorimetric compound precursors 110-116 with 20 equivalents of NaSH under pseudo first-order conditions were used to construct a Hammett plot. See, for example, FIGS. 17-19, where FIG. 17 illustrates data obtained from reaction of a compound embodiment with excess NaSH, FIG. 18 illustrates time course data of the absorbance at 534 nm fit directly to the first-order rate equation, and FIG. 19 illustrates a Hammett plot of the reaction of the colorimetric compound precursors with NaSH under pseudo first order conditions. Based on the proposed S$_N$2Ar mechanism of the reaction, it was expected that electron withdrawing groups appended to the benzene ring would facilitate the nucleophilic attack of HS$^-$ on 40. Construction of a Hammett plot using $\sigma p$ values revealed a positive slope with $\rho=+0.34$, consistent with the proposed S$_N$2Ar mechanism (FIG. 19). This value demonstrates that although the reaction is facilitated by electron withdrawing groups, different substitutions on the arene are readily tolerated while maintaining reaction rates amenable to real-time H$_2$S detection.

Treatment of colorimetric compound precursor 100 with sub-stoichiometric H$_2$S forms a mixture of 42 and 40, consistent with the titration results shown in FIG. 1. This mixture can be completely converted to 42 by stoichiometric treatment with H$_2$S. Similarly, colorimetric compound precursors 110-116 react with H$_2$S to generate 42 with concomitant extrusion of one equivalent of the corresponding aryl thiol. Thioether 40 also reacts with thiols, such as PhSH, to generate one equivalent of a nonsymmetric thioether and one equivalent of 42. This reactivity of the disclosed colorimetric compound precursors is consistent with the recent report of sulfide-thiol exchange between NBD-sulfides and N-acetylcysteine methyl ester as a probe for cysteine residues in proteins. Although the NBD thioethers react readily with thiols or H$_2$S at physiological pH, no reaction with amine or alcohol nucleophiles was observed the disclosed colorimetric compound precursors, thus highlighting the tolerance of this reaction platform for thiol/H$_2$S reactions over other potential biological nucleophiles.

Example 3

To establish the ability of colorimetric compound precursor 100 to act as an H$_2$S detector, colorimetric compound precursor 100 was treated with 50 equivalents of different amino acids or reactive sulfur, oxygen, and nitrogen species (RSONS). Although reaction of colorimetric compound precursor 100 with cysteine or GSH results in a light yellow color due to formation of NBD-SR thioethers, only H$_2$S generates the characteristic color corresponding to 42 (FIGS. 3, 4A and 4B). These results demonstrate that colorimetric compound precursor 100 can be utilized to visually detect H$_2$S without the aid of any instrumentation.

Example 4

Figure 20A:
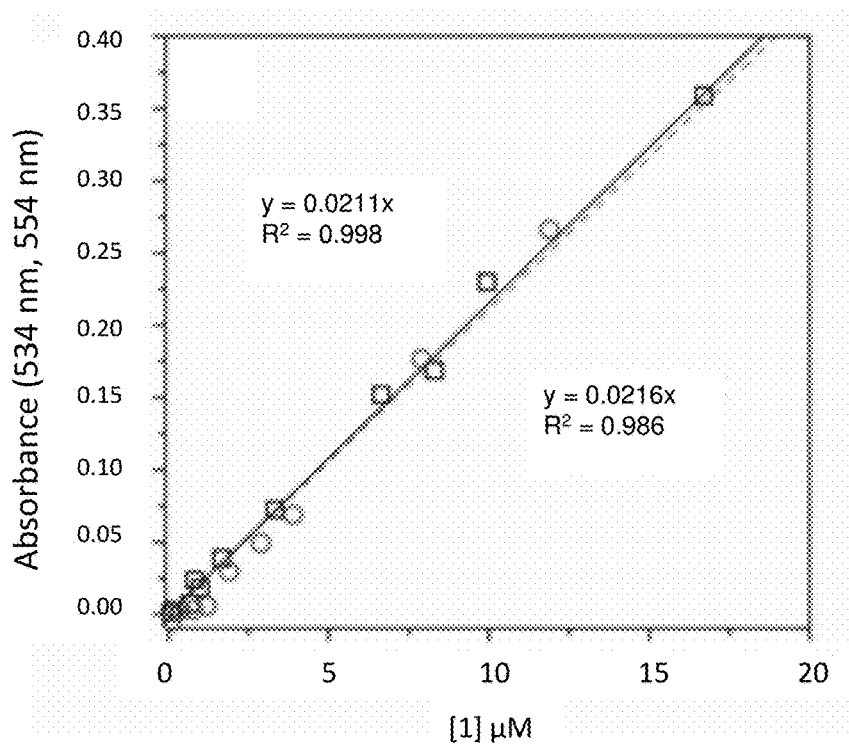
FIGS. 20A and 20B are graphs of absorbance versus concentration illustrating linearity of the colorimetric response obtained from particular H$_2$S-reactive compound embodiments disclosed herein.
Figure 20B:
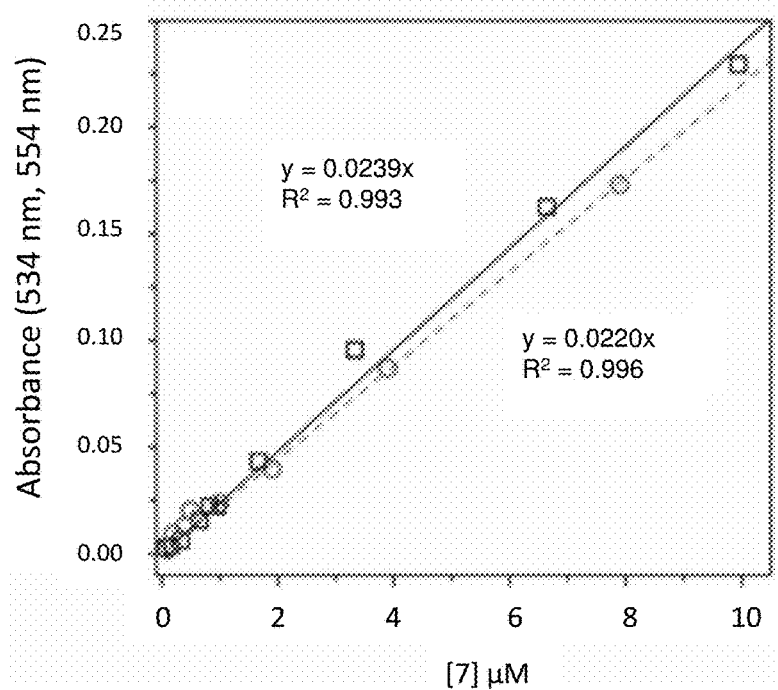

To test the selectivity of both colorimetric compound precursor 100 and colorimetric compound precursor 116 for H$_2$S over other biologically-relevant nucleophiles, 3 μM of each compound was pre-incubated with 10 equivalents of H$_2$S, glycine, serine, tyrosine, lysine, glutathione, and N-acetyl-L-cysteine. After this initial incubation, only the H$_2$S samples showed the characteristic absorbance peak at 534 nm, which was consistent with the visual H$_2$S detection embodiments. To test whether the biologically-relevant nucleophiles deactivated the compounds toward H$_2$S, 30 equivalents of H$_2$S was then added and incubated the compounds for 45 min. In these embodiments, a robust colorimetric response to H$_2$S was observed even after incubation with biological nucleophiles (FIG. 20A, which illustrates results obtained with colorimetric compound precursor 100 and FIG. 20B, which illustrates results obtained with compound 116). Although the H$_2$S response of colorimetric compound precursors 100 and 116 was somewhat eroded after incubation of GSH and N-acetylcysteine, these studies demonstrate a proof of principle for nucleophilic displacement ligated biologically-relevant thiols by H$_2$S. Similarly, the selectivity for H$_2$S over other biologically-relevant nucleophiles, either separately or in competition, demonstrates the effectiveness of the disclosed colorimetric compound precursors in H$_2$S detection.

Example 5

Figure 21:
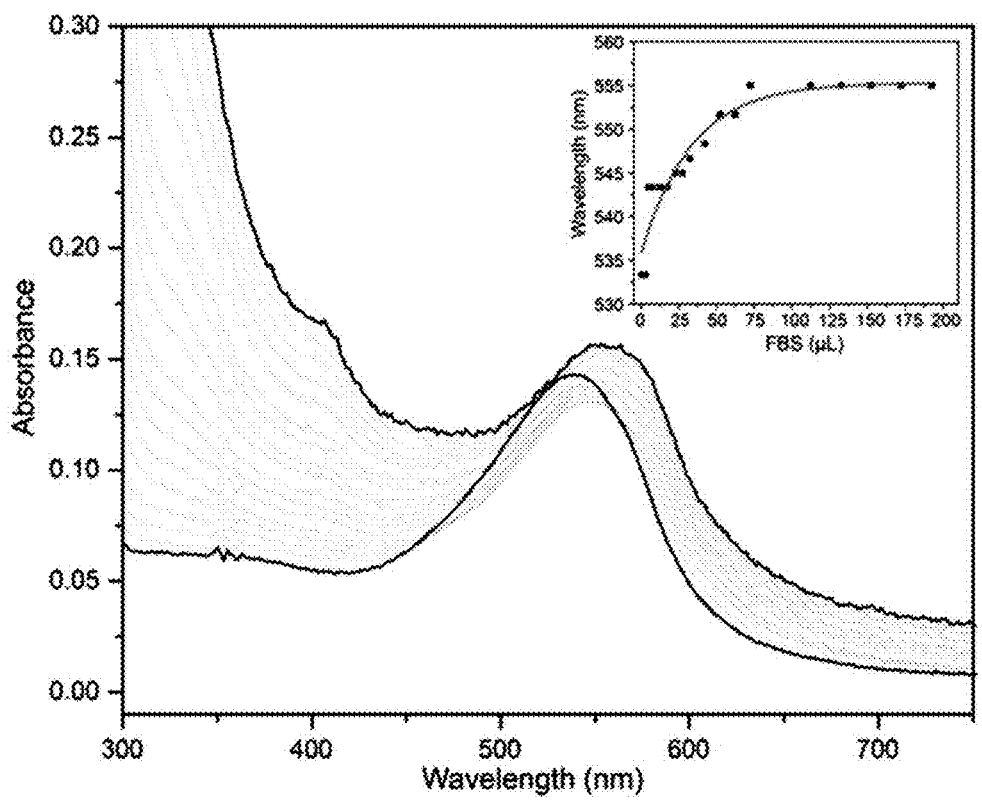
FIG. 21 is a graph of absorbance versus concentration illustrating the change in absorbance of an H$_2$S-reactive compound embodiment disclosed herein as a function of added fetal bovine serum (FBS).

Based on the characteristic absorbance of 42 at 534 nm, the detection limit of colorimetric compound precursor 100 for H$_2$S in PIPES buffer was determined. Because of the sigmoidal response of electrophilic nitrobenzofurazans due to initial formation of 40 prior to formation of 42, as demonstrated in FIG. 1, a 5-fold excess of H$_2$S was added to each sample. Under these conditions, a highly linearity response of colorimetric compound precursor 100 with H$_2$S was observed, with a corresponding detection limit (3σ) of 210±40 nM $H_2S$ (FIG. 17). Similarly, the detection limit of colorimetric compound precursor 116 for $H_2S$ was tested under identical conditions, which revealed an $H_2S$ detection limit of 190±60 nM $H_2S$ (FIG. 18). The efficacy of colorimetric compound precursors 100 and 116 to detect $H_2S$ in biological media also was tested by testing the reactivity and detection limit of both compounds toward $H_2S$ in fetal bovine serum (FBS). In FBS, reaction of 42 or colorimetric compound precursor 116 toward $H_2S$ was identical to that observed in buffer, but the $\lambda_{max}$ of the $H_2S$ reaction product 42 shifted to 554 nm. This shift in $\lambda_{max}$ likely is attributed to association of 42 with proteins present in FBS. Titration of FBS into a solution of 42 demonstrated that this bathochromic shift is complete after approximately 3% FBS by volume (FIG. 21). Following the same procedure as in PIPES buffer, the $H_2S$ detection limits of colorimetric compound precursors 100 and 116 in FBS were determined to be 380±60 nM and 440±40 nM, respectively. Both of these ranges are well below the reported range of biologically-relevant $H_2S$ concentrations including reported levels of 5-100 μM in blood and 50-160 μM in brain homogenates. The low detection limits, fast reaction times, and characteristic product absorbance make both colorimetric compound precursors 100 and 116, as well as the other colorimetric compound precursors disclosed herein, robust compounds for colorimetric $H_2S$ detection and quantification.

Example 6

Figure 22:
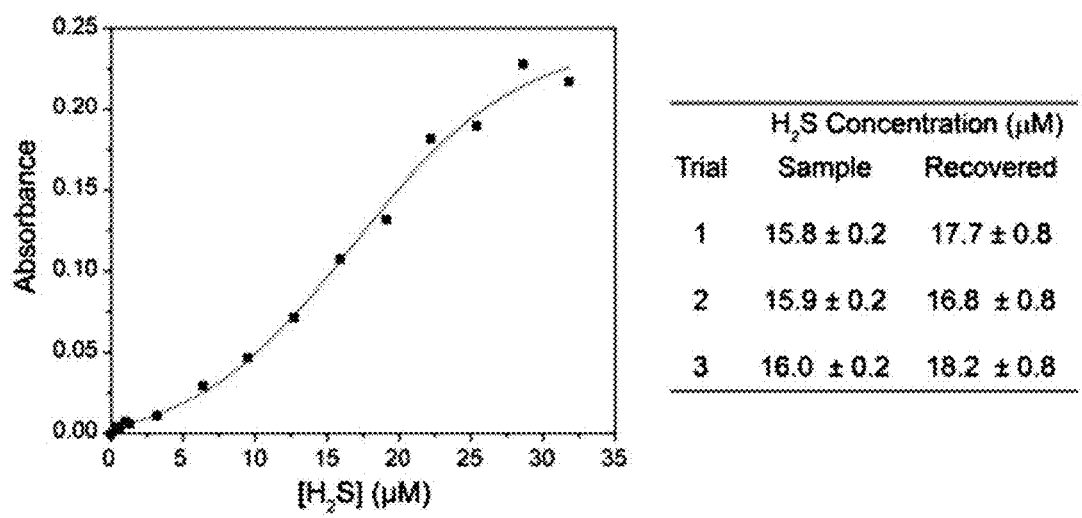
FIG. 22 is a graph of absorbance versus H$_2$S concentration illustrating the response of treating an H$_2$S-reactive compound embodiment with varying amounts of H$_2$S.

In addition to the low detection limits of $H_2S$ detection, the reaction mechanism of $H_2S$ with colorimetric compound precursor 100 or 116, which proceeds through initial formation of thioether 40 before formation of 42, allows for $H_2S$ quantification. In some embodiments, if the concentration of $H_2S$ is below that of the NBD electrophile, then thioether 40 is the main species in solution. In some embodiments, if the concentration of $H_2S$ is above that of the NBD electrophile, then 42 is the major species in solution. This dichotomy results in a sigmoidal colorimetric response to $H_2S$ under conditions in which the concentration of colorimetric compound precursor is constant and the concentration of $H_2S$ is modulated. The concentration of colorimetric compound precursor 100 was held constant at 16 μM and added varying amounts of $H_2S$ and measured the resultant absorbance of each sample at 534 nm (FIG. 22). The resultant data was fit to a sigmoidal curve to determine the $H_2S$ concentration. The $H_2S$ concentrations calculated from the sigmoidal fit matched well with the known concentrations of $H_2S$, thus demonstrating the efficacy of $H_2S$ quantification with the colorimetric compound precursors. See FIG. 22 for concentration values.

Example 7

General Procedure for Compound Synthesis

Figure 23A:
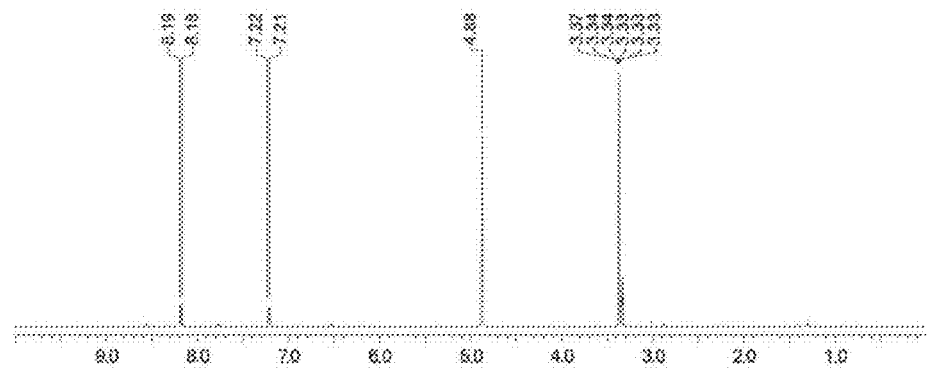
FIGS. 23A and 23B are $^1$H NMR and $^{13}$C NMR spectra, respectively, of an H$_2$S-reactive compound embodiment disclosed herein.
Figure 23B:
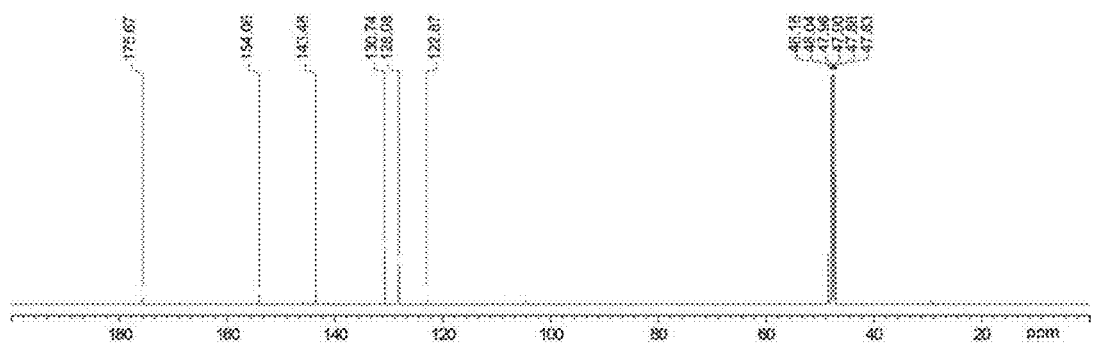
Figure 24A:
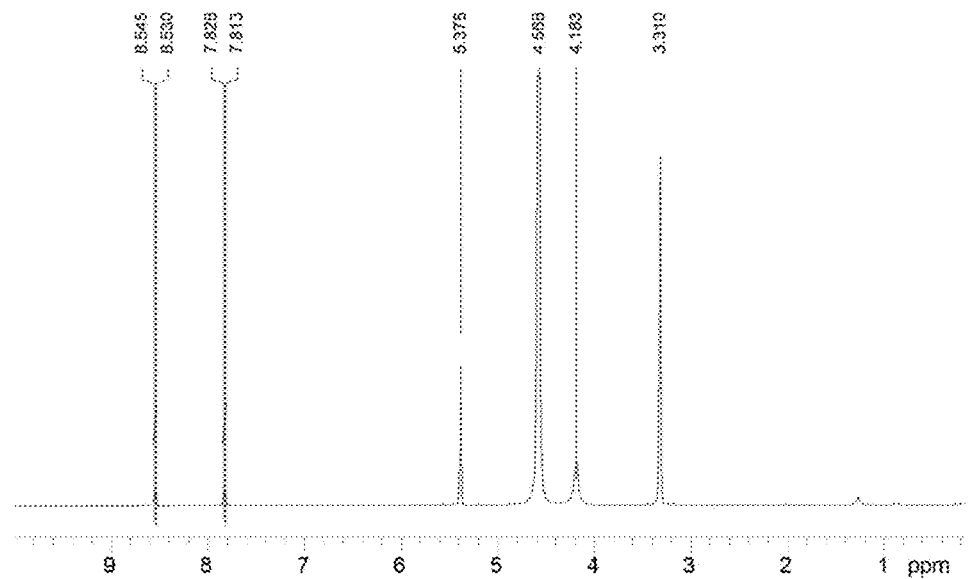
FIGS. 24A and 24B are $^1$H NMR and $^{13}$C NMR spectra, respectively, of an H$_2$S-reactive compound embodiment disclosed herein.
Figure 24B:
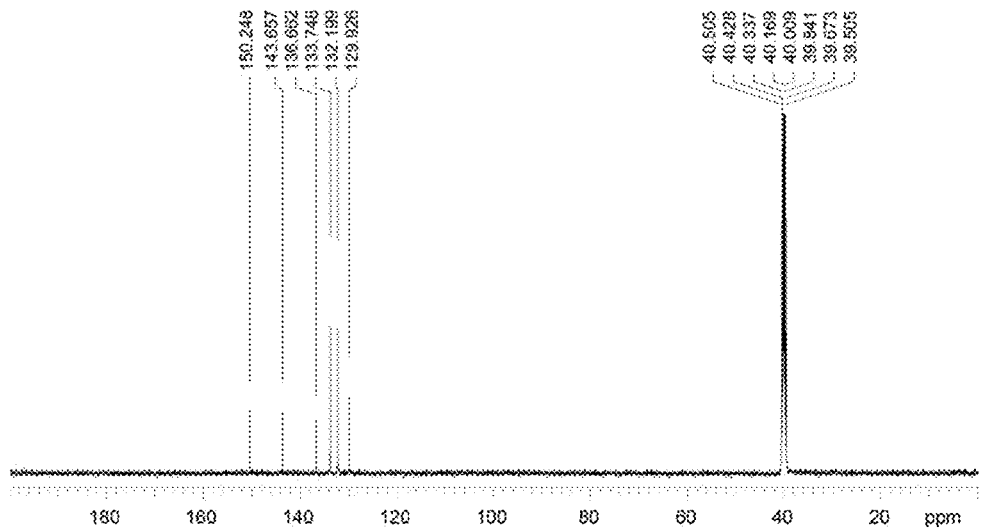

7-Nitrobenzo[c][1,2,5]oxadiazole-4-thiol (42). Colorimetric compound precursor 100 (50.0 mg, 0.251 mmol) was dissolved in 2.0 mL of degassed MeOH. NaSH (38.0 mg, 0.501 mmol) was dissolved in 2.0 mL of degassed MeOH and added to the solution of 100. The reaction mixture was stirred at room temperature under nitrogen for 15 minutes and then purged with nitrogen to remove any unreacted $H_2S$. The MeOH was removed under vacuum, to afford the product as a dark purple powder (46 mg, 92% yield). TLC $R_f$=0.67 ($SiO_2$, 85:15 $CH_2Cl_2$:MeOH). $^1$H NMR (600 MHz, MeOD) δ: 8.18 (d, J=8.7 Hz, 1H), 7.21 (d, J=8.7 Hz, 1H); $^{13}$C{1H} NMR (150 MHz, MeOD) δ: 175.6, 154.1, 143.5, 130.7, 128.1, 122.9. MS-ESI (m/z): [M−H]⁻ calcd for [$C_6H_2N_3O_3S$]⁻, 196.0. found 196.2. The corresponding $^1$H NMR and $^{13}$C NMR spectra are provided in FIGS. 23A and 23B, respectively.

bis(7-Nitrobenzo[c][1,2,5]oxadiazol-4-yl)sulfane (40). Colorimetric compound precursor 100 (300 mg, 1.50 mmol) was dissolved in 2.5 mL of degassed MeOH. NaSH (42.1 mg, 0.752 mmol) was dissolved in 2.5 mL of degassed MeOH and added drop-wise to the solution of colorimetric compound precursor 100. The reaction mixture was stirred at room temperature under nitrogen for 3 hours and then purged with nitrogen to remove any unreacted $H_2S$. The MeOH was removed under vacuum, and the product was purified by $SiO_2$ chromatography (100% $CH_2Cl_2$) to afford the product as a yellow powder (80.3 mg, 30% yield). TLC $R_f$=0.61 ($SiO_2$, $CH_2Cl_2$). $^1$H NMR (500 MHz, 3:2 $CD_2Cl_2$: MeOD) δ: 8.54 (d, J=7.5 Hz, 1H), 7.82 (d, J=7.5 Hz, 1H). $^{13}$C{1H} NMR (125 MHz, DMSO) δ: 150.3, 143.7, 136.7, 133.8, 132.2, 129.9. MS-ESI (m/z): [M+Cl]⁻ calcd for [$C_{12}H_4ClN_6O_6S$]⁻, 395.0. found 395.0. The corresponding $^1$H NMR and $^{13}$C NMR spectra are provided in FIGS. 24A and 24B, respectively.

Colorimetric compound precursors 110-116: Colorimetric compound precursor 100 (30.0 mg, 0.150 mmol) and $K_2CO_3$ (20.7 mg, 0.150 mmol) were added to 3.0 mL of degassed DMF. The desired substituted benzenethiol (0.150 mmol) was added to the reaction mixture, and the resultant reaction mixture was stirred at room temperature for 16 hours under nitrogen. The reaction mixture was diluted with 5 mL of $H_2O$, and the crude product was extracted with $Et_2O$ (3×15 mL), dried over $MgSO_4$, and the solvent was removed under vacuum. If required, the final product was purified by chromatography on $SiO_2$.

Figure 25A:
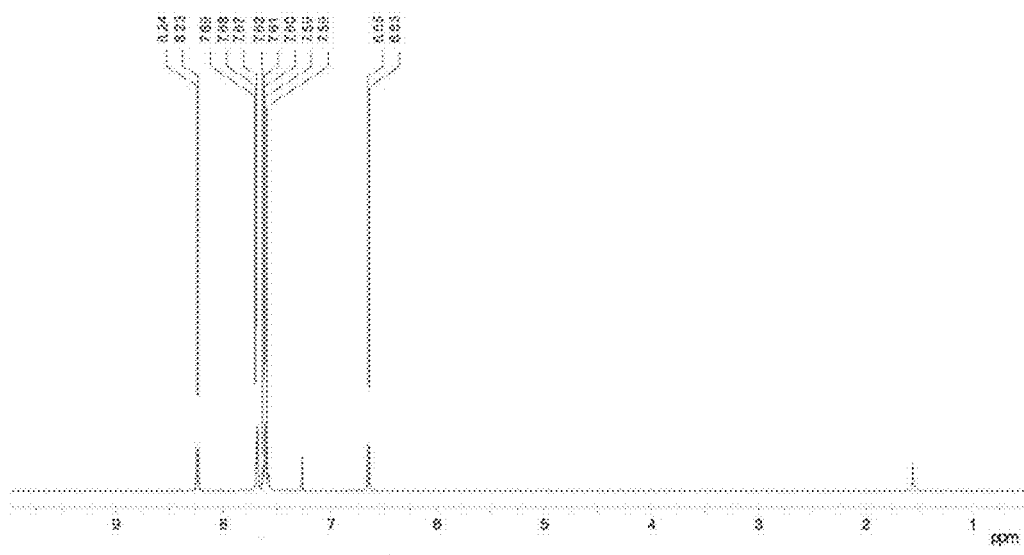
FIGS. 25A and 25B are $^1$H NMR and $^{13}$C NMR spectra, respectively, of an H$_2$S-reactive compound embodiment disclosed herein.
Figure 25B:
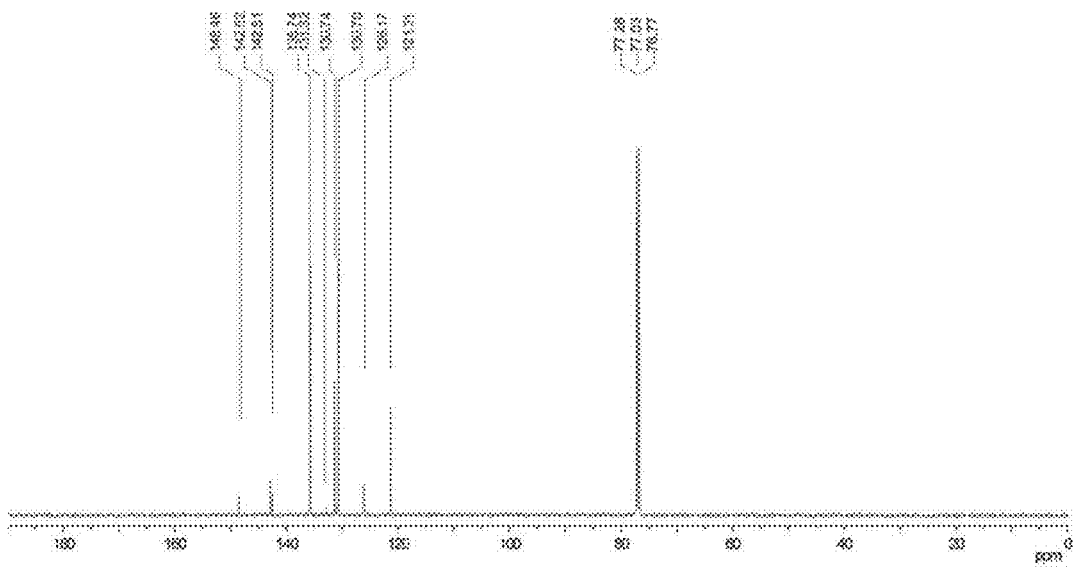

4-Nitro-7-(phenylthio)benzo[c][1,2,5]oxadiazole (colorimetric compound precursor 112). Purified by $SiO_2$ chromatography (100% $CH_2Cl_2$) to yield a dark orange powder. Yield: 31.0 mg, 76%. TLC $R_f$=0.71 ($SiO_2$, $CH_2Cl_2$). $^1$H NMR (500 MHz, $CDCl_3$) δ: 8.24 (d, J=8.3 Hz, 1H), 7.68 (d, J=7.8 Hz, 2H), 7.60 (m, 3H), 6.64 (d, J=7.8 Hz, 1H). $^{13}$C{1H} NMR (125 MHz, $CDCl_3$) δ: 148.4, 142.8, 142.5, 135.7, 131.3, 130.7, 130.7, 126.2, 121.3. Elemental Analysis: calcd (%) for $C_{12}H_7N_3O_3S$: C, 52.74; H, 2.58; N, 15.38. Found: C, 52.51; H, 2.80; N, 15.09. The corresponding $^1$H NMR and $^{13}$C NMR spectra are provided in FIGS. 25A and 25B, respectively.

Figure 26A:
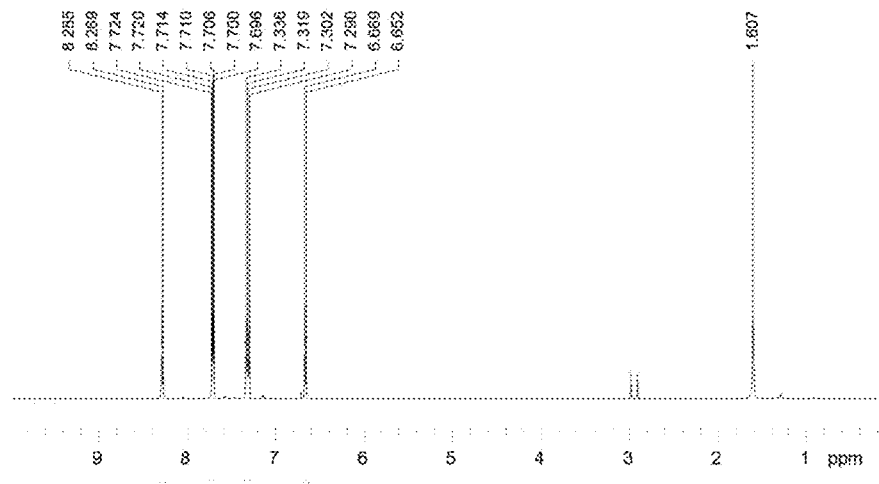
FIGS. 26A and 26B are $^1$H NMR and $^{13}$C NMR spectra, respectively, of an H$_2$S-reactive compound embodiment disclosed herein.
Figure 26B:
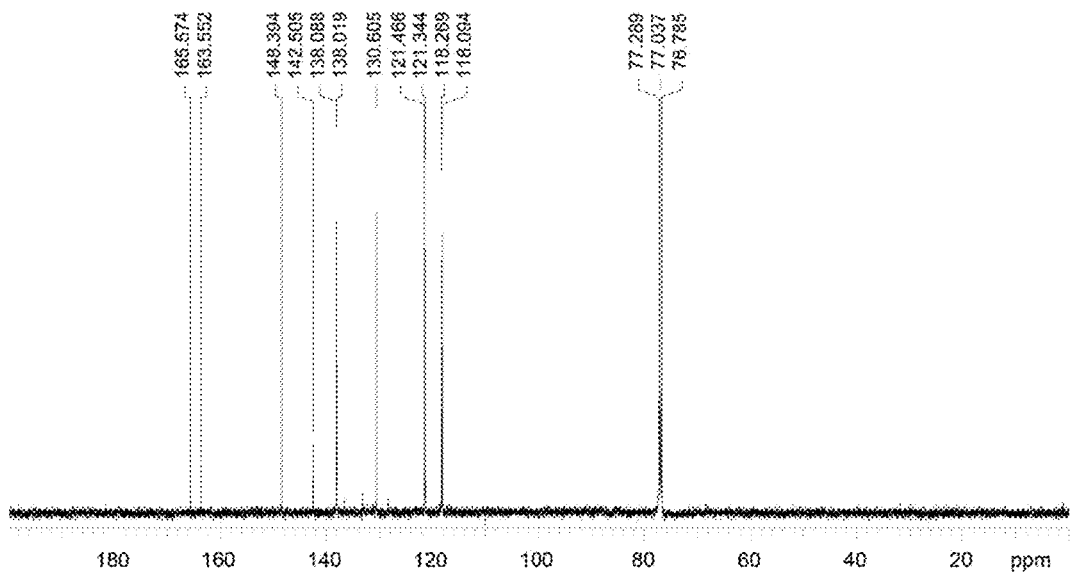

4-(4-Fluorophenylthio)-7-nitrobenzo[c][1,2,5]oxadiazole (colorimetric compound precursor 110). Purified by $SiO_2$ chromatography (100% $CH_2Cl_2$) to yield a yellow powder. Yield: 19.5 mg, 45%. TLC $R_f$=0.72 ($SiO_2$, 3:1 hexanes: EtOAc). $^1$H NMR (500 MHz, $CDCl_3$) δ: 8.29 (d, J=8.3 Hz, 1H), 7.72 (m, 2H), 7.34 (m, 2H), 6.67 (d, J=8.3 Hz, 1H). $^{13}$C{1H} NMR (125 MHz, $CDCl_3$) δ: 164.6 ($^1J_{CF}$=249 Hz), 148.4 142.5, 138.1 ($^4J_{CF}$=8.3 Hz), 133.1, 130.6, 128.3, 121.4, 121.3, 118.2 ($^3J_{CF}$=25.3 Hz). Elemental Analysis: calcd (%) for $C_{12}H_6FN_3O_3S \cdot 0.5H_2O$: C, 48.00; H, 2.35; N, 13.99. Found: C, 48.42; H, 2.18; N, 14.13. The corresponding $^1$H NMR and $^{13}$C NMR spectra are provided in FIGS. 26A and 26B, respectively.

Figure 27A:
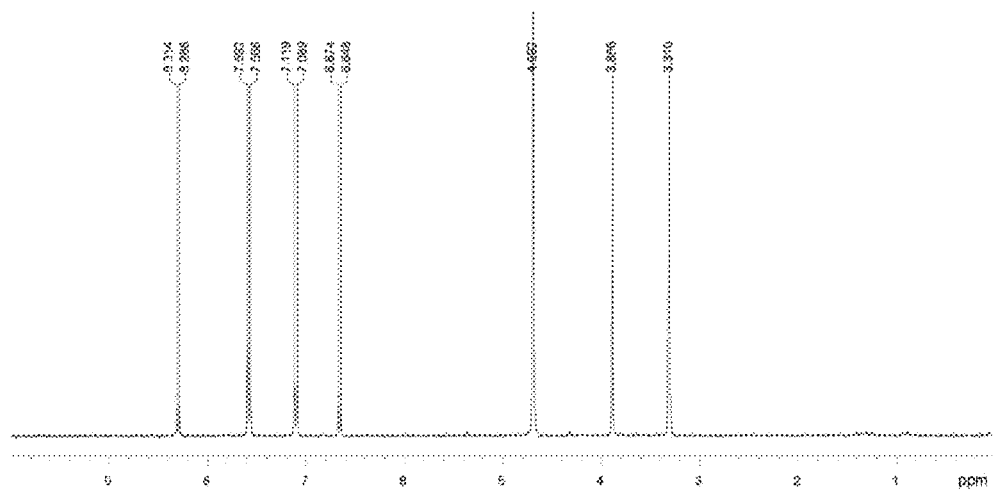
FIGS. 27A and 27B are $^1$H NMR and $^{13}$C NMR spectra, respectively, of an H$_2$S-reactive compound embodiment disclosed herein.
Figure 27B:
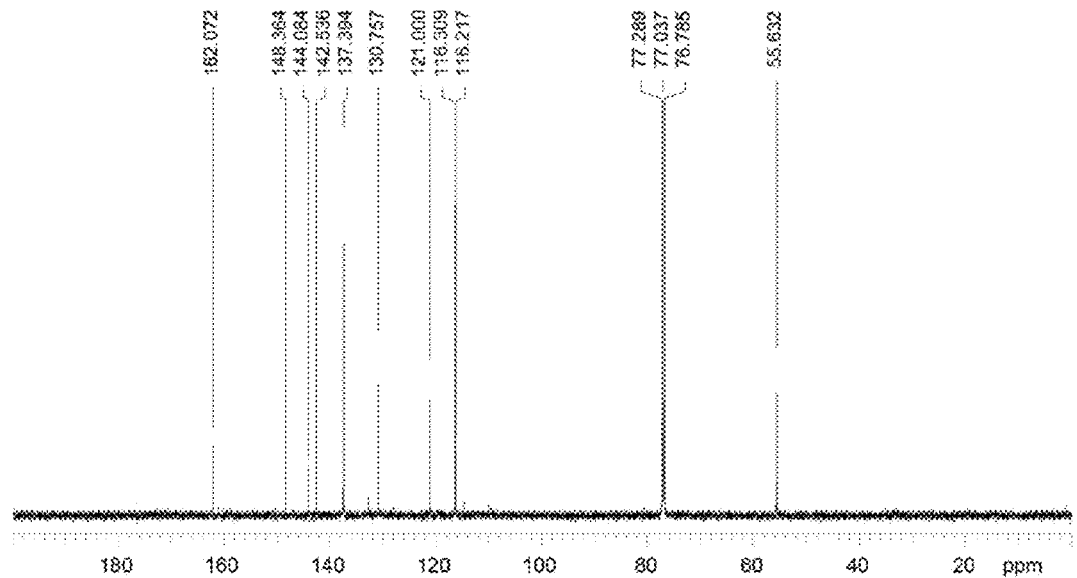

4-(4-Methoxyphenylthio)-7-nitrobenzo[c][1,2,5]oxadiazole (colorimetric compound precursor 114), a dark orange powder. Yield: 20.8 mg, 46%. TLC $R_f$=0.51 ($SiO_2$, 3:1 hexanes:EtOAc). $^1$H NMR (500 MHz, 3:1 MeOD:$CDCl_3$) δ: 8.31 (d, J=7.8 Hz, 1H), 7.59 (d, J=7.3 Hz, 2H), 7.11 (d, J=8.8 Hz, 2H), 6.67 (d, J=7.8 Hz, 1H), 3.89 (s, 3H, OMe). $^{13}$C{1H} NMR (125 MHz, $CDCl_3$) δ: 162.1, 148.4, 144.1, 142.5, 137.4, 132.7, 130.8, 121.0, 116.3, 116.2, 55.6. Elemental Analysis: calcd (%) for $C_{13}H_9N_3O_4S$: C, 51.48; H, 2.99; N, 13.85. Found: C, 51.39; H, 3.00; N, 13.79. The corresponding $^1H$ NMR and $^{13}C$ NMR spectra are provided in FIGS. 27A and 27B, respectively.

Figure 28A:
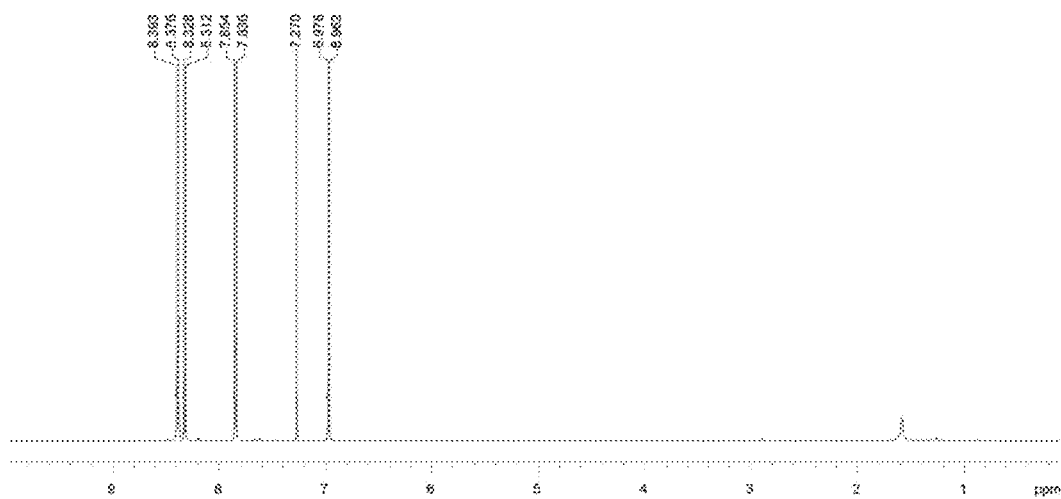
FIGS. 28A and 28B are $^1$H NMR and $^{13}$C NMR spectra, respectively, of an H$_2$S-reactive compound embodiment disclosed herein.
Figure 28B:
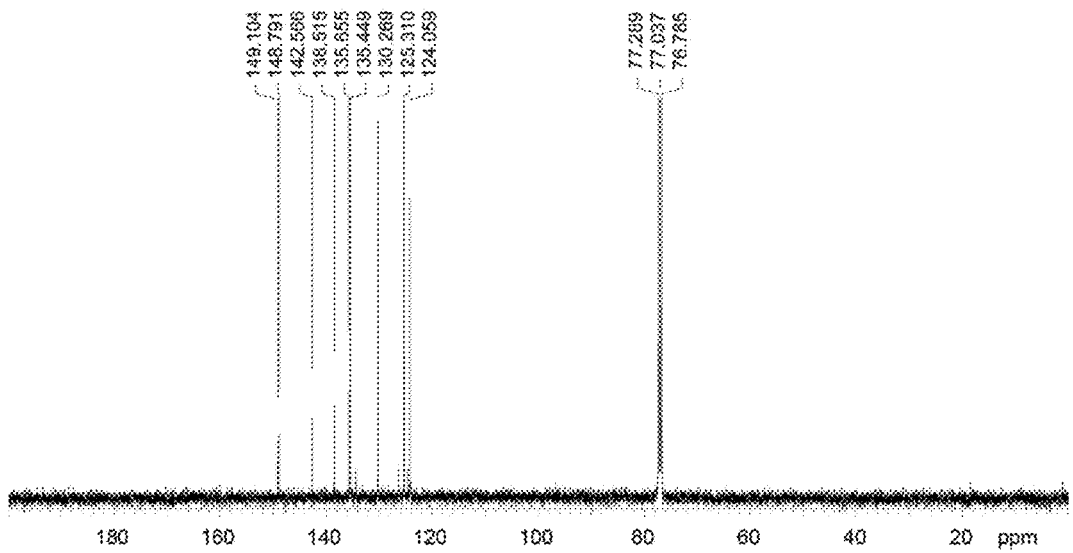

4-Nitro-7-(4-nitrophenylthio)benzo[c][1,2,5]oxadiazole (colorimetric compound precursor 116), a yellow powder. Yield: 30.0 mg, 64%. TLC $R_f$=0.73 ($SiO_2$, $CH_2Cl_2$). $^1H$ NMR (500 MHz, $CDCl_3$) δ: 8.39 (d, J=8.3 Hz, 2H), 8.32 (d, J=7.8 Hz, 1H), 7.85 (d, J=8.8 Hz, 2H), 6.98 (d, J=7.8 Hz, 1H). $^{13}C\{1H\}$ NMR (125 MHz, $CDCl_3$) δ: 149.1, 148.8, 142.6, 138.5, 135.5, 130.3, 126.4, 125.3, 124.5, 124.1. Elemental Analysis: calcd (%) for $C_{12}H_6N_4O_5S$: C, 45.29; H, 1.90; N, 17.60. Found: C, 44.90; H, 1.99; N, 17.35. The corresponding $^1H$ NMR and $^{13}C$ NMR spectra are provided in FIGS. 28A and 28B, respectively.

Chemiluminescent Testing Methods

General Synthetic/Analytical Procedures

Synthetic precursors 3-aminophthalhydrazide and 4-aminophthalhydrazide were purchased from TCI and used as received. Tetrabutylammonium amino acid salts (TBA-Ser, TBA-Val), HSN-2, $DsN_3$, and C-7Az were prepared according to methods known in the art. Deuterated solvents were purchased from Cambridge Isotope Laboratories and used as received. Piperazine-N,N'-bis(2-ethansulfonic acid) (PIPES, Aldrich) and potassium chloride (99.999%, Aldrich) were used to make buffered solutions (50 mM PIPES, 100 mM KCl, pH 7.4) with Millipore water. Buffered solutions were degassed by vigorous sparging with $N_2$ and stored in an inert atmosphere glove box. Anhydrous sodium hydrogen sulfide (NaSH) was purchased from Strem Chemicals and handled under nitrogen. S-Nitroso-N-acetyl-DL-penicillamine (SNAP), sodium peroxynitrite ($NaO_2NO$), and Angeli's salt ($NaN_2O_3$) were purchased from Cayman Chemical and stored either at −30 or −80° C. prior to use. L-Cysteine, N-acetyl-L-cysteine, and DL-homocysteine were purchased from TCI. Reduced glutathione was purchased from Aldrich. Stock solutions of the reactive species were prepared in either buffer or DMSO under nitrogen immediately prior to use and were introduced into buffered solutions with a syringe. Note: Although chemiluminescent compound precursors 200 and 202 are not air-sensitive, some of the reactive sulfur, oxygen, and nitrogen species, including $H_2S$, are known to react with oxygen. To ensure accurate measurements and to prevent decomposition of potentially-reactive species, experiments were performed under an inert atmosphere unless otherwise indicated. Both chemiluminescent compound precursors 200 and 202 react with $H_2S$ under aerobic conditions to provide equivalent results as under anhydrous conditions. Stock solutions of the chemiluminescent compound precursors (10 mM) were prepared in DMSO and stored below −20° C. until immediately prior to use. In all spectroscopic experiments, the final concentration of DMSO was less than 0.5% of the total buffer volume.

Spectroscopic Methods:

NMR spectra were acquired on a Brüker Avance-III-HD 600 spectrometer with a Prodigy multinuclear broadband CryoProbe at 25.0° C. Chemical shifts are reported in parts per million (δ) and are referenced to residual protic solvent resonances. The following abbreviations are used in describing NMR couplings: (s) singlet, (d) doublet, (b) broad, and (m) multiplet. IR spectra were measured on a Thermo Scientific Nicolet 6700 RT-IR using an ATR attachment. Chemiluminescence measurements were obtained on a Photon Technology International Quanta Master 40 spectrofluorimeter equipped with a Quantum Northwest TLC-50 temperature controller at 37.0±0.05° C. Chemiluminescent measurements were made under an inert atmosphere in septum-sealed cuvettes obtained from Starna Scientific and were repeated at least in triplicate. High resolution mass spectrometry (HRMS) measurements were performed by the Biomolecular Mass Spectrometry Core of the Environmental Health Sciences Core Center at Oregon State University. Melting points were obtained using a Laboratory Devices Mel-Temp and are reported uncorrected.

General Procedure for NMR Titrations:

A septum-sealed NMR tube was charged with either chemiluminescent compound precursor 200 or 202 (10 mM in 300 μL of DMSO-d6) and aliquots of a DMSO-d6 solution containing 200 mM amino acid mixed with 10 mM of the compound were added using a syringe. The chemical shifts of the aromatic proton resonances were tracked and the data were fitted to a 1:1 binding model.

Computational Details:

Calculations were performed using the Gaussian 09 software package with the GaussView graphical user interface. Graphical representations were produced using VMD v1.9. Geometry optimizations and unscaled frequency calculations were carried out at the B3LYP/6-311++G(d,p) level of theory using the IEF-PCM solvation model for water. Frequency calculations were performed on all converged structures to confirm that they corresponded to local minima. Calculated enthalpies are reported as zero-point corrected enthalpies. Initial structures for geometry optimizations were as follows: Each luminol tautomer was optimized starting with multiple azide orientations. For cysteine-luminol adducts, each luminol tautomer was optimized with the $RCO_2H/RNH_2$ and $RCO_2^-/RNH_3^+$ protonation states, multiple azide orientations, and multiple cysteine dihedral angles. The lowest energy conformer/tautomer was used to compare the relative energetics of the calculated species.

General Procedure for Luminescence Measurements:

In a septum-sealed cuvette, a solution of the compound (50 μM) and the desired reactive species was incubated in PIPES buffer (50 mM PIPES, 100 mM KCl, pH 7.4) for 60 minutes at 37.0° C. After incubation, 40 μL of 6 M NaOH was added to increase the pH to an optimal level for luminol chemiluminescence. After pH adjustment, 10 μL of 10 U/mL Horseradish Peroxidase (HRP) with 0.2 μM p-iodophenol was added. A background reading was acquired for 60 seconds, after which 50 μL of $H_2O_2$ (35%) was added. The sample luminosity at 425 nm was integrated for 300 s after $H_2O_2$ addition. The data reported are the average of at least three independent experiments.

General Procedure for Photoactivation Experiments:

In a septum sealed cuvette, a 5 μM solution of each fluorophore (HSN2, DNS-Az, and C-7Az) in PIPES buffer (50 mM PIPES, 100 mM KCl, pH 7.4) was excited at the absorption maximum of the corresponding amine product for 25 minutes at 37° C. The samples were detected at the emission maximum for the unprotected fluorophore with excitation and emission slit widths set at 5 nm and 1.4 nm, respectively. The normalized data are presented in FIG. 5.

General Procedure for Enzymatically Produced $H_2S$ Luminescence Measurements:

In a septum sealed cuvette, the desired reactive species were incubated in PIPES buffer (50 mM PIPES, 100 mM KCl, pH 7.4) at 37.0° C. for 48 hours. After initial incubation, 15 μL of 10 mM chemiluminescent compound precursor 202 in DMSO was added, and allowed to react for 60 min. After incubation, 40 μL of 6 M NaOH was added to increase the pH to an optimal level for luminol chemiluminescence. After pH adjustment, 10 μL of 10 U/mL Horseradish Peroxidase (HRP) with 0.2 μM p-iodophenol was added. A background reading was acquired for 60 s, after which 50 μL of $H_2O_2$ (35%) was added. The sample luminosity at 425 nm was integrated for 40 s after $H_2O_2$ addition. The data reported are the average of at least three independent experiments.

Cell Culture and Lysing Procedure:

C6 cells were obtained from ATCC and cultured in Dulbecco's Modified Eagle Medium (DMEM, Cellgro, MediaTek, Inc.) supplemented with 10% fetal bovine serum (FBS, HyClone), and 1% penicillin/streptomycin. Cells were passed and plated into T-75 flasks containing 10 mL of DMEM, and incubated at 37° C. with 5% $CO_2$. For luminescence studies, the cells were washed with 1× phosphate buffered saline (PBS), trypsinized with 5 mL of Trypsin, and then centrifuged to form a cell pellet. The cell pellet was resuspended in 5 mL of 1×PBS and the cells were counted using a Bio RAD TC20 automated cell counter. Cells were centrifuged at 1,000 RPM for 5 minutes at room temperature, placed on ice and lysed using 100 μL of RIPA buffer (pH 7.5 10 mM Tris-HCl, 150 mM NaCl, 1.0% Nonidet P-40, 0.1% SDS, 0.1% sodium deoxycholate) containing protease inhibitor (PhosSTOP, Roche) for every 2×10⁶ cells in the pellet. Luminescence measurements on cell lysates were made using 100 μL of lysate solution (2×10⁶ cells per experiment) under ambient atmosphere by following the general procedure for enzymatically produced $H_2S$ outlined above.

Example 8

In this particular embodiment, the use of a compound for a chemiluminescent testing method is disclosed. In the absence of $H_2S$, treatment of compound 200 and compound 202 with HRP and $H_2O_2$ resulted in negligible chemiluminescence by comparison to luminol or isoluminol. By contrast, $H_2S$-mediated reduction of compound 200 or compound 202, followed by treatment with HRP and $H_2O_2$ generated a robust chemiluminescent response which, depending on the concentration, can be monitored spectroscopically (FIG. 9) or by the naked eye (FIG. 8).

Following the $H_2S$-derived chemiluminescent response of both chemiluminescent compound precursor 200 and chemiluminescent compound precursor 202, the detection limit of each chemiluminescent compound precursor for $H_2S$ was determined. After incubating each chemiluminescent compound precursor for 1 hour for different $H_2S$ concentrations, the chemiluminescent response was measured after treatment with $H_2O_2$/HRP using p-iodophenol as an enhancer. A linear chemiluminescent response was observed for both chemiluminescent compound precursor 200 (FIG. 29) and chemiluminescent compound precursor 202 (FIG. 30), thereby demonstrating the ability of each chemiluminescent compound precursor to quantify different $H_2S$ concentrations. Based on the concentration-dependent $H_2S$ response and the instrumental background measurements, the $H_2S$ detection limit (3σ) of chemiluminescent compound precursor 200 and chemiluminescent compound precursor 202 was determined to be 0.7±0.3 μM and 4.6±2.0 μM, respectively. Although the total brightness of chemiluminescent compound precursor 202 was lower than that of compound 200, both these detection limits were below the reported range of $H_2S$ concentrations (20 μM-100 μM) found in mammalian blood. The effective concentration range where chemiluminescent compound precursor 200 and chemiluminescent compound precursor 202 were been shown to accurately detect $H_2S$ cover this entire range.

Example 9

The response of chemiluminescent compound precursor 200 and chemiluminescent compound precursor 202 to biologically-relevant reactive sulfur, oxygen, and nitrogen species (RSONS) was also determined. The selectivity of chemiluminescent compound precursor 200 for $H_2S$ was determined by adding 33 equivalents of cysteine (Cys), homocysteine (Hcy), N-acetylcysteine (NAC), reduced glutathione (GSH), thiosulfate ($S_2O_3^{2-}$), sulfate ($SO_4^{2-}$), nitric oxide (NO), nitroxyl (HNO), and nitrite ($NO_2^-$) (FIGS. 10 and 11). Chemiluminescent compound precursor 200 showed a 128-fold turn on for $H_2S$ and high selectivity for $H_2S$ over oxygen and nitrogen reactive species; whereas less selectivity was observed with cysteine-derived reductants. Results are provided below in Table 4.

TABLE 4

| | Normalized Luminescence ($CL/CL_0$) | |
|---|---|---|
| Reactant | 200 | 202 |
| Blank | 1.0 ± 0.1 | 1.0 ± 0.3 |
| $H_2S$ | 128 ± 16 | 45 ± 3 |
| Cys | 81 ± 5 | 1.5 ± 0.03 |
| GSH | 94 ± 12 | 3.7 ± 0.9 |
| Hcy | 57 ± 3 | 3.3 ± 0.5 |
| NAC | 37 ± 19 | 3.3 ± 0.4 |
| Toluenethiol (TolSH) | 0.8 ± 0.1 | 1.9 ± 0.4 |
| 2-mercaptoethanol (2-ME) | 6.6 ± 3.2 | 1.7 ± 0.08 |
| $S_2O^{2-}$ | 5.9 ± 1.1 | 2.2 ± 0.6 |
| $SO_4^{2-}$ | 0.8 ± 0.3 | 1.5 ± 0.3 |
| $NO_2$ | 0.9 ± 0.2 | 3.2 ± 0.6 |
| SNAP (NO) | 0.05 ± 0.01 | 1.5 ± 0.5 |
| $ONOO^-$ | 0.6 ± 0.2 | 4.0 ± 0.2 |
| HNO | 9.1 ± 0.2 | 3.3 ± 0.2 |

Without being limited to a particular theory of operation, it is currently believed that the observed chemiluminescent response from cysteine-derived thiols could be due to hydrogen bonding of the amino acid substrate to the luminol hydrazide moiety. Such hydrogen bonding would increase the effective thiol concentration near the azide of chemiluminescent compound precursor 200 and orient the thiol toward attack on the azide. Treating chemiluminescent compound precursor 200 with toluenethiol (TolSH), which lacks an amino acid moiety to hydrogen bond with the luminol hydrazide, did not generate a chemiluminescent response from chemiluminescent compound precursor 200.

Furthermore, without being limited to a single theory of operation, it is currently believed that chemiluminescent compound precursor 202 could be more selective than chemiluminescent compound precursor 200 for $H_2S$ due to the increased distance to the azide group from the hydrazide moiety. In some embodiments, chemiluminescent compound precursor 202 showed a 45-fold turn on for $H_2S$ and high selectivity for $H_2S$ over other RSONS (FIG. 11).

Example 10

To further understand the reactivity differences between chemiluminescent compound precursors 200 and 202, and to substantiate the hydrogen-bonding model, DFT calculations at the B3LYP/6-311++G(d,p) level of theory were performed using the IEPCM water solvation model for each chemiluminescent compound precursor as well as cysteinecoordinated adducts. Cysteine was chosen as a model amino acid for these studies due to its differential reactivity toward chemiluminescent compound precursors 200 and 202 and also fewer available rotational and protonation states by comparison to GSH. To confirm that changes in the frontier orbital landscape of chemiluminescent compound precursors 200 and 202 were not responsible for the differential reactivity between the two compounds, the HOMO and LUMO of chemiluminescent compound precursor 200 and chemiluminescent compound precursor 202 were calculated. For both compounds, the HOMO and LUMO are localized exclusively on the azide, suggesting that orbital differences or LUMO accessibility is not the source of the differential reactivity between chemiluminescent compound precursors 200 and 202 (FIGS. 31A-31D).

The difference in activity also could be the result of thiol interaction with the hydrazide moiety. In a particular embodiment, cysteine was used as a model compound and optimized the geometry of the cysteine-bound adducts of both compound 30 and compound 31 (FIGS. 32A and 32B, respectively). To investigate whether amino acid derived thiol interaction with to the hydrazide moiety could contribute to the lower selectivity of chemiluminescent compound precursor 200, the geometry of the cysteine-bound adducts of both chemiluminescent compound precursors 200 and 202 were optimized. The luminol tautomers and cysteine protonation states were evaluated to ensure that broad potential energy surface was surveyed during the optimizations. The optimized geometry of the chemiluminescent compound precursor 200/Cys adduct corresponded to a geometry in which the cysteine is hydrogen-bonded to the hydrazide moiety and the cysteine thiol is situated 2.67 Å away from the azide nitrogen, suggesting a hydrogen bond between the —SH and the azide group. This hydrogen bond distance is consistent with crystallographically-characterized hydrogen bonds between N—H and O—H groups to the terminal nitrogen of azides. By contrast, the optimized geometry of the chemiluminescent compound precursor 202/Cys indicated that the thiol group from the cysteine may be too far away from the azide to result in a favorable hydrogen bonding interaction. These structures corresponding to the energy minima of the chemiluminescent compound precursor 200/Cys and chemiluminescent compound precursor 202/Cys adducts are consistent with the hypothesis that amino acid hydrogen bonding to the luminol hydrazide may dictate the observed selectivity differences for the two chemiluminescent compound precursors to thiol-containing amino acids.

Figure 33A:
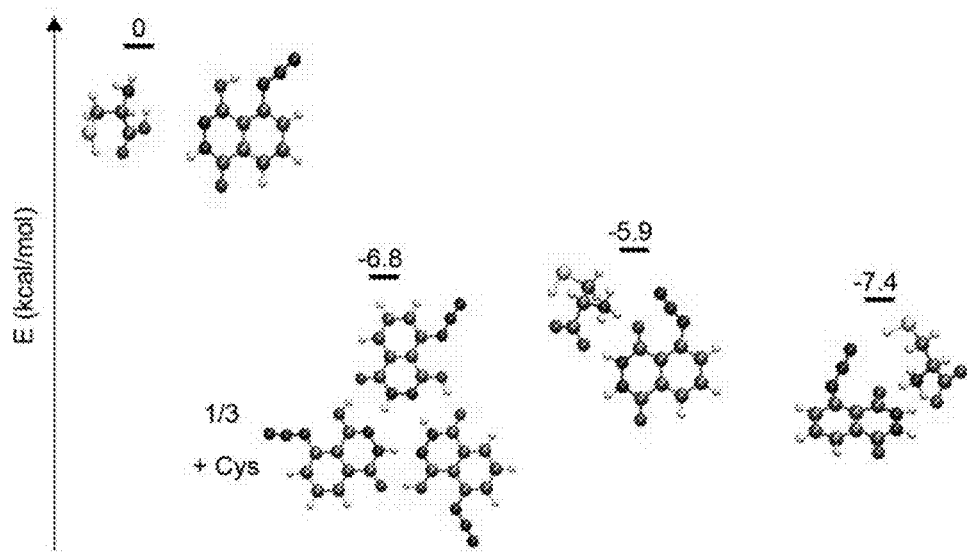
FIGS. 33A and 33B are energy diagrams of the interaction between one H$_2$S-reactive compound embodiment disclosed herein and cysteine (FIG. 33A) and the interaction between a different H$_2$S-reactive compound embodiment and cysteine (FIG. 33B).
Figure 33B:
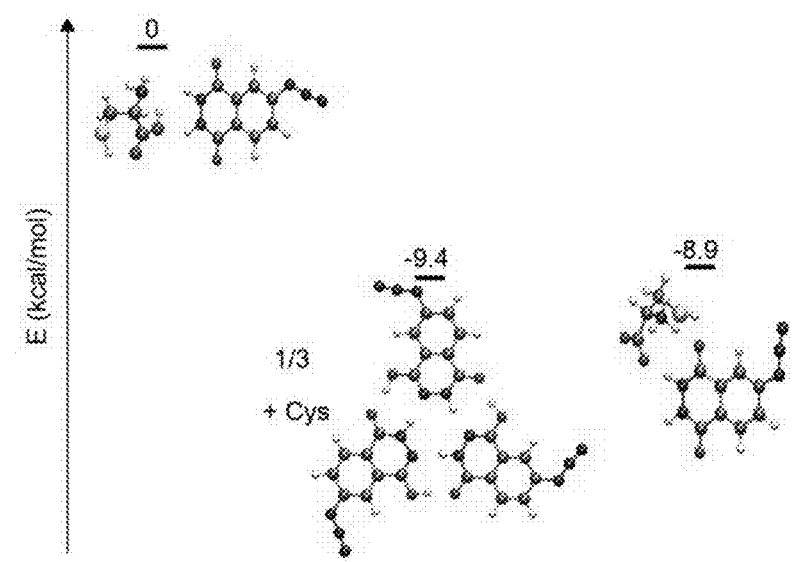

The energies of the hydrogen-bonded adducts to other species likely present in solution also were compared. Because phthalhydrazides typically adopt a trimeric form in the solid state, the hydrogen-bonded trimer for both chemiluminescent compound precursors 200 and 202 was also optimized. For chemiluminescent compound precursor 200, the chemiluminescent compound precursor 200/Cys adduct in which the amino acid moiety was bound to the hydrazide and the thiol group was hydrogen bonded to the terminal nitrogen of the azide was the global energy minimum (FIG. 33A). This conformation is 7.4 kcal/mol more stable than isolated chemiluminescent compound precursor 200 and cysteine, 1.5 kcal/mol more stable than the chemiluminescent compound precursor 200/Cys adduct minimum without an $SH/N_3$ hydrogen bond, and 0.7 kcal/mol more stable than the chemiluminescent compound precursor 200 trimer. By contrast, the structure of chemiluminescent compound precursor 202 does not allow for $SH/N_3$ hydrogen bonding during cysteine coordination because of the large interatomic distance between the thiol and the azide (FIG. 33B). In some embodiments, the chemiluminescent compound precursor 202/Cys adduct is 0.5 kcal/mol less stable than the chemiluminescent compound precursor 202 trimer. Taken together, the results of the computational studies of chemiluminescent compound precursors 200 and 202 are consistent with the hypothesis that hydrogen bonding of cysteine to the hydrazide and azide erodes the selectivity of chemiluminescent compound precursor 200. Not only do these results help explain the observed selectivity, but they also provide valuable design strategies for developing future generations of highly-selective $H_2S$ compound embodiments.

Example 11

Figure 35:
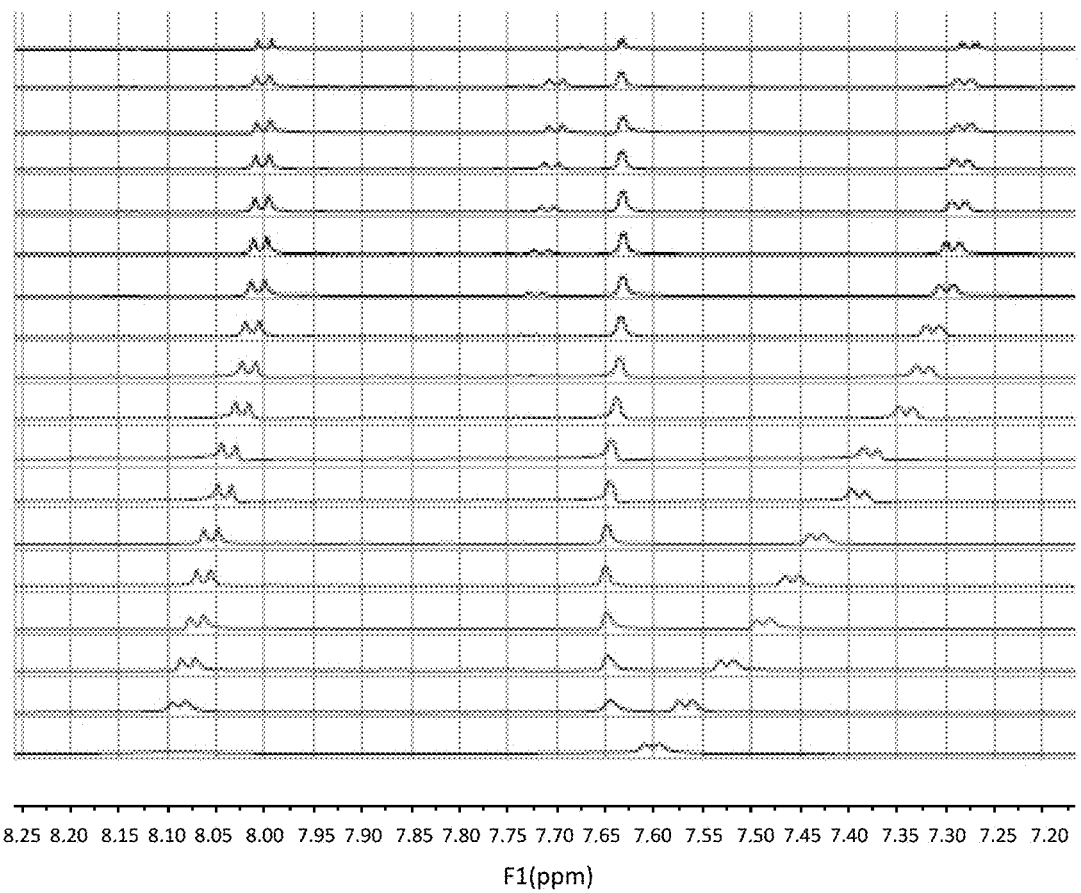
FIG. 35 is an image of stacked $^1$H NMR spectra showing changes in the aromatic region of an H$_2$S-reactive compound embodiment during the course of a titration with TBA-Ser.
Figure 36:
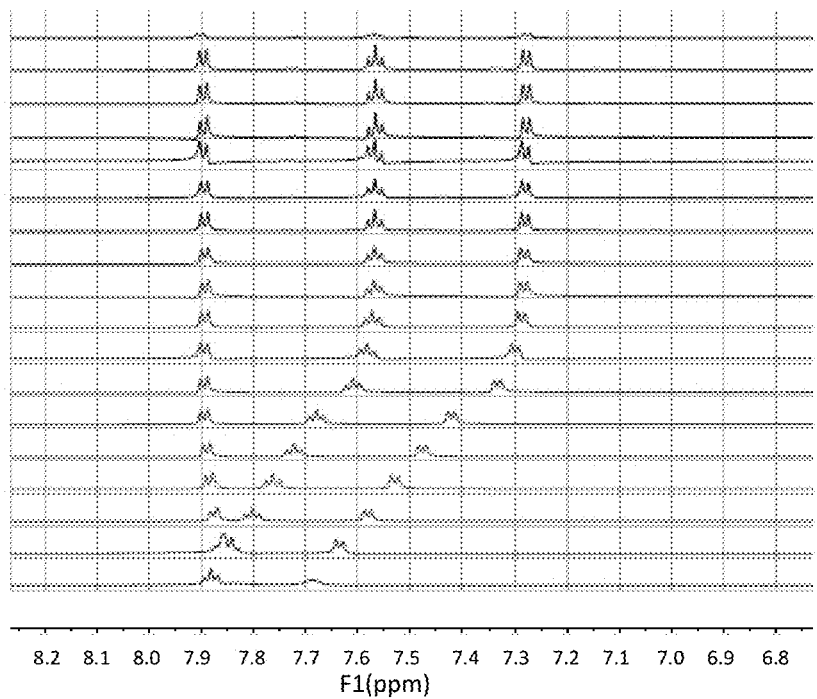
FIG. 36 is an image of stacked $^1$H NMR spectra showing changes in the aromatic region of an H$_2$S-reactive compound embodiment during the course of a titration with TBA-Val.
Figure 37:
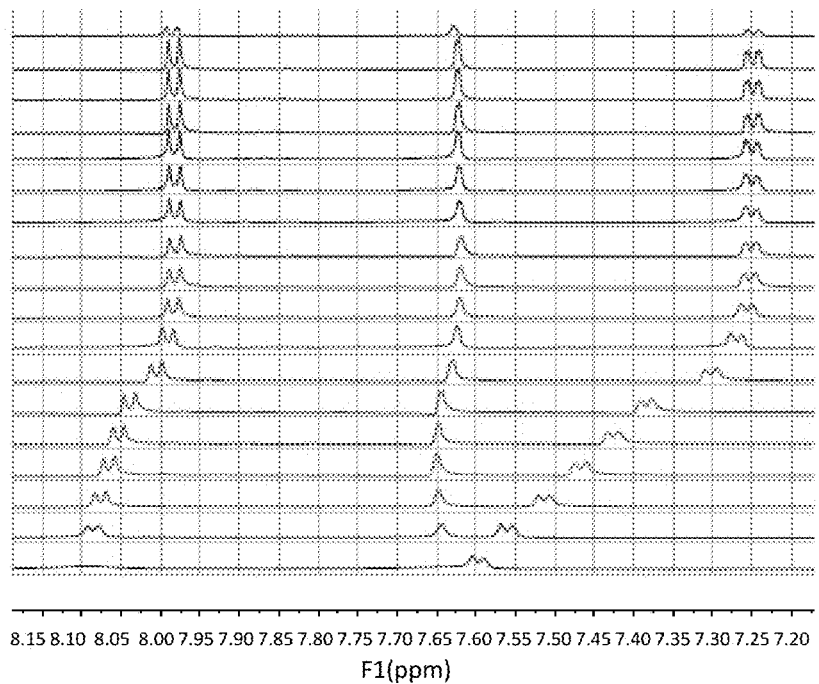
FIG. 37 is an image of stacked $^1$H NMR spectra showing changes in the aromatic region of the H$_2$S-reactive compound embodiment used to generate FIG. 35 during the course of a titration with TBA-Val.

In addition to computational evidence for the hydrogen-bonding hypothesis, NMR titrations of chemiluminescent compound precursors 200 and 202 were also performed with different amino acids to further validate the model with solution data. Serine was used as a model amino acid because cysteine quickly reduces chemiluminescent compound precursor 200 under typical experimental conditions. Furthermore, the alcohol side chain of serine maintains a hydrogen bond donor but, unlike cysteine, is redox inactive. $^1$H NMR titrations were performed in DMSO to ensure complete solubility of all components and to provide a hydrogen-bond disrupting environment similar to water. Similarly, to model the protonation state of the amino acids in water, and also to ensure complete solubility through the course of the titration, the tetrabutylammonium salts of each amino acid were prepared. By titrating tetrabutylammonium serine (TBA-Ser) into independent solutions of chemiluminescent compound precursors 200 and 202, striking changes in the aromatic region of the NMR spectra were observed, consistent with amino acid binding to the hydrazide moiety (FIGS. 34A-34C). Additional representative titrations are illustrated in FIGS. 35-37 and titration data are provided in Tables 5-8, below.

TABLE 5

Tabulated titration data for chemiluminescent compound precursor 200 with TBA-Ser.

| | | Run 1 | | Run 2 | | Run 3 | |
| --- | --- | --- | --- | --- | --- | --- | --- |
| [200] (M) | [TBA-Ser] (M) | Proton 1 (ppm) | Proton 2 (ppm) | Proton 1 (ppm) | Proton 2 (ppm) | Proton 1 (ppm) | Proton 2 (ppm) |
| 0.010091 | 0 | 7.883 | 7.687 | 7.881 | 7.685 | 7.898 | 7.694 |
| 0.010091 | 0.001353 | 7.847 | 7.643 | 7.841 | 7.636 | 7.84 | 7.634 |
| 0.010091 | 0.002688 | 7.818 | 7.602 | 7.805 | 7.587 | 7.803 | 7.583 |
| 0.010091 | 0.004006 | 7.789 | 7.563 | 7.775 | 7.548 | 7.772 | 7.542 |
| 0.010091 | 0.005307 | 7.766 | 7.533 | 7.751 | 7.514 | 7.748 | 7.51 |
| 0.010091 | 0.006591 | 7.746 | 7.507 | 7.731 | 7.485 | 7.727 | 7.482 |

TABLE 5-continued

Tabulated titration data for chemiluminescent compound precursor 200 with TBA-Ser.

| | | Run 1 | | Run 2 | | Run 3 | |
|---|---|---|---|---|---|---|---|
| [200] (M) | [TBA-Ser] (M) | Proton 1 (ppm) | Proton 2 (ppm) | Proton 1 (ppm) | Proton 2 (ppm) | Proton 1 (ppm) | Proton 2 (ppm) |
| 0.010091 | 0.00973 | 7.707 | 7.457 | 7.691 | 7.437 | 7.69 | 7.434 |
| 0.010091 | 0.01277 | 7.681 | 7.423 | 7.667 | 7.405 | 7.665 | 7.403 |
| 0.010091 | 0.018575 | 7.649 | 7.383 | 7.636 | 7.367 | 7.636 | 7.366 |
| 0.010091 | 0.024038 | 7.633 | 7.361 | 7.621 | 7.348 | 7.62 | 7.346 |
| 0.010091 | 0.029189 | 7.622 | 7.348 | 7.612 | 7.335 | 7.611 | 7.335 |
| 0.010091 | 0.040865 | 7.607 | 7.329 | 7.602 | 7.318 | 7.598 | 7.319 |
| 0.010091 | 0.051081 | 7.6 | 7.32 | 7.591 | 7.31 | 7.591 | 7.31 |
| 0.010091 | 0.068108 | 7.593 | 7.311 | 7.586 | 7.303 | 7.585 | 7.302 |
| 0.010091 | 0.08173 | 7.589 | 7.307 | 7.584 | 7.299 | 7.583 | 7.298 |
| 0.010091 | 0.092874 | 7.587 | 7.303 | 7.582 | 7.297 | 7.581 | 7.296 |
| 0.010091 | 0.102162 | 7.587 | 7.302 | 7.58 | 7.296 | 7.579 | 7.294 |
| 0.010091 | 0.204324 | 7.579 | 7.287 | 7.576 | 7.288 | 7.577 | 7.287 |

TABLE 6

Tabulated titration data for chemiluminescent compound precursor 202 with TBA-Ser.

| | | Run 1 | | Run 2 | | Run 3 | |
|---|---|---|---|---|---|---|---|
| [202] (M) | [TBA-Ser] (M) | Proton 1 (ppm) | Proton 2 (ppm) | Proton 1 (ppm) | Proton 2 (ppm) | Proton 1 (ppm) | Proton 2 (ppm) |
| 0.010091 | 0 | 7.598 | 8.094 | 7.599 | 8.109 | 7.601 | 8.093 |
| 0.010091 | 0.001339 | 7.577 | 8.088 | 7.568 | 8.087 | 7.567 | 8.088 |
| 0.010091 | 0.00266 | 7.542 | 8.082 | 7.515 | 8.074 | 7.525 | 8.077 |
| 0.010091 | 0.003964 | 7.509 | 8.075 | 7.47 | 8.063 | 7.487 | 8.07 |
| 0.010091 | 0.005252 | 7.482 | 8.069 | 7.438 | 8.054 | 7.458 | 8.063 |
| 0.010091 | 0.006522 | 7.455 | 8.061 | 7.416 | 8.048 | 7.432 | 8.056 |
| 0.010091 | 0.009628 | | | 7.389 | | | 8.042 |
| 0.010091 | 0.012636 | 7.383 | 8.039 | 7.354 | 8.026 | 7.377 | 8.036 |
| 0.010091 | 0.01838 | 7.35 | 8.027 | 7.326 | 8.016 | 7.341 | 8.024 |
| 0.010091 | 0.023786 | 7.33 | 8.021 | 7.313 | 8.011 | 7.323 | 8.018 |
| 0.010091 | 0.028883 | 7.321 | 8.016 | 7.304 | 8.006 | 7.313 | 8.014 |
| 0.010091 | 0.040437 | 7.304 | 8.009 | 7.294 | 8.004 | 7.299 | 8.007 |
| 0.010091 | 0.050546 | 7.297 | 8.008 | 7.288 | 8.003 | 7.292 | 8.005 |
| 0.010091 | 0.067395 | 7.291 | 8.004 | 7.283 | 7.999 | 7.286 | 8.004 |
| 0.010091 | 0.080874 | 7.287 | 8.003 | 7.28 | 7.999 | 7.2835 | 8.003 |
| 0.010091 | 0.091902 | | | 7.278 | 7.999 | 7.2815 | 8.002 |
| 0.010091 | 0.101092 | | | 7.277 | 7.998 | 7.28 | 8.002 |
| 0.010091 | 0.202184 | 7.275 | 7.999 | 7.276 | 7.998 | 7.275 | 8.001 |

TABLE 7

Tabulated titration data for chemiluminescent compound precursor 200 with TBA-Val

| | | Run 1 | | Run 2 | | Run 3 | |
|---|---|---|---|---|---|---|---|
| [200] (M) | [TBA-Val] (M) | Proton 1 (ppm) | Proton 2 (ppm) | Proton 1 (ppm) | Proton 2 (ppm) | Proton 1 (ppm) | Proton 2 (ppm) |
| 0.010091 | 0 | 7.881 | 7.685 | 7.884 | 7.686 | 7.883 | 7.684 |
| 0.010091 | 0.001427 | 7.841 | 7.635 | 7.843 | 7.638 | 7.838 | 7.629 |
| 0.010091 | 0.002835 | 7.801 | 7.581 | 7.802 | 7.582 | 7.796 | 7.573 |
| 0.010091 | 0.004225 | 7.762 | 7.528 | 7.765 | 7.532 | 7.755 | 7.518 |
| 0.010091 | 0.005597 | 7.722 | 7.475 | 7.728 | 7.483 | 7.716 | 7.468 |
| 0.010091 | 0.006951 | 7.679 | 7.422 | 7.686 | 7.43 | 7.675 | 7.414 |
| 0.010091 | 0.01026 | 7.609 | 7.332 | 7.61 | 7.333 | 7.606 | 7.329 |
| 0.010091 | 0.013467 | 7.581 | 7.298 | 7.582 | 7.3 | 7.583 | 7.299 |
| 0.010091 | 0.019588 | 7.571 | 7.285 | 7.573 | 7.288 | 7.575 | 7.289 |
| 0.010091 | 0.025349 | 7.569 | 7.282 | 7.57 | 7.283 | 7.573 | 7.287 |
| 0.010091 | 0.030781 | 7.569 | 7.282 | 7.569 | 7.282 | 7.571 | 7.284 |
| 0.010091 | 0.043093 | 7.568 | 7.281 | 7.567 | 7.28 | 7.571 | 7.283 |
| 0.010091 | 0.053867 | 7.567 | 7.279 | 7.567 | 7.28 | 7.571 | 7.282 |

TABLE 7-continued

Tabulated titration data for chemiluminescent compound precursor 200 with TBA-Val

| | | Run 1 | | Run 2 | | Run 3 | |
|---|---|---|---|---|---|---|---|
| [200] (M) | [TBA-Val] (M) | Proton 1 (ppm) | Proton 2 (ppm) | Proton 1 (ppm) | Proton 2 (ppm) | Proton 1 (ppm) | Proton 2 (ppm) |
| 0.010091 | 0.071822 | 7.567 | 7.279 | 7.567 | 7.279 | 7.571 | 7.282 |
| 0.010091 | 0.086187 | 7.566 | 7.277 | 7.567 | 7.279 | 7.571 | 7.282 |
| 0.010091 | 0.097939 | 7.566 | 7.277 | 7.567 | 7.279 | 7.571 | 7.282 |
| 0.010091 | 0.107733 | | | 7.566 | 7.277 | 7.567 | 7.279 |
| 0.010091 | 0.215466 | 7.566 | 7.277 | 7.567 | 7.279 | 7.568 | 7.277 |

TABLE 8

Tabulated titration data for chemiluminescent compound precursor 202 with TBA-Val.

| | | Run 1 | | Run 2 | | Run 3 | |
|---|---|---|---|---|---|---|---|
| [202] (M) | [TBA-Val] (M) | Proton 1 (ppm) | Proton 2 (ppm) | Proton 1 (ppm) | Proton 2 (ppm) | Proton 1 (ppm) | Proton 2 (ppm) |
| 0.010152 | 0 | 8.101 | 7.598 | 8.103 | 7.6 | 8.092 | 7.597 |
| 0.010152 | 0.001367 | 8.088 | 7.563 | 8.088 | 7.564 | 8.084 | 7.559 |
| 0.010152 | 0.002715 | 8.079 | 7.519 | 8.082 | 7.521 | 8.075 | 7.513 |
| 0.010152 | 0.004046 | 8.067 | 7.476 | 8.067 | 7.476 | 8.066 | 7.467 |
| 0.010152 | 0.00536 | 8.058 | 7.433 | 8.056 | 7.433 | 8.053 | 7.424 |
| 0.010152 | 0.006657 | 8.04 | 7.382 | 8.04 | 7.386 | 8.039 | 7.382 |
| 0.010152 | 0.009827 | 8.005 | 7.298 | 8.005 | 7.304 | 8.003 | 7.3 |
| 0.010152 | 0.012897 | 7.993 | 7.271 | 7.991 | 7.269 | 7.99 | 7.268 |
| 0.010152 | 0.01876 | 7.986 | 7.258 | 7.983 | 7.256 | 7.984 | 7.256 |
| 0.010152 | 0.024277 | 7.986 | 7.257 | 7.982 | 7.254 | 7.981 | 7.252 |
| 0.010152 | 0.02948 | | | 7.982 | 7.252 | 7.981 | 7.252 |
| 0.010152 | 0.041271 | 7.985 | 7.253 | 7.982 | 7.252 | 7.981 | 7.251 |
| 0.010152 | 0.051589 | 7.985 | 7.253 | 7.982 | 7.252 | 7.981 | 7.251 |
| 0.010152 | 0.068786 | 7.985 | 7.253 | 7.982 | 7.252 | 7.981 | 7.25 |
| 0.010152 | 0.082543 | 7.985 | 7.252 | 7.982 | 7.25 | 7.981 | 7.249 |
| 0.010152 | 0.093799 | 7.984 | 7.252 | 7.982 | 7.25 | 7.981 | 7.249 |
| 0.010152 | 0.103178 | 7.984 | 7.252 | 7.982 | 7.25 | 7.981 | 7.248 |
| 0.010152 | 0.206357 | 7.984 | 7.252 | 7.982 | 7.25 | 7.981 | 7.248 |

Control experiments to investigate dilution effects on chemiluminescent compound precursors 200 and 202, as well as self-association studies of TBA-Ser did not result in shifts in the aromatic region of the spectrum. These changes in the $^1$H NMR shifts were fit to a 1:1 binding model using the Thordarson fitting program to afford binding affinities of 380±80 M$^{-1}$ and 260±60 M$^{-1}$ for chemiluminescent compound precursor 200/TBA-Ser and chemiluminescent compound precursor 202/TBA-Ser, respectively (Table 9). The slightly tighter binding of TBA-Ser to chemiluminescent compound precursor 200 over chemiluminescent compound precursor 202 is consistent with the computational studies and the proposed hydrogen bonding model.

TABLE 9

Binding affinities for chemiluminescent compound precursors 200 and 202 with model amino acids[a]

| | Binding Affinities (M$^{-1}$) | |
|---|---|---|
| | 200 | 202 |
| TBA-Ser | 380 ± 80 | 260 ± 60 |
| TBA-Val | 3640 ± 270 | 3780 ± 370 |

[a]Conditions: 10.0 mM probe, 0-200 mM amino acid, DMSO-d6, 25.0° C. Each value represents the average of three independent titrations.

$^1$H NMR titrations with tetrabutylammonium valine (TBA-Val) were also performed as a second model system in which the side chain of the amino acid cannot hydrogen bond to the azide. As observed with TBA-Ser, TBA-Val binds to both chemiluminescent compound precursor 200 and chemiluminescent compound precursor 202 in a 1:1 stoichiometry with binding affinities of 3640±270 M$^{-1}$ and 3780±370 M$^{-1}$ for chemiluminescent compound precursors 200 and 202, respectively. The binding affinities measured for TBA-Val are larger than for TBA-Ser (Table 9), which is consistent with the reduced internal competition for intramolecular hydrogen bonding sites in valine. Based on these titration data, and the lower hydrogen bonding ability of thiols by comparison to alcohols, binding affinity of cysteine for chemiluminescent compound precursor 200 and 202 was expected to be between the measured values for serine and valine. Under the general experimental conditions used to measure the selectivity date, a 10$^3$-10$^4$ M$^{-1}$ binding affinity between Cys/chemiluminescent compound precursor 200 would result in significant generation of the Cys/chemiluminescent compound precursor 200 adduct, which is consistent with the observed erosion in selectivity. The NMR titration data are consistent with the model of amino acids binding to the luminol scaffold, which in turn, is consistent with the observed lower selectivity of chemiluminescent compound precursor 200 than chemiluminescent compound precursor 202 for H$_2$S over amino acid containing thiols. While in some embodiments, a difference in selectivity was observed for certain chemiluminescent compound precursors, these embodiments are both highly active and useful for determining the presence of, and quantifying the amount of, $H_2S$ in a sample.

Example 12

The ability of chemiluminescent compound precursor 202 to detect enzymatically-produced $H_2S$ was also demonstrated by using isolated and purified cystathionine γ-lyase (CSE). CSE is a PLP-dependent enzyme that converts Hcy or Cys to $H_2S$ and can be inhibited by β-cyano-L-alanine (BCA). Control experiments measuring the response of chemiluminescent compound precursor 202 to Hcy, BCA, and the reaction by-products pyruvate (Pyr) and $NH_3$ all showed negligible (p<0.005) chemiluminescent responses (FIG. 12, white bars). Similarly, incubation of chemiluminescent compound precursor 202 with CSE in the absence of substrate showed no response. Introduction of the Hcy substrate to CSE, however, resulted in a robust response by comparison to CSE alone (p<0.001) or CSE and Hcy inhibited with BCA (p<0.005) (FIG. 12, light grey bars).

Figure 29:
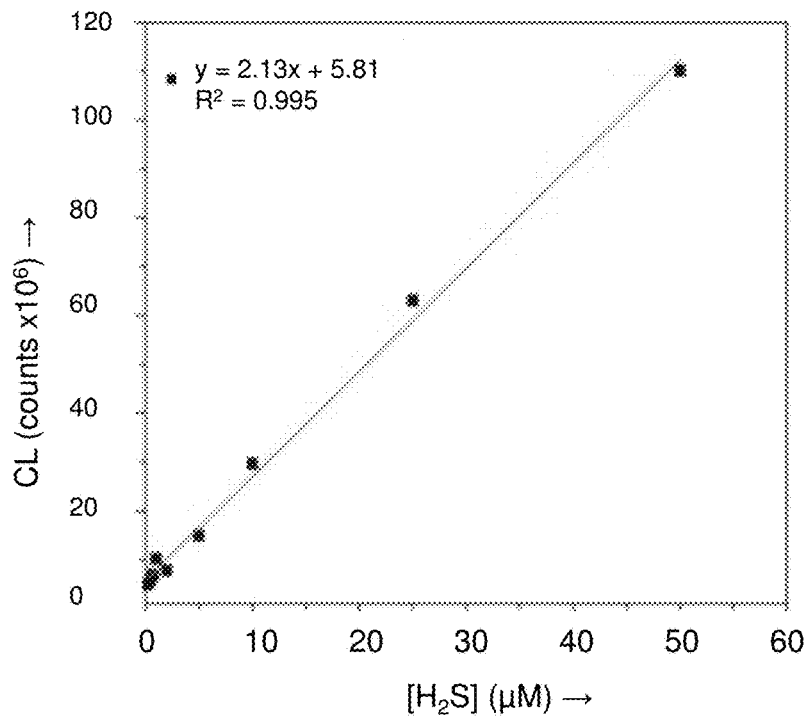
FIG. 29 is a graph of concentration dependence of H$_2$S on the luminescence of a particular H$_2$S-reactive compound embodiment.
Figure 30:
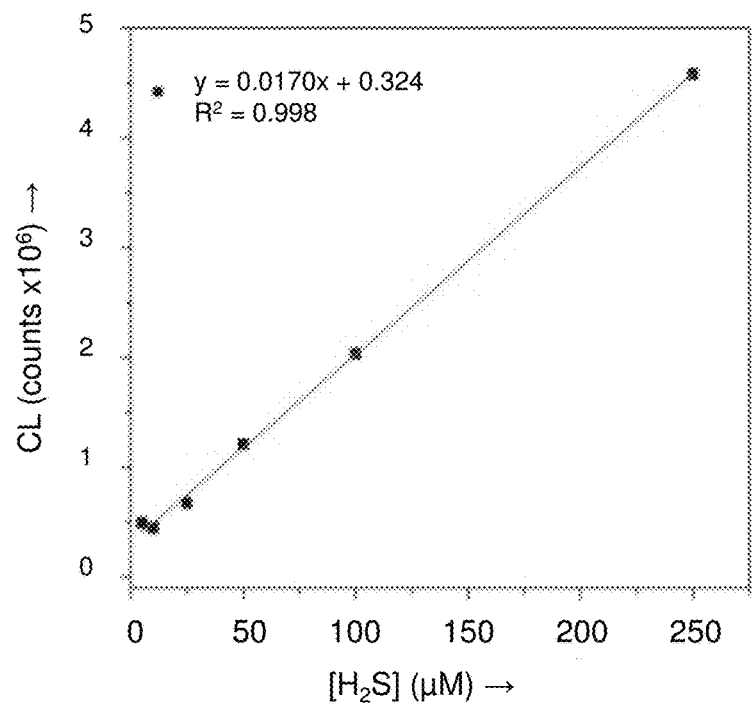
FIG. 30 is a graph of concentration dependence of H$_2$S on the luminescence of a particular H$_2$S-reactive compound embodiment.

Furthermore, quantification of the $H_2S$ produced from the CSE/Hcy system using the chemiluminescent response curve in FIG. 29 is in agreement with the expected concentrations based on known CSE kinetic parameters. Taken together, these results demonstrate the ability of chemiluminescent compound precursor 202 to detect and quantify enzymatically-produced $H_2S$ from CSE and also differentiate between inhibited and uninhibited enzymes.

Example 13

The ability of chemiluminescent compound precursor 202 to detect and quantify endogenously-produced $H_2S$ in C6 cells was determined. C6 cells express CSE and produce $H_2S$ endogenously, thereby providing an ideal platform to demonstrate $H_2S$ detection in the presence of other active biological processes. Incubation of chemiluminescent compound precursor 202 with C6 cell lysates lacking CSE substrates resulted in minimal luminescent response (FIG. 12, dark grey bars). This result confirmed that other biological species in the cellular milieu do not activate chemiluminescent compound precursor 202. By contrast, addition of Hcy as a CSE substrate significantly increased luminescence (p<0.001) by comparison to lysates lacking substrate. Furthermore, addition of Hcy and BCA abrogated the luminescent response (p<0.005), which is consistent with CSE inhibition. These results build upon the isolated CSE experiments and demonstrate that chemiluminescent compound precursor 202 can detect endogenously-produced $H_2S$ even in the presence of other biological species.

Example 14

General Procedure for Azidification

The appropriate aminophthalhydrazide (0.10 g, 0.56 mmol) was dissolved in 5 mL dry DMSO. After cooling the solution to 0° C., 0.10 mL (0.85 mmol) of tert-butyl nitrite was added drop-wise. The reaction mixture was stirred for 1 hour and then 0.95 mL (0.68 mmol) of trimethylsilyl azide (TMS-$N_3$) was added. The reaction mixture was allowed to warm to room temperature and stir for 1 hour. Volatile components of the reaction mixture were then removed under vacuum without heating. The remaining DMSO solution was diluted with 50 mL of 5% dichloromethane in hexanes to yield a precipitate. The precipitate was collected and washed with dichloromethane to afford the desired azide.

3-Azidophthalhydrazide (200)

Figure 38A:
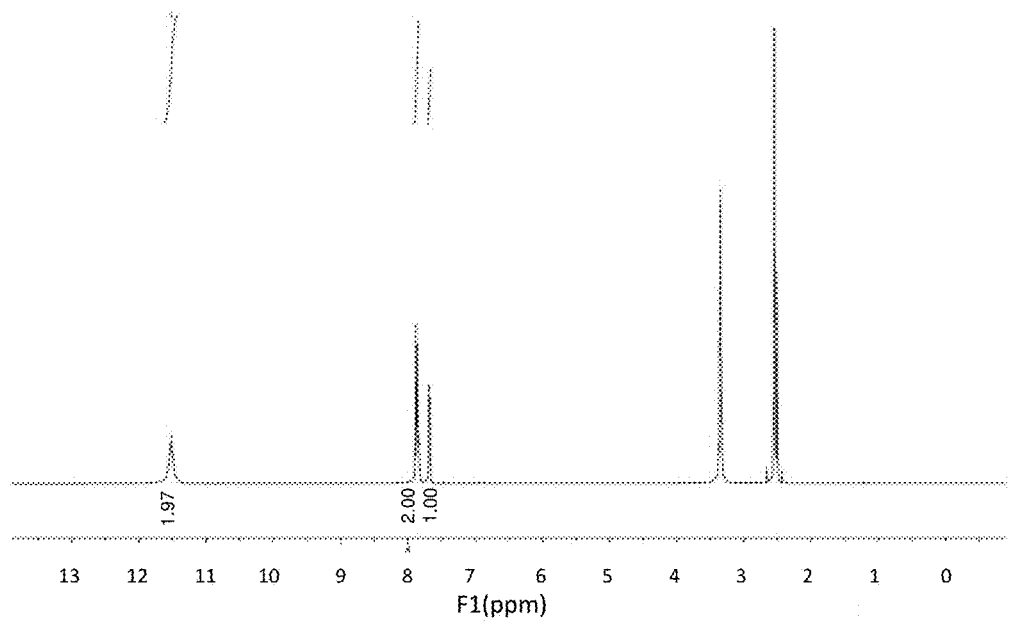
FIGS. 38A and 38B are $^1$H NMR and $^{13}$C NMR spectra, respectively, of an H$_2$S-reactive compound embodiment disclosed herein.
Figure 38B:
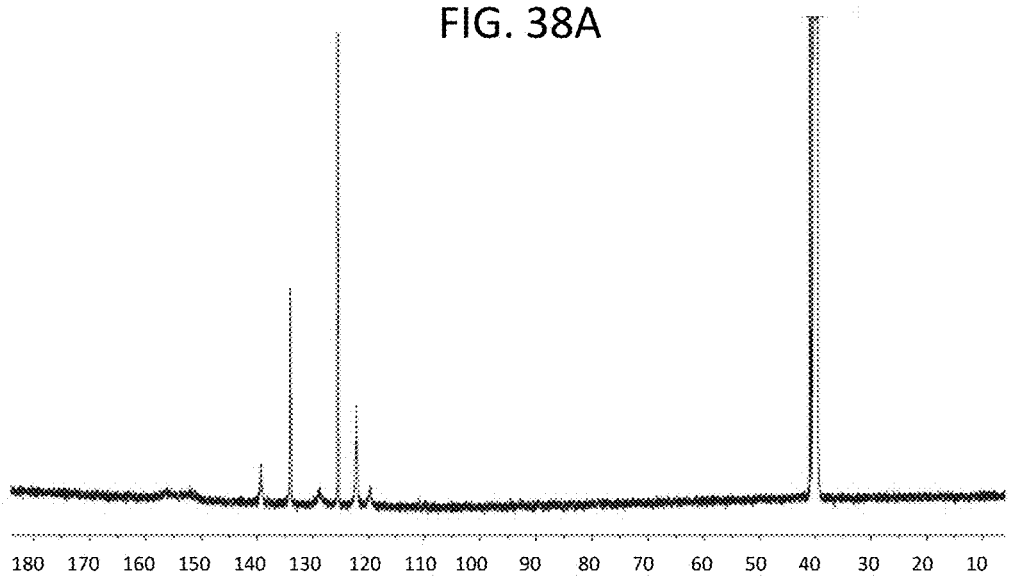

Yield: 95 mg (83%). 1H NMR (600 MHz, DMSO-d6) δ: 11.52 (b, 2H, NH), 7.87 (m, 2H, ArH), 7.68 (d, J=7.7 Hz, 1H, ArH). 13C{1H} NMR (150 MHz, DMSO-d6) δ: 156.0, 152.0, 139.3, 134.0, 128.8, 125.5, 122.2, 119.7. IR (cm$^{-1}$): 3167, 3013, 1896, 2617, 2191 [v(N3)], 2101 [v(N3)], 1650, 1611, 1597, 1487, 1454, 1357, 1326, 1290, 1206, 1193, 1180, 1164, 1121, 1067, 1003, 980, 902, 871, 769, 733, 697. Mp: 165° C. (dec.). HRMS-ESI (m/z): [M+H]+ calcd for [C8H6O2N5]+, 204.0521. found 204.0524. The corresponding $^1$H NMR and $^{13}$C NMR spectra are provided in FIGS. 38A and 38B, respectively.

4-Azidophthalhydrazide (202)

Figure 39A:
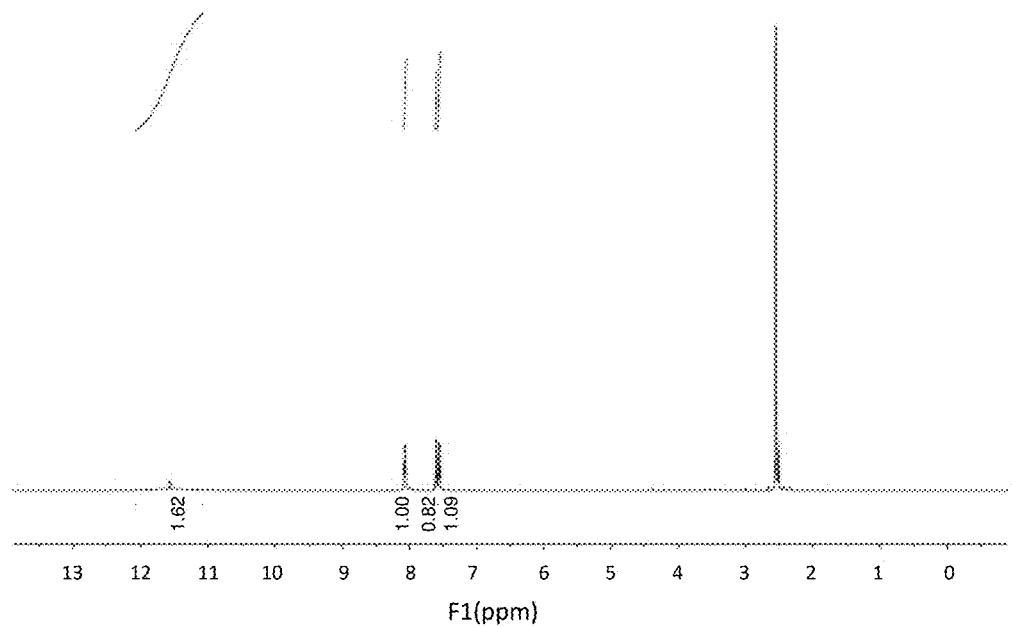
FIGS. 39A and 39B are $^1$H NMR and $^{13}$C NMR spectra, respectively, of an H$_2$S-reactive compound embodiment disclosed herein.
Figure 39B:
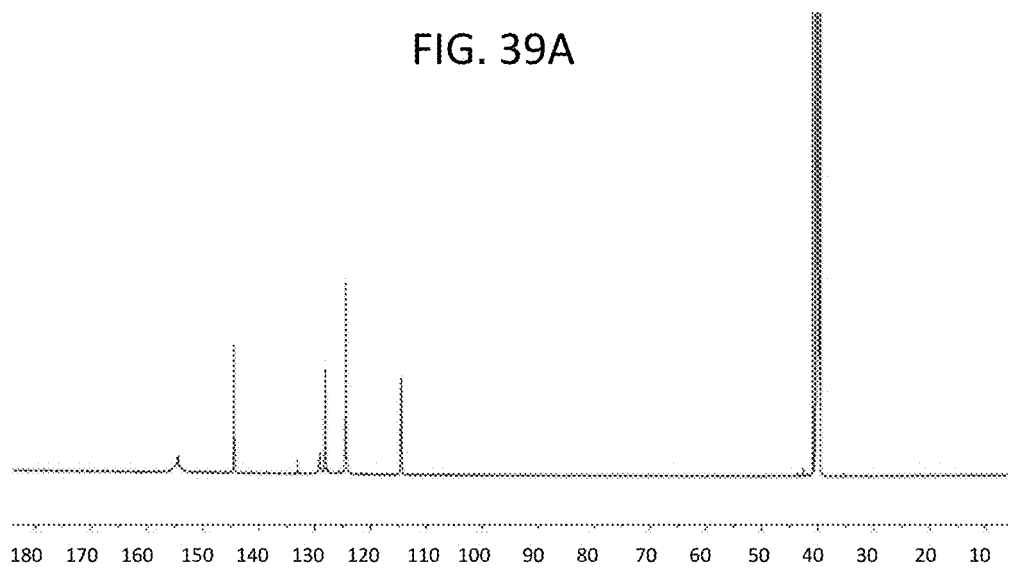

Yield: 100 mg (87%). 1H NMR (600 MHz, DMSO-d6) δ: 11.57 (s, br, 2H, NH), 8.07 (d, J=8.5 Hz, 1H, ArH), 7.60 (s, 1H, ArH), 7.57 (dd, J=8.5, 2.3 Hz, 1H, ArH). 13C{1H} NMR (150 MHz, DMSO-d6) δ: 154.6, 154.4, 144.4, 133.0, 129.0, 128.1, 124.4, 114.5. IR (cm$^{-1}$): 3417 3164, 3008, 2914, 2120 [v(N3)], 1662, 1603, 1554, 1496, 1458, 1435, 1405, 1367, 1344, 1290, 1252, 1218, 1172, 1108, 951, 819, 731, 646. Mp: 165° C. (dec.). HRMS-EI (m/z): [M]+ calcd for [C8H5O2N5]+, 203.04433. found 203.04392. The corresponding $^1$H NMR and $^{13}$C NMR spectra are provided in FIGS. 39A and 39B, respectively.

Bioluminescent Compounds

Example 15

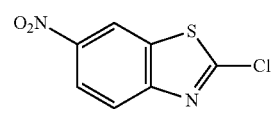

2-chloro-6-nitrobenzothiazole (1102)

1102 was synthesized according to the method of Katz, described in J. Am. Chem. Soc., 1951, 73, 4007-4010, the relevant portion of which is incorporated herein by reference. 2-chlorobenzothiazole (15.0 g, 88.4 mmol) was dissolved in 50 mL of concentrated sulfuric acid and chilled to 4° C. in an ice bath. Potassium nitrate (9.8 g, 97.2 mmol) was added portion wise as a solid over 10 minutes, and the reaction was allowed to warm to room temperature. After stirring for 30 minutes, the reaction mixture was quenched by pouring onto a mixture of ice and water. A yellow solid precipitated upon quenching, and washing the solid with hot ethanol yielded 1102 (18.8 g, 99%). $^1$H NMR: (600 MHz, CDCl$_3$) δ: 8.77 (d, J=2.4 Hz, 1H), 8.40 (dd, J=10.0 Hz, 2.4 Hz, 1H), 8.10 (d, J=10.0 Hz, 1H).

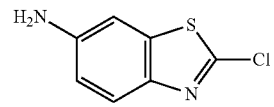

6-amino-2-chlorobenzothiazole (1104)

1104 was prepared according to a modification to the method of Katz, as disclosed by Qi et al., in *Bioconjugate Chem.*, 2011, 22, 1758-1762, the relevant portion of which is incorporated herein by reference. Dilute aqueous HCl (4.0 mL, 3M) was added to a suspension of 1102 (1.0 g, 4.66 mmol) in 15 mL EtOH in the absence of magnetic stirring. Iron powder (1.5 g, 23.3 mmol) was added, and the reaction mixture was refluxed for 3 hours. The resulting solution was diluted with saturated NaHCO$_3$, and extracted with chloroform. The organic layer was dried and evaporated giving a brown semi-solid. Silica gel chromatography (EtOAc: Hexanes, 20%-40% gradient) yielded 1104 (520 mg, 60%) as an off white solid. $^1$H NMR: (600 MHz, CDCl$_3$) δ: 7.66 (d, J=10 Hz, 1H), 6.96 (d, J=2.4 Hz, 1H), 6.80 (dd, J=10.0 Hz, 2.4 Hz, 1H), 3.89 (b, 2H, NH$_2$).

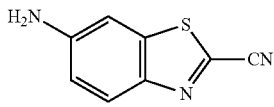 [SMILES: N#Cc1nc2ccc(N)cc2s1]

6-amino-cyanobenzothiazole (1106)

1106 was prepared according to a modification to the method of White, as disclosed in J. Am. Chem. Soc. 1966, 88. 2015-2019, the relevant portion of which is incorporated herein by reference. In the absence of water, 3 (500 mg, 2.7 mmol) and KCN (350 mg, 5.4 mmol) were dissolved in 30 mL DMSO. The reaction mixture was heated to 120° C. for 4 hours before cooling to room temperature. The solution was diluted in pH 7.4 PBS buffer and extracted with EtOAc before isolating in vacuo. Silica gel chromatography of the resulting solid (3:2 Hexanes:EtOAc, R$_f$=0.5, blue fluorescent under UV irradiation) yielded 1106 (220 mg, 47%) as a brown solid. $^1$H NMR: (600 MHz, CD$_2$Cl$_2$) δ: 7.93 (d, J=10 Hz, 1H), 7.11 (d, J=2.4 Hz, 1H), 6.98 (d, J=10.0 Hz, 2.4 Hz, 1H), 4.23 (b, 2H, NH$_2$), IR (cm$^{-1}$): 3521, 3402, 3253, 2200(ν-CN), 1687, 1585, 1501, 1486, 1453, 1398.

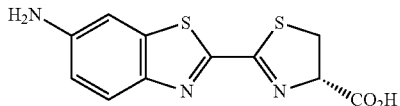

Aminoluciferin (1110)

1110 was prepared according a modification to the method of White as disclosed in *J Am Chem Soc.* 1966, 88, 2015-2019, the relevant portion of which is incorporated herein by reference. Under anaerobic conditions, 1106 (30 mg, 0.171 mmol) was suspended in a mixture of 1:1 MeOH: water at room temperature. D-cysteine (22.8 mg, 0.188 mmol) and potassium carbonate (23.5 mg, 0.171 mmol) were then added to the solution and allowed to stir for 1 hour. Upon completion the solution fluoresces yellow-green. The MeOH was evaporated off and the aqueous layer was washed with EtOAc. The pH of the solution was reduced to 3 with HCl, and extracted with EtOAc. The extracted organics were dried under vacuum and washed with hexanes to give 1110 (38.2 mg, 80%) as a yellow solid. $^1$H NMR: (600 MHz, DMSO-d$_6$) δ: 13.16 (b, 1H, COOH), 7.78 (d, J=9.0 Hz, 1H), 7.08 (d, J=1.8 Hz, 1H), 6.86 (dd, J=9.0 Hz, 1.8 Hz, 1H,), 5.85 (b, 2H, NH$_2$), 5.37 (t, J=8.4 Hz 1H), 3.68 (dt, J=55.8 Hz, 9.6 Hz, 2H). $^{13}$C NMR: (150 MHz, DMSO-d$_6$) δ: 171.8, 164.8, 153.7, 149.7, 144.6, 138.3, 125.0, 116.4, 103.5, 78.5, 35.01.

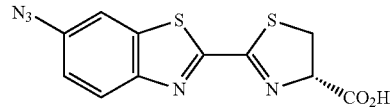

Compound 300

1110 (38.2 mg, 0.137 mmol) was suspended in anhydrous MeCN in the absence of light at 4° C. in an ice bath. Tert-butyl nitrite (24 μL, 0.205 mmol) and azidotrimethylsilane (22 μL, 0.164) were added drop-wise to the suspension, and the mixture was allowed to stir at room temperature for 3 hours. The volatiles were removed under vacuum, and the resulting red solid was washed with hexanes to afford 300 (37.7 mg, 90%). $^1$H NMR: (600 MHz, DMSO-d$_6$) δ: 13.21 (b, 1H, COOH), 8.18 (d, J=9.0 Hz, 1H), 8.08 (d, J=2.4 Hz, 1H), 7.34 (dd, J=9.0 Hz, 2.4 Hz, 1H), 5.46 (t, J=9.0 Hz 1H), 3.76 (dt, J=48.6 Hz, 9.6 Hz, 2H). $^{13}$C NMR: (150 MHz, DMSO-d$_6$) δ: 171.5, 164.8, 160.8, 150.5, 139.5, 137.5, 125.7, 120.0, 113.2, 78.6, 35.3. IR (cm$^{-1}$): 2114(ν-CN), 1731, 1584, 1553, 1492.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A method, comprising:
providing an H$_2$S-reactive compound, or a composition thereof, represented by the structure of Formula 1

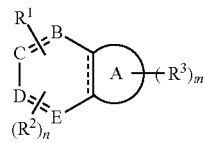

Formula 1 wherein R$^1$ is selected from an azide, fluoro, bromo, iodo, mesylate, besylate, tosylate, triflate, ether, or thioether;
R$^2$ is selected from nitro, haloalkyl, cyano, sulfonate, carboxyl, ester, aldehyde, ketone, or N(R$^5$)$_3$+ wherein each R$^5$ independently is selected from hydrogen, alkyl, aryl, alkenyl, alkynyl, or combinations thereof;
each R$^3$ independently is a 5- or 6-membered heteroaryl group or a 5- or 6-membered heterocyclyl;
at least one of B, C, D, or E is carbon bound to R$^1$ and the remaining of B, C, D, and E independently are CH, CR$^2$, or nitrogen;
n is 0, 1, 2, or 3;
m is 0, 1, or 2;

ring A is selected from

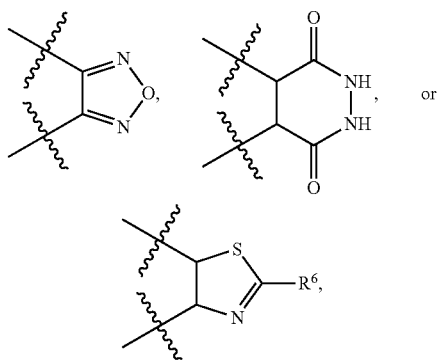

wherein R⁶ is a heterocyclyl or a heteroaryl; and
wherein the H₂S-reactive compound is other than 4-azido-7-nitrobenzo[c][1,2,5]oxadiazole and 2-(6-((4-boronobenzyl)oxy)benzo[d]thiazol-2-yl)-4,5-dihydrothiazole-4-carboxylic acid;
exposing a sample to the H₂S-reactive compound, or composition thereof; and
analyzing the sample for a reaction product obtained from reaction between the H₂S-reactive compound and H₂S to determine whether H₂S is present.

2. The method of claim 1, wherein R¹ is an azide.

3. The method of claim 1, wherein R¹ is an ether having a formula

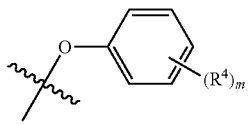

wherein each R⁴ independently is selected from halogen, alkoxy, nitro, haloalkyl, cyano, sulfonate, carboxyl, ester, aldehyde, ketone, amine, hydroxyl, amide, alkyl, alkenyl, alkynyl, or aryl; and m can be 0, 1, 2, 3, 4, or 5.

4. The method of claim 1, wherein R¹ is a thioether having a formula

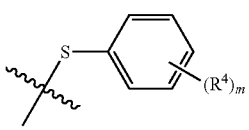

wherein each R⁴ independently is selected from independently can be selected from halogen, alkoxy, nitro, haloalkyl, cyano, sulfonate, carboxyl, ester, aldehyde, ketone, amine, hydroxyl, amide, alkyl, alkenyl, alkynyl, or aryl; and m can be 0, 1, 2, 3, 4, or 5.

5. The method of claim 1, wherein the sample is a biological sample selected from a cell, tissue, or bodily fluid.

6. The method of claim 1, wherein the sample is an environmental sample selected from a water sample, a soil sample, a gas sample, a plant sample, or an air sample.

7. The method of claim 1, wherein analyzing the sample comprises visually detecting a color change produced by a reaction product obtained from reaction between the H₂S-reactive compound and H₂S.

8. The method of claim 7, wherein the reaction product has an absorbance ranging from 450 nm to 600 nm.

9. The method of claim 1, further comprising exposing the sample to an oxidant, a transition metal cation, a luciferase enzyme, a peroxidase enzyme, an enhancer, a base, or any combination thereof, in any order.

10. The method of claim 9, wherein analyzing comprises visually detecting chemiluminescence or bioluminescence produced by the compound.

11. The method of claim 10, wherein the chemiluminescence or bioluminescence emits at a wavelength ranging from 400 nm to 600 nm.

12. The method of claim 1, wherein the providing an H₂S-reactive compound, or a composition thereof, comprises providing a colorimetric compound precursor, or a composition thereof, having a formula

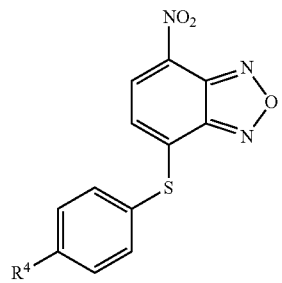

wherein R⁴ is selected from H, F, OMe, or NO₂;
wherein the exposing the sample to the H₂S-reactive compound, or composition thereof comprises exposing a biological or environmental sample to the colorimetric compound precursor, or composition thereof; and
wherein the analyzing the sample comprises analyzing the biological or environmental sample for a color change produced by a reaction product obtained from reaction between the colorimetric compound precursor and H₂S.

13. The method of claim 1, wherein the providing an H₂S-reactive compound, or a composition thereof, comprises providing a chemiluminescent compound precursor, or a composition thereof, having a formula

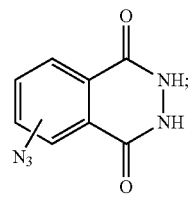

wherein the exposing the sample to the H₂S-reactive compound, or composition thereof comprises exposing the sample to the chemiluminescent compound precursor, or composition thereof, a peroxidase enzyme, a transition metal cation, an oxidant, an enhancer, a base, or combination thereof, in any order; and
wherein the analyzing the sample comprises analyzing the biological or environmental sample for chemiluminescence produced by a reaction product obtained from the chemiluminescent compound precursor.

14. The method of claim 1, wherein the providing an H₂S-reactive compound, or a composition thereof, comprises providing a bioluminescent compound precursor, or a composition thereof, having a formula

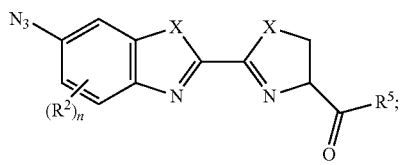

wherein the exposing the sample to the H₂S-reactive compound, or composition thereof comprises exposing a biological sample to the bioluminescent compound precursor, or composition thereof and exposing the bioluminescent compound precursor, or composition thereof, to a luciferase enzyme; and wherein the analyzing the sample comprises analyzing the biological sample for bioluminescence produced by a reaction product obtained from the bioluminescent compound precursor.

15. The method of claim 1, wherein the H₂S-reactive compound is selected from

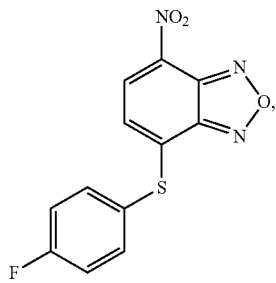
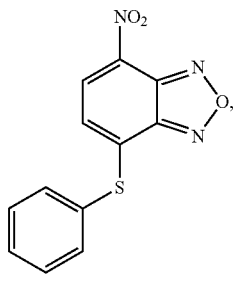
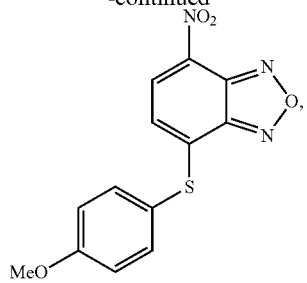
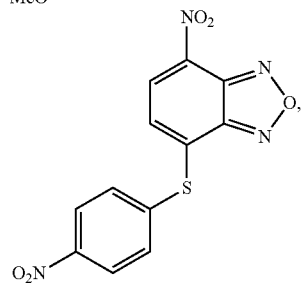
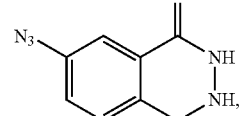
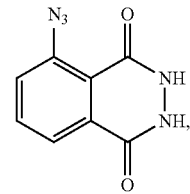

or combinations thereof.

16. The method of claim 1, wherein the sample is an environmental sample.

* * * * *